United States Patent
Parmee et al.

(10) Patent No.: US 7,598,285 B2
(45) Date of Patent: Oct. 6, 2009

(54) PYRAZOLE DERIVATIVES, COMPOSITIONS CONTAINING SUCH COMPOUNDS AND METHODS OF USE

(75) Inventors: Emma R. Parmee, Scotch Plains, NJ (US); Yusheng Xiong, Plainsboro, NJ (US); Jian Guo, Scotch Plains, NJ (US); Rui Liang, East Brunswick, NJ (US); Linda Brockunier, Orange, NJ (US)

(73) Assignee: Merck & Co., Inc, Rahway, NJ (US)

( * ) Notice: Subject to any disclaimer, the term of this patent is extended or adjusted under 35 U.S.C. 154(b) by 602 days.

(21) Appl. No.: 11/144,332

(22) Filed: Jun. 3, 2005

(65) Prior Publication Data

US 2005/0272794 A1    Dec. 8, 2005

Related U.S. Application Data

(60) Provisional application No. 60/577,116, filed on Jun. 4, 2004.

(51) Int. Cl.
*A61K 31/416* (2006.01)
*C07D 231/02* (2006.01)

(52) U.S. Cl. .................. 514/406; 548/377.1; 548/364.4

(58) Field of Classification Search .................. None
See application file for complete search history.

(56) References Cited

U.S. PATENT DOCUMENTS

| | | | |
|---|---|---|---|
| 5,670,503 | A | 9/1997 | Kawai et al. |
| 5,776,954 | A | 7/1998 | de Laszlo et al. |
| 6,057,335 | A | 5/2000 | Fukami et al. |
| 6,218,431 | B1 | 4/2001 | Schoen et al. |
| 6,420,427 | B1 | 7/2002 | Takahashi et al. |
| 6,440,963 | B1 | 8/2002 | Leonardi et al. |
| 6,503,949 | B1 | 1/2003 | Lau et al. |
| 6,562,807 | B2 | 5/2003 | Jorgensen et al. |
| 6,613,942 | B1 | 9/2003 | Ling et al. |
| 6,762,318 | B2 | 7/2004 | Kodra et al. |
| 6,790,810 | B2 | 9/2004 | Yanagi et al. |
| 6,881,746 | B2 | 4/2005 | Lau et al. |
| 2005/0171196 | A1 | 8/2005 | Fujii et al. |
| 2006/0084681 | A1 | 4/2006 | Shen et al. |
| 2007/0088070 | A1* | 4/2007 | Parmee et al. ............... 514/406 |

FOREIGN PATENT DOCUMENTS

| | | |
|---|---|---|
| EP | 1 400 243 A1 | 3/2004 |
| RU | 2 124 517 C1 | 1/1999 |
| RU | 2001110360 | 3/2003 |
| WO | WO 97/16442 | 5/1997 |
| WO | WO 98/21957 | 5/1998 |
| WO | WO 98/22108 | 5/1998 |
| WO | WO 98/22109 | 5/1998 |
| WO | WO 98/47509 | 10/1998 |
| WO | WO 99/32448 | 7/1999 |
| WO | WO 00/15229 | 3/2000 |
| WO | WO 00/39088 | 7/2000 |
| WO | WO 02/08188 A1 | 1/2002 |
| WO | WO 02/40444 A1 | 5/2002 |
| WO | WO 03/051357 A1 | 6/2003 |
| WO | WO 03/053938 A1 | 7/2003 |
| WO | WO 03/097619 A1 | 11/2003 |
| WO | WO 2004/009158 A2 | 1/2004 |
| WO | WO 2004/050039 A2 | 6/2004 |
| WO | WO 2004/092146 A2 | 10/2004 |
| WO | WO 2004/100875 A2 | 11/2004 |
| WO | WO 2005/121097 | 12/2005 |

OTHER PUBLICATIONS

Kurukulasuriya, R., "Biaryl amide glucagon receptor antagonists", Bioorganic & Medicinal Chemistry Letters, vol. 14, pp. 2047-2050, 2004.

M. J. Burk et al., "Catalytic Asymmetric Reductive Amination of Ketones via Highly Enantioselective Hydrogenation of the C=N Double Bond", Tetrahedron, vol. 50, No. 15, pp. 4399-4428 (1994).

* cited by examiner

*Primary Examiner*—Kamal A Saeed
(74) *Attorney, Agent, or Firm*—Richard C. Billups; Catherine D. Fitch

(57) ABSTRACT

Pyrazoles having a naphthyl group attached are disclosed. The compounds are useful for treating type 2 diabetes and related conditions. Pharmaceutical compositions and methods of treatment are also included.

23 Claims, No Drawings

PYRAZOLE DERIVATIVES, COMPOSITIONS CONTAINING SUCH COMPOUNDS AND METHODS OF USE

CROSS-REFERENCE TO RELATED APPLICATIONS

The present invention is related to U.S. provisional application Ser. No. 60/577,116, filed Jun. 4, 2004, priority of which is claimed.

BACKGROUND OF THE INVENTION

The present invention relates to pyrazole derivatives, compositions containing such compounds and various methods of treatment relating to type 2 diabetes mellitus and related conditions.

Diabetes refers to a disease process derived from multiple causative factors and is characterized by elevated levels of plasma glucose (hyperglycemia) in the fasting state or following glucose administration during an oral glucose tolerance test. Frank diabetes mellitus (e.g., a blood glucose level>126 mg/dL in a fasting state) is associated with increased and premature cardiovascular morbidity and mortality, and is related directly and indirectly to various metabolic conditions, including alterations of lipid, lipoprotein and apolipoprotein metabolism.

Patients with non-insulin dependent diabetes mellitus (type 2 diabetes mellitus), approximately 95% of patients with diabetes mellitus, frequently display elevated levels of serum lipids, such as cholesterol and triglycerides, and have poor blood-lipid profiles, with high levels of LDL-cholesterol and low levels of HDL-cholesterol. Those suffering from Type 2 diabetes mellitus are thus at an increased risk of developing macrovascular and microvascular complications, including coronary heart disease, stroke, peripheral vascular disease, hypertension (for example, blood pressure>130/80 mmHg in a resting state), nephropathy, neuropathy and retinopathy.

Patients having type 2 diabetes mellitus characteristically exhibit elevated plasma insulin levels compared with nondiabetic patients; these patients have developed a resistance to insulin stimulation of glucose and lipid metabolism in the main insulin-sensitive tissues (muscle, liver and adipose tissues). Thus, Type 2 diabetes, at least early in the natural progression of the disease is characterized primarily by insulin resistance rather than by a decrease in insulin production, resulting in insufficient uptake, oxidation and storage of glucose in muscle, inadequate repression of lipolysis in adipose tissue, and excess glucose production and secretion by the liver. The net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease. plasma glucose (hyperglycemia). Hyperinsulinemia is a risk factor for developing hypertension and may also contribute to vascular disease.

Glucagon serves as the major regulatory hormone attenuating the effect of insulin in its inhibition of liver gluconeogenesis and is normally secreted by alpha cells in pancreatic islets in response to falling blood glucose levels. The hormone binds to specific receptors in liver cells that triggers glycogenolysis and an increase in gluconeogenesis through cAMP-mediated events. These responses generate glucose (e.g. hepatic glucose production) to help maintain euglycemia by preventing blood glucose levels from falling significantly. In addition to elevated levels of circulating insulin, type 2 diabetics have elevated levels of plasma glucagon and increased rates of hepatic glucose production. Antagonists of glucagon are useful in improving insulin responsiveness in the liver, decreasing the rate of gluconeogenesis and glycogenolysis, and lowering the rate of hepatic glucose output resulting in a decrease in the levels of plasma glucose.

SUMMARY OF THE INVENTION

The present invention is directed to a compound represented by formula I:

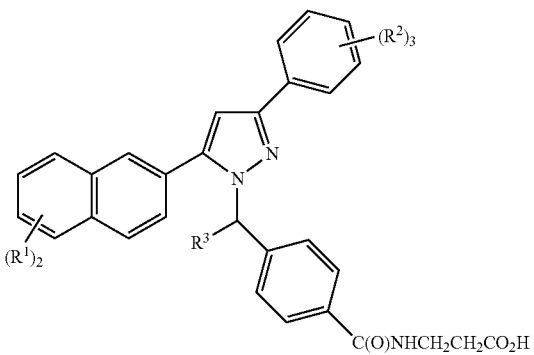

or a pharmaceutically acceptable salt or solvate thereof, wherein:
each $R^1$ is H or is selected from the group consisting of:
(a) halo, OH, $CO_2R^4$, CN, $SO_pR^5$ or $NO_2$,
(b) $C_{1-6}$alkyl or $OC_{1-6}$alkyl optionally substituted with: (1) 1-5 halo groups up to a perhaloalkyl group; (2) $CO_2R^4$; (3) phenyl optionally substituted as follows: (i) 1-5 halo groups, (ii) 1 $CO_2R^4$, CN, $S(O)_pR^5$, $NO_2$ or $C(O)NR^6R^7$ group, (iii) 1-2 $C_{1-10}$alkyl or alkoxy groups, each optionally substituted with: 1-5 halo, up to perhaloalkyl, and 1-2 OH or $CO_2R^4$ groups;
each $R^2$ is selected from $R^1$ as defined above, or 2 $R^2$ groups can be taken together to represent a fused 5-6 membered cyclic structure containing 1-2 oxygen atoms, and 1-2 carbon atoms each of which is optionally substituted with 1-2 F atoms;
$R^3$ is H or $C_{1-3}$alkyl;
$R^4$ is H, $C_{1-6}$alkyl, and
$R^5$ represents a member selected from the group consisting of: $C_{1-10}$alkyl, Aryl or Ar—$C_{1-10}$alkyl;
$R^6$ and $R^7$ each independently represent H or $C_{1-3}$alkyl, and p is 0, 1 or 2.

DETAILED DESCRIPTION OF THE INVENTION

The invention is described herein in detail using the terms defined below unless otherwise specified.

"Alkyl", as well as other groups having the prefix "alk", such as alkoxy, alkanoyl and the like, means carbon chains which may be linear, branched, or cyclic, or combinations thereof, containing the indicated number of carbon atoms. If no number is specified, 1-10 carbon atoms are intended for linear or branched alkyl groups. Examples of alkyl groups include methyl, ethyl, propyl, isopropyl, butyl, sec- and teat-butyl, pentyl, hexyl, heptyl, octyl, nonyl and the like. Cycloalkyl is a subset of alkyl; if no number of atoms is specified, 3-10 carbon atoms are intended, forming 1-3 carbocyclic rings that are fused. Examples of cycloalkyl include cyclopropyl, cyclobutyl, cyclopentyl, cyclohexyl, cycloheptyl, decahydronaphthyl and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Aryl" (Ar) means mono- and bicyclic aromatic rings containing 6-12 carbon atoms. Examples of aryl include phenyl, naphthyl, indenyl and the like. "Aryl" also includes monocyclic rings fused to an aryl group. Examples include tetrahydronaphthyl, indanyl and the like.

"Heteroaryl" (HAR) means a mono- or bicyclic aromatic ring or ring system containing at least one heteroatom selected from O, S and N, with each ring containing 5 to 6 atoms. Examples include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl and the like. Heteroaryl also includes aromatic heterocyclic groups fused to heterocycles that are non-aromatic or partially aromatic, and aromatic heterocyclic groups fused to cycloalkyl rings. Heteroaryl also includes such groups in charged form, e.g., pyridinium.

"Heterocyclyl" (Hetcy) means mono- and bicyclic saturated rings and ring systems containing at least one heteroatom selected from N, S and O, each of said ring having from 3 to 10 atoms in which the point of attachment may be carbon or nitrogen. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like The term also includes partially unsaturated monocyclic rings that are not aromatic, such as 2- or 4-pyridones attached through the nitrogen or N-substituted-(1H, 3H)-pyrimidine-2,4-diones (N-substituted uracils). Heterocyclyl moreover includes such moieties in charged form, e.g., piperidinium.

"Halogen" (Halo) includes fluorine, chlorine, bromine and iodine.

When $R^1$ is other than H, it can be attached to the naphthyl group at any available point of attachment.

In its broadest aspect, the invention relates to a compound represented by formula I:

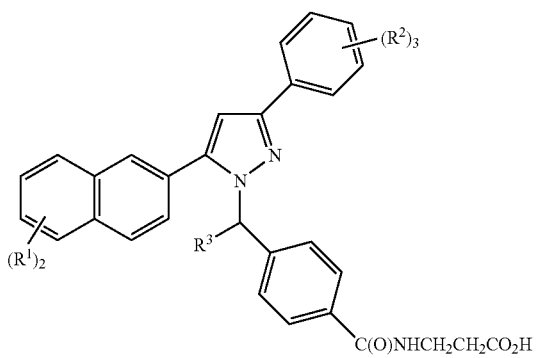

or a pharmaceutically acceptable salt or solvate thereof, wherein:

each $R^1$ is H or is selected from the group consisting of:
(a) halo, OH, $CO_2R^4$, CN, $SO_pR^5$ or $NO_2$,
(b) $C_{1-6}$alkyl or $OC_{1-6}$alkyl optionally substituted with: (1) 1-5 halo groups up to a perhaloalkyl group; (2) $CO_2R^4$; (3) phenyl optionally substituted as follows: (i) 1-5 halo groups, (ii) 1 $CO_2R^4$, CN, $S(O)_pR^5$, $NO_2$ or $C(O)NR^6R^7$ group, (iii) 1-2 $C_{1-10}$alkyl or alkoxy groups, each optionally substituted with: 1-5 halo, up to perhaloalkyl, and 1-2 OH or $CO_2R^4$ groups;

each $R^2$ is selected from $R^1$ as defined above, or 2 $R^2$ groups can be taken together to represent a fused 5-6 membered cyclic structure containing 1-2 oxygen atoms, and 1-2 carbon atoms each of which is optionally substituted with 1-2 F atoms;

$R^3$ is H or $C_{1-3}$alkyl;
$R^4$ is H, $C_{1-6}$alkyl, and
$R^5$ represents a member selected from the group consisting of: $C_{1-10}$alkyl, Aryl or Ar—$C_{1-10}$alkyl;
$R^6$ and $R^7$ each independently represent H or $C_{1-3}$alkyl, and p is 0, 1 or 2.

Another aspect of the invention that is of interest relates to a compound as described above with respect to formula I wherein one $R^1$ is H and the other is H or is selected from the group consisting of:
(a) halo, OH, $CO_2R^4$, CN, $SO_pR^5$ or $NO_2$,
(b) $C_{1-6}$alkyl or $OC_{1-6}$alkyl optionally substituted with: (1) 1-5 halo groups up to a perhaloalkyl group; (2) $CO_2R^4$; (3) phenyl optionally substituted as follows: (i) 1-5 halo groups, (ii) 1 $CO_2R^4$, CN, $S(O)_pR^5$, $NO_2$ or $C(O)NR^6R^7$ group, (iii) 1-2 $C_{1-10}$alkyl or alkoxy groups, each optionally substituted with: 1-5 halo, up to perhaloalkyl, and 1-2 OH or $CO_2R^4$ groups.

More particularly, another aspect of the invention that is of interest relates to a compound as described above with respect to formula I wherein one $R^1$ is H and the other is H or is selected from the group consisting of: (a) halo or OH; and (b) $C_{1-4}$alkyl or $OC_{1-4}$alkyl, each optionally substituted with 1-3 halo groups.

Another aspect of the invention that is of interest relates to a compound as described above with respect to formula I wherein each $R^2$ represents H or is selected from the group consisting of:
(a) halo selected from Cl and F, (b) $C_{1-6}$alkyl or $OC_{1-6}$alkyl optionally substituted with 1-3 halo groups, or two $R^2$ groups taken together represent a fused 5-6 membered cyclic structure containing 1-2 oxygen atoms, and 1-2 carbon atoms, each of which is optionally substituted with 1-2 F atoms.

Another aspect of the invention that is of interest relates to a compound as described above with respect to formula I wherein $R^3$ represents H or methyl.

More particularly, another aspect of the invention that is of interest relates to a compound as described above with respect to formula I wherein:
one $R^1$ is H and the other is H or are selected from the group consisting of:
(a) halo, OH, $CO_2R^4$, CN, $SO_pR^5$ or $NO_2$,
(b) $C_{1-6}$alkyl or $OC_{1-6}$alkyl optionally substituted with: (1) 1-5 halo groups up to a perhaloalkyl group; (2) $CO_2R^4$; (3) phenyl optionally substituted as follows: (i) 1-5 halo groups, (ii) 1 $CO_2R^4$, CN, $S(O)_pR^5$, $NO_2$ or $C(O)NR^6R^7$ group, (iii) 1-2 $C_{1-10}$alkyl or alkoxy groups, each optionally substituted with: 1-5 halo, up to perhaloalkyl, and 1-2 OH or $CO_2R^4$ groups;

each $R^2$ represents H or is selected from the group consisting of: (a) halo selected from Cl and F, (b) $C_{1-6}$alkyl or $OC_{1-6}$alkyl optionally substituted with 1-3 halo groups, or two $R^2$ groups taken together represent a fused 5-6 membered cyclic structure containing 1-2 oxygen atoms, and 1-2 carbon atoms, each of which is optionally substituted with 1-2 F atoms;

$R^3$ represents H or methyl;

$R^4$ is H or $C_{1-6}$alkyl;

$R^5$ represents a member selected from the group consisting of: $C_{1-10}$alkyl, Aryl or Ar—$C_{1-10}$alkyl;

$R^6$ and $R^7$ each independently represent H or $C_{1-3}$alkyl, and p is 0, 1 or 2.

Even more particularly, another aspect of the invention that is of interest relates to compounds of formula I or a pharmaceutically acceptable salt or solvate thereof, wherein one $R^1$ represents H and the other is selected from Cl, F, $CF_3$ or $OC_{1-3}$alkyl; and $R^2$ represents halo, $CF_3$, $OC_{1-3}$alkyl or $OCF_3$, and $R^3$ is H or methyl.

Another aspect of the invention that is of interest relates to a pharmaceutical composition comprising a compound as described above with respect to formula I in combination with a pharmaceutically acceptable carrier.

Another aspect of the invention that is of interest relates to a method of treating type 2 diabetes mellitus in a mammalian patient in need of such treatment comprising administering to said patient a compound as described above with respect to formula I in an amount that is effective to treat type 2 diabetes mellitus.

Another aspect of the invention that is of interest relates to a method of delaying the onset of type 2 diabetes mellitus in a mammalian patient in need thereof, comprising administering to the patient a compound as described above in accordance with formula I in an amount that is effective to delay the onset of type 2 diabetes mellitus.

Another aspect of the invention that is of interest relates to a method of treating hyperglycemia, diabetes or insulin resistance in a mammalian patient in need of such treatment which comprises administering to said patient a compound as described above in accordance with formula I in an amount that is effective to treat hyperglycemia, diabetes or insulin resistance.

Another aspect of the invention that is of interest relates to a method of treating non-insulin dependent diabetes mellitus in a mammalian patient in need of such treatment comprising administering to the patient an anti-diabetic effective amount of a compound in accordance with formula I as described above.

Another aspect of the invention that is of interest relates to a method of treating obesity in a mammalian patient in need of such treatment comprising administering to said patient a compound in accordance with formula I as described above in an amount that is effective to treat obesity.

Another aspect of the invention that is of interest relates to a method of treating Syndrome X in a mammalian patient in need of such treatment, comprising administering to said patient a compound in accordance with formula I as described above in an amount that is effective to treat Syndrome X.

Another aspect of the invention that is of interest relates to a method of treating a lipid disorder selected from the group consisting of dyslipidemia, hyperlipidemia, hypertriglyceridemia, hypercholesterolemia, low HDL and high LDL in a mammalian patient in need of such treatment, comprising administering to said patient a compound as described above with respect to formula I in an amount that is effective to treat said lipid disorder.

Another aspect of the invention that is of interest relates to a method of treating atherosclerosis in a mammalian patient in need of such treatment, comprising administering to said patient a compound in accordance with formula I as described above in an amount effective to treat atherosclerosis.

Another aspect of the invention that is of interest relates to a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient a compound in accordance with formula I as described above in an amount that is effective to treat said condition.

Another aspect of the invention that is of interest relates to a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound in accordance with formula I as described above in an amount that is effective to delay the onset of said condition.

Another aspect of the invention that is of interest relates to a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound of formula I as described above in an amount that is effective to reduce the risk of developing said condition.

Another aspect of the invention that is of interest relates to a method of treating a condition selected from the group consisting of:

(1) hyperglycemia, (2) low glucose tolerance, (3) insulin resistance, (4) obesity, (5) lipid disorders, (6) dyslipidemia, (7) hyperlipidemia, (8) hypentriglyceridemia, (9) hypercholesterolemia, (10) low HDL levels, (11) high LDL levels, (12) atherosclerosis and its sequelae, (1.3) vascular restenosis, (14) pancreatitis, (15) abdominal obesity, (16) neurodegenerative disease, (17)retinopathy, (18) nephropathy, (19) neuropathy, (20) Syndrome X, and other conditions and disorders where insulin resistance is a component, in a mammalian patient in need of such treatment, comprising administering to the patient effective amounts of a compound of formula I as described above, and a compound selected from the group consisting of:

(a) DPP-IV inhibitors, such as the compounds disclosed in U.S. Pat. No. 6,699,871B1 granted on Mar. 2, 2004, incorporated herein by reference; (b) insulin sensitizers selected from the group consisting of (i) PPAR agonists and (ii) biguanides; (c) insulin and insulin mimetics; (d) sulfonylureas and other insulin secretagogues; (e) alpha glucosidase inhibitors; (f)

other glucagon receptor antagonists; (g) GLP-1, GLP-1 mimetics, and GLP-1 receptor agonists; (h) GIP, GIP mimetics, and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid and salts thereof, (iv) PPAR alpha agonists, (v) PPAR alpha/gamma dual agonists, (vi) inhibitors of cholesterol absorption, (vii) acyl CoA:cholesterol acyltransferase inhibitors, (viii) anti-oxidants and (ix) LXR modulators; (k) PPAR delta agonists; (l) antiobesity compounds; (m) an ileal bile acid transporter inhibitor; (n) anti-inflammatory agents excluding glucocorticoids; (o) protein tyrosine phosphatase-1B (PTP-IB) inhibitors, and (p) CB1 antagonists/inverse agonists, such as rimonabant and those disclosed in WO03/077847A2, published on Sep. 25, 2003, and WO 05/000809 published on Jan. 6, 2005, incorporated herein by reference, said compounds being administered to the patient in amounts that are effective to treat said condition.

Another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor.

More particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor wherein the HMG-CoA reductase inhibitor is a statin.

Even more particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor, wherein the HMG CoA reductase inhibitor is a statin selected from the group consisting of lovastatin, simvastatin, pravastatin, fluvastatin, atorvastatin, itavastatin, ZD4522 and rivastatin.

Another aspect of the invention that is of interest relates to a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment therapeutically effective amounts of a compound of formula I as described above and an HMG-CoA reductase inhibitor.

Another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor.

More particularly, another aspect of the invention that is of interest relates to a method for delaying the onset of, or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is a statin.

Even more particularly, another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is a statin selected from the group consisting of: lovastatin, simvastatin, pravastatin, fluvastatin, atorvastatin, itavastatin, ZD4522 and rivastatin.

Yet even more particularly, another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is simvastatin.

Another aspect of the invention that is of interest relates to a method for delaying the onset or reducing the risk of developing atherosclerosis in a human patient in need of such treatment comprising administering to said patient effective amounts of a compound of formula I as described above and a cholesterol absorption inhibitor. More particularly, another aspect of the invention that is of interest relates to a method for delaying the onset or reducing the risk of developing atherosclerosis in a human patient in need of such treatment comprising administering to said patient effective amounts of a compound of formula I as described above and a cholesterol absorption inhibitor wherein the cholesterol absorption inhibitor is ezetimibe.

Another aspect of the invention that is of interest relates to a method for delaying the onset or reducing the risk of developing the other diseases and conditions mentioned above, in a mammalian patient in need of such treatment comprising administering to said patient effective amounts of a compound of formula I as described above, and a cholesterol absorption inhibitor.

More particularly, another aspect of the invention that is of interest relates to a method for delaying the onset or reducing the risk of developing the other diseases and conditions mentioned above, in a human patient in need of such treatment comprising administering to said patient effective amounts of a compound of formula I as described above, and a cholesterol absorption inhibitor, wherein the cholesterol absorption inhibitor is ezetimibe.

Another aspect of the invention that is of interest relates to a pharmaceutical composition comprising (1) a compound of formula I as described above; (2) a compound selected from the group consisting of: (a) DPP-IV inhibitors, such as those disclosed in U.S. Pat. No. 6,699,871B1 granted on Mar. 2, 2004; (b) insulin sensitizers selected from the group consisting of (i) PPAR agonists and (ii) biguanides; (c) insulin and insulin mimetics; (d) sulfonylureas and other insulin secretagogues; (e) alpha glucosidase inhibitors; (f) other glucagon receptor antagonists; (g) GLP-1, GLP-1 mimetics and GLP-1 receptor agonists; (h) GIP, GIP mimetics and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid or a salt thereof, (iv) PPAR alpha agonists, (v) PPAR alpha/gamma dual agonists, (vi) inhibitors of cholesterol absorption, (vii) acyl CoA:cholesterol acyltransferase inhibitors, (viii) anti-oxidants and (ix) LXR modulators; (k) PPAR delta agonists; (l) antiobesity compounds; (m) an ileal bile acid transporter inhibitor; (n) anti-inflammatory agents other than glucocorticoids; (o) protein tyrosine phosphatase-1B (PTP-1B) inhibitors; and (p) CB1 antagonist/inverse agonists, such as rimonabant, and those disclosed in WO03/077847A2 published on Sep. 25, 2003 and WO 05/000809 published on Jan. 6, 2005, and (3) a pharmaceutically acceptable carrier.

One pharmaceutical composition that is of interest is comprised of a compound of formula I as described herein, or a pharmaceutically acceptable salt or solvate thereof, in combination with a DPP-IV inhibitor selected from the group consisting of:

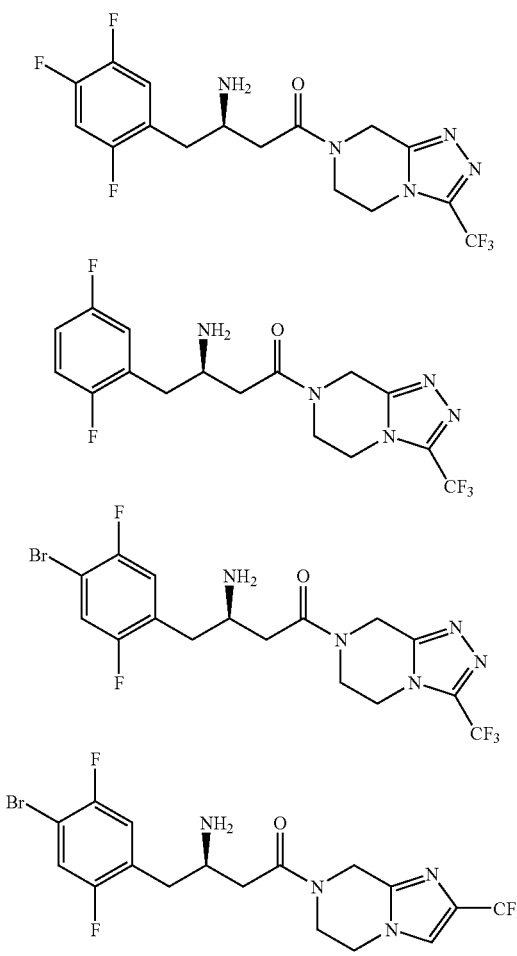

or a pharmaceutically acceptable salt or solvate thereof in combination with a pharmaceutically acceptable carrier.

Another pharmaceutical composition that is of particular interest is comprised of a compound of formula I as described herein, or a pharmaceutically acceptable salt or solvate thereof, in combination with a CB1 receptor antagonist/inverse agonist, in combination with a pharmaceutically acceptable carrier. Examples of CB1 antagonist/inverse agonists that are of particular interest in the invention described herein include rimonabant, the following which are disclosed in WO03/077847A2 published on Sep. 25, 2003:

(1) N-[3-(4-chlorophenyl)-1-methyl-2-phenylpropyl]-2-(4-chlorophenyloxy)-2-methylpropanamide;

(2) N-[3-(4-chlorophenyl)-1-methyl-2-phenylpropyl]-2-(2-pyridyloxy)-2-methylpropanamide;
(3) N-[3-(4-chlorophenyl)-1-methyl-2-(3-pyridyl)propyl]-2-(4-chlorophenyloxy)-2-methylpropanamide;
(4) N-[3-(4-chlorophenyl)-1-methyl-2-phenylpropyl]-2-(3,5-difluorophenyloxy)-2-methylpropanamide;
(5) N-[3-(4-chlorophenyl)-2-phenyl-1-methylpropyl]-2-(3,5-dichlorophenyloxy)-2-methylpropanamide;
(6) N-[3-(4-chlorophenyl)-1-methyl-2-phenylpropyl]-2-(3-chlorophenyloxy)-2-methylpropanamide;
(7) N-[3-(4-chlorophenyl)-2-(3,5-difluorophenyl)-1-methylpropyl]-2-(2-pyridyloxy)-2-methylpropanamide;
(8) N-[3-(4-chlorophenyl)-1-methyl-2-phenylpropyl]-2-(5-chloro-2-pyridyloxy)-2-methylpropanamide;
(9) N-[3-(4-chlorophenyl)-1-methyl-2-phenylpropyl]-2-(6-methyl-pyridyloxy)-2-methylpropanamide;
(10) N-[3-(4-chlorophenyl)-1-methyl-2-phenylpropyl]-2-(phenyloxy)-2-methylpropanamide;
(11) N-[(3-(4-chlorophenyl)-1-methyl-2-phenylpropyl]-2-(5-trifluoromethylpyridyloxy)-2-methylpropanamide;
(12) N-[3-(4-chlorophenyl)-2-(3-pyridyl)-1-methylpropyl]-2-(5-trifluoromethyl-2-methylpropanamide;
(13) N-[3-(4-chlorophenyl)-2-(3-cyanophenyl)-1-methylpropyl]-2-(5-trifluoromethyl-2-methylpropanamide;
(14) N-[3-(4-chlorophenyl)-2-(5-chloro-3-pyridyl)-1-methylpropyl]-2-(5-trifluoromethyl-2-pyridyloxy)-2-methylpropanamide;
(15) N-[3-(4-chlorophenyl)-2-(5-methyl-3-pyridyl)-1-methylpropyl]-2-(5-trifluoromethyl-2-pyridyloxy)-2-methylpropanamide;
(16) N-[3-(4-chlorophenyl)-2-(5-cyano-3-pyridyl)-1-methylpropyl]-2-(5-trifluoromethyl-2-pyridyloxy)-2-methylpropanamide;
(17) N-[3-(4-chlorophenyl)-2-(3-methylphenyl)-1-methylpropyl]-2-(5-trifluoromethyl-2-pyridyloxy)-2-methylpropanamide;
(18) N-[3-(4-chlorophenyl)-2-phenyl-1-methylpropyl]-2-(4-trifluoromethyl-2-pyridyloxy)-2-methylpropanamide;
(19) N-[3-(4-chlorophenyl)-2-phenyl-1-methylpropyl]-2-(4-trifluoromethyl-2-pyrimidyloxy)-2-methylpropanamide;
(20) N-[3-(4-chlorophenyl)-1-methyl-2-(thiophen-3-yl)propyl]-2-(5-chloro-2-pyridyloxy)-2-methylpropanamide;
(21) N-[3-(5-chloro-2-pyridyl)-2-phenyl-1-methylpropyl]-2-(5-trifluoromethyl-2-pyridyloxy)-2-methylpropanamide;
(22) N-[3-(4-methyl-phenyl)-1-methyl-2-phenylpropyl]-2-(4-trifluoromethyl-phenyloxy)-2-methylpropanamide;
(23) N-[3-(4-fluoro-phenyl)-2-(3-cyano-phenyl)-1-methylpropyl]-2-(5-trifluoromethyl-2-pyridyloxy)-2-methylpropanamide;
(24) N-[3-(4-chlorophenyl)-2-(1-indolyl)-1-methyl)propyl]-2-(5-trifluoromethyl-2-oxypyridine-2-yl)-2-methylpropanamide;
(25) N-[3-(4-chlorophenyl)-2-(7-azaindol-N-yl)-1-methyl)propyl]-2-(5-trifluoromethyl-2-pyridyloxy)-2-methylpropanamide;
(26) N-[3-(4-chloro-phenyl)-2-(1-indolinyl)-1-methylpropyl]-2-(5-trifluoromethyl-2-pyridyloxy)-2-methylpropanamide;
(27) N-[3-(4-chloro-phenyl)-2-(N-methyl-anilino)-1-methylpropyl]-2-(5-trifluoromethyl-2-pyridyloxy)-2-methylpropanamide;
(28) N-[3-(4-methoxy-phenyl)-2-(3-cyano-phenyl)-1-methylpropyl]-2-(5-trifluoromethyl-2-pyridyloxy)-2-methylpropanamide;

(29) N-[3-(4-chlorophenyl)-2-(3-cyanophenyl)-1-methylpropyl]-2-(6-trifluoromethyl-4-pyrimidyloxy)-2-methylpropanamide;

(30) N-[2-(3-cyanophenyl)-1,4-dimethylpentyl]-2-(5-trifluoromethyl-2-pyridyloxy)-2-methylpropanamide;

(31) N-[3-(4-chlorophenyl)-2-(1-oxido-5-cyano-3-pyridyl)-1-methylpropyl]-2-(5-trifuoromethyl-2-pyridyloxy)-2-methylpropanamide;

(32) N-[2-(3-cyanophenyl)-3-cyclobutyl-1-methylpropyl]-2-(5-trifluoromethyl-2-pyridyloxy)-2-methylpropanamide;

(33) N-[2-(3-cyanophenyl)-1-methyl-heptyl]-2-(5-trifluoromethyl-2-pyridyloxy)-2-methylpropanamide;

(34) N-[2-(3-cyanophenyl)-3-cyclopentyl-1-methylpropyl]-2-(5-trifluoromethyl-2-pyridyloxy)-2-methylpropanamide;

(35) N-[2-(3yanophenyl)-3-cyclohexyl-1-methylpropyl]-2-(5-trifluoromethyl-2-pyridyloxy)-2-methylpropanamide;

and in WO05/000809 published on Jan. 6, 2005, which includes the following:

3-{1-[Bis(4-chlorophenyl)methyl]azetidin-3-ylidene}-3-(3,5-difluorophenyl)-2,2-dimethylpropanenitrile 1-{1-[1-(4-chlorophenyl)pentyl]azetidin-3-yl}-1-(3,5-difluorophenyl)-2-methylpropan-2-ol 3-((S)-(4-chlorophenyl){3-[(1S)-1-(3,5-difluorophenyl)-2-hydroxy-2-methylpropyl]azetidin-1-yl}methyl)benzonitrile 3-((S)-(4-chlorophenyl){3-[(1S)-1-(3,5-difluorophenyl)-2-fluoro-2-methylpropyl]azetidin-1-yl}methyl)benzonitrile 3-((4-chlorophenyl){3-[1-(3,5-difluorophenyl)-2,2-dimethylpropyl]azetidin-1-yl}methyl)benzonitrile 3-((1S)-1-{1-[(S)-(3-cyanophenyl)(4-cyanophenyl)methyl]azetidin-3-yl}-2-fluoro-2-methylpropyl)-5-fluorobenzonitrile 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile and 5-((4-chlorophenyl){3-[(1S)-1-(3,5-difluorophenyl)-2-fluoro-2-methylpropyl]azetidin-1-yl}methyl)thiophene-3-carbonitrile, as well as the pharmaceutically acceptable salts and solvates thereof, in combination with a pharmaceutically acceptable carrier.

Optical Isomers—Diastereomers—Geometric Isomers—Tautomers

Many of the compounds of formula I contain one or more asymmetric centers and thus occur as racemates and racemic mixtures, single enantiomers, diastereomeric mixtures and individual diastereomers. The present invention includes all such isomeric forms of the compounds, in pure form as well as in mixtures.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixtures thereof are encompassed with the compounds of Formula I.

Salts and Solvates

Salts and solvates of compounds of formula I are included in the present invention. The term "pharmaceutically acceptable salts" refers to salts prepared from pharmaceutically acceptable substantially non-toxic bases or acids including inorganic or organic bases and inorganic or organic acids, as well as salts that can be converted into pharmaceutically acceptable salts. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

Particularly preferred are citric, hydrobromic, hydrochloric, maleic, phosphoric, sulfuric, and tartaric acids.

Solvates as used herein refers to the compound of formula I or a salt thereof, in association with a solvent, such as water. Representative examples include hydrates, hemihydrates, trihydrates and the like.

References to the compounds of Formula I are intended to include the pharmaceutically acceptable salts and solvates.

This invention relates to a method of antagonizing or inhibiting the production or activity of glucagon, thereby reducing the rate of gluconeogenesis and glycogenolysis, and the concentration of glucose in plasma.

The compounds of formula I can be used in the manufacture of a medicament for the prophylactic or therapeutic treatment of disease states in mammals associated with elevated levels of glucose, comprised of combining the compound of formula I with the carrier materials to provide the medicament.

Dose Ranges

The prophylactic or therapeutic dose of a compound of formula I will, of course, vary with the nature or severity of the condition to be treated, the particular compound selected and its route of administration. It will also vary according to the age, weight and response of the individual patient. In general, the daily dose range lies within the range of from about 0.001 mg to about 100 mg per kg body weight, preferably about 0.01 mg to about 50 mg per kg, and more preferably 0.1 to 10 mg per kg, in single or divided doses. It may be necessary to use dosages outside of these limits in some cases. The terms "effective amount", "anti-diabetic effective amount" and the other terms appearing throughout the application addressing the amount of the compound to be used refer to the dosage ranges provided, taking into account any necessary variation outside of these ranges, as determined by the skilled physician.

Representative dosages of compounds of formula I, as well as the pharmaceutically acceptable salts and solvates thereof, for adults range from about 0.1 mg to about 1.0 g per day, preferably about 1 mg to about 500 mg, in single or divided doses. Representative dosages of compounds used in combination with the compounds of formula I are known, or the determination thereof is within the level of skill in the art, taking into account the description provided herein.

When intravenous or oral administration is employed, a representative dosage range is from about 0.001 mg to about 100 mg (preferably from 0.01 mg to about 10 mg) of a compound of Formula I per kg of body weight per day, and more preferably, about 0.1 mg to about 10 mg of a compound of formula I per kg of body weight per day.

When used in combination with other agents, the dosages noted above for the glucagon antagonist are provided along with the usual dose for the other medication. For example, when a DPP-IV inhibitor such as those disclosed in U.S. Pat. No. 6,699,871B1, is included, the DPP-IV inhibitor can be used in an amount ranging from about 1.0 mg to as high as about 1000 mg, preferably about 2.5 mg to about 250 mg, and in particular, about 50 mg or about 100 mg administered in single daily doses or in divided doses as appropriate. Similarly, when the glucagon antagonist is used in combination with a CB1 antagonist/inverse agonist, the CB1 antagonist/inverse agonist can be used in an amount ranging from as low as about 0.1 mg to as high as about 1000 mg, more particularly, in an amount ranging from about 1.0 mg to about 100 mg, and even more particularly, in an amount from about 1.0 mg to about 10 mg, administered in single daily doses or in divided doses as appropriate. Examples of doses of CB1 antagonist/inverse agonist include 1 mg, 2 mg, 3 mg, 4 mg, 5 mg, 6 mg, 7 mg, 8 mg, 9 mg and 10 mg.

Pharmaceutical Compositions

As mentioned above, the pharmaceutical composition comprises a compound of Formula I or a pharmaceutically acceptable salt or solvate thereof and a pharmaceutically acceptable carrier. The term "composition" encompasses a product comprising the active and inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients. Preferably the composition is comprised of a compound of formula I in an amount that is effective to treat, prevent or delay the onset of type 2 diabetes mellitus, in combination with the pharmaceutically acceptable carrier.

Any suitable route of administration may be employed for providing a mammal, especially a human with an effective dosage of a compound of the present invention. For example, oral, rectal, topical, parenteral, ocular, pulmonary, nasal, and the like may be employed. Examples of dosage forms include tablets, troches, dispersions, suspensions, solutions, capsules, creams, ointments, aerosols and the like, with oral tablets being preferred.

In preparing oral compositions, any of the usual pharmaceutical media may be employed, such as, for example, water, glycols, oils, alcohols, flavoring agents, preservatives, coloring agents and the like, in the case of oral liquids, e.g., suspensions, elixirs and solutions; or carriers such as starches, sugars, microcrystalline cellulose, diluents, granulating agents, lubricants, binders, disintegrating agents and the like in the case of oral solids, e.g., powders, capsules and tablets. Solid oral preparations are preferred. Because of their ease of administration, tablets and capsules represent the most advantageous oral dosage unit forms. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any acceptable pharmaceutical process. All such methods include the step of combining the active ingredient(s) with the carrier components. In general, the compositions are prepared by uniformly and intimately admixing the active ingredient(s) with a liquid or finely divided solid carrier component, and then, if necessary, manipulating the blend into the desired product form. For example, a tablet may be prepared by compression or molding. Compressed tablets may be prepared by compressing free-flowing powder or granules, containing the active(s) optionally mixed with one or more excipients, e.g., binders, lubricants, diluents, surfactants and dispersants. Molded tablets may be made by molding a mixture of the powdered compound moistened with an inert liquid. Desirably, each tablet may contain, for example, from about 0.1 mg to about 1.0 g of the active ingredient and each cachet or capsule contains from about 0.1 mg to about 500 mg of the active ingredient.

The following are examples of pharmaceutical dosage forms containing a compound of Formula I:

| Injectable Suspension (im.) | mg/mL | Tablet | Mg/tablet |
|---|---|---|---|
| Compound of Formula 1 | 10.0 | Compound of Formula 1 | 25.0 |
| Methylcellulose | 5.0 | Microcrystalline Cellulose | 415 |
| Tween 80 | 0.5 | Povidone | 14.0 |
| Benzyl alcohol | 9.0 | Pregelatinized Starch | 4.35 |
| Benzalkonium chloride | 1.0 | Magnesium Stearate | 2.5 |
| Water for injection | t.d. 1.0 mL | Total | 500 mg |

| Capsule | mg/capsule | Aerosol | Per Canister |
|---|---|---|---|
| Compound of Formula 1 | 25.0 | Compound of Formula 1 | 250 mg |
| Lactose | 735 | Lecithin, NF Liq. Conc. | 1.2 mg |
| Mg Stearate | 1.5 | Trichloromethane, NF | 4.025 g |
| Total | 600 mg | Dichlorodifluoromethane, NF | 12.15 g |

Combination Therapy

As previously described, the compounds of Formula I may be used in combination with other drugs that are used in the treatment/prevention/delaying the onset of type 2 diabetes mellitus, as well as other diseases and conditions described herein, for which compounds of Formula I are useful. Other drugs may be administered, by a route and in an amount commonly used, contemporaneously or sequentially with a compound of Formula I. When a compound of Formula I is used contemporaneously with one or more other drugs, a combination pharmaceutical composition containing such other drugs in addition to the compound of Formula I is preferred. Accordingly, the pharmaceutical compositions of the present invention include those that alternatively contain one or more other active ingredients, in addition to a compound of Formula I. Examples of other active ingredients that may be combined with a compound of Formula I, either administered separately or in the same pharmaceutical compositions, include, but are not limited to: (a) biguanides (e.g., buformin, metformin, phenformin), (b) PPAR agonists (e.g., troglitazone, pioglitazone, rosiglitazone), (c) insulin, (d) somatostatin, (e) alpha-glucosidase inhibitors (e.g., voglibose, miglitol, acarbose), (f) DPP-IV inhibitors, such as those disclosed in U.S. Pat. No. 6,699,871B1 granted on Mar. 2, 2004 (g) LXR modulators and (h) insulin secretagogues (e.g., acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide), and CB1 inhibitors, such as rimonabant and those compounds disclosed in WO03/077847A2 published on Sep. 25, 2003 and in WO05/000809 A1 published on Jan. 6, 2005.

The weight ratio of the compound of the Formula I to the second active ingredient may be varied within wide limits and depends upon the effective dose of each active ingredient. Generally, an effective dose of each will be used. Thus, for example, when a compound of the Formula I is combined with a PPAR agonist the weight ratio of the compound of the Formula I to the PPAR agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

For combination products, the compound of formula I may be combined with any other active ingredients and then added to the carrier ingredients; alternatively the order of mixing may be varied.

Examples of pharmaceutical combination compositions include: (1) a compound according to formula I, (2) a compound selected from the group consisting of: (a) DPP-IV inhibitors; (b) insulin sensitizers selected from the group consisting of (i) PPAR agonists and (ii) biguanides; (c) insulin and insulin mimetics; (d) sulfonylureas and other insulin secretagogues; (e) a-glucosidase inhibitors; (f) CB1 receptor antagonists/inverse agonists; (g) GLP-1, GLP-1 mimetics, and GLP-1 receptor agonists; (h) GIP, GIP mimetics, and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid or a salt thereof, (iv) PPAR alpha agonists, (v) PPAR alpha/gamma dual agonists, (vi) inhibitors of cholesterol absorption, (vii) acyl CoA: cholesterol acyltransferase inhibitors, (viii) anti-oxidants and (ix) LXR modulators; (k) PPAR delta agonists; (l) antiobesity compounds; (m) an ileal bile acid transporter inhibitor; (n) anti-inflammatory agents other than glucocorticoids; and (o) protein tyrosine phosphatase-1B (PTP-1B) inhibitors; (p) CB1 antagonist/inverse agonists and (3) a pharmaceutically acceptable carrier.

The compounds of formula I can be synthesized in accordance with the general schemes provided below, taking into account the specific examples that are provided. Throughout the synthesis schemes, abbreviations are used with the following meanings unless otherwise indicated:

| | |
|---|---|
| Bu = butyl, t-Bu = t-butyl | Bn and Bnzl = benzyl |
| BOC, Boc = t-butyloxycarbonyl | CBZ, Cbz = Benzyloxycarbonyl |
| COD = cyclooctadiene | DCM = dichloromethane |
| CDI = carbonyl diimidazole | DIAD = diisopropylazodicarboxylate |
| DCC = Dicyclohexylcarbodiimide | DMAP = 4-Dimethylaminopyridine |
| DIEA = diisopropylethylamine | DMPU = 1,3-dimethyl-3,4,5,6-tetrahydro-2(1H)pyrimidinone |
| DMAC = dimethylacetamide | EtOH = ethanol |
| DMF = N,N-dimethylformamide | FAB-mass spectrum = Fast atom bombardment-mass spectroscopy |
| EtOAc = ethyl acetate | HPLC = High pressure liquid chromatography |
| eq. = equivalent(s) | LAH = Lithium aluminum hydride |
| HOAc = acetic acid | MTBE = methyl t-butyl ether |
| HOBT, HOBt = Hydroxybenztriazole | MeCN, $CH_3CN$ = acetonitrile |
| MeOH = methanol | TFA = Trifluoroacetic acid |
| Me = methyl | $NMe_2$ = dimethylamino |
| PBS = phosphate buffer saline | 2ClPh = 2-chlorophenyl |
| Ph = phenyl | IPA = isopropanol |
| THF = Tetrahydrofuran | Py, Pyr = pyridyl |
| $C_6H_{11}$ = cyclohexyl | iPAc = isopropyl acetate |
| iPr = isopropyl | RT = room temperature |
| 2,4-diClPh = 2,4-dichlorophenyl | |

Compounds of the present invention may be prepared according to the methodology outlined in the following general synthetic schemes.

In one embodiment of the present invention, the compounds may be prepared from intermediate II (vide infra),

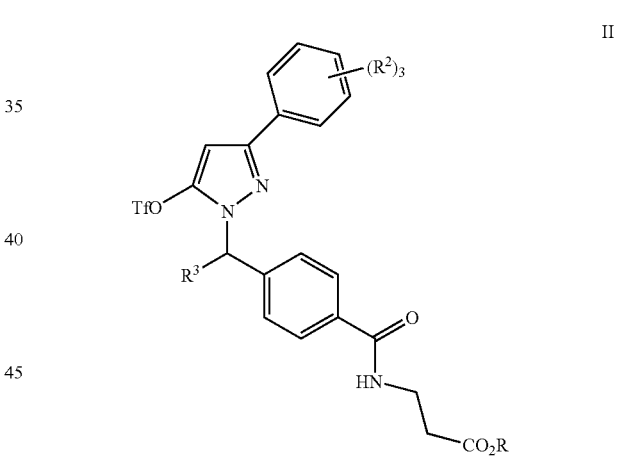

II where $R^2$ and $R^3$ are as defined above and R represents an alkyl group.

Compounds II, can in turn be prepared by condensation of the β-ketoester 1 and benzyl hydrazine 2. Compounds such as 1 are commercially available, known in the literature or may be conveniently prepared by a variety of methods familiar to those skilled in the art. One route is illustrated in Scheme I and described in Clay et al., *Synthesis*, 1993, 290. Acid chloride 3, which may be commercially available or readily prepared from the corresponding carboxylic acid by treatment with thionyl chloride at elevated temperatures or oxalyl chloride in a solvent such as methylene chloride in the presence of a catalytic amount of dimethylformamide (DMF) at room temperature, is treated with potassium ethyl malonate and magnesium chloride in the presence a base such as triethylamine in an aprotic solvent such as ethyl acetate for 1-16 h to give ketoester 1.

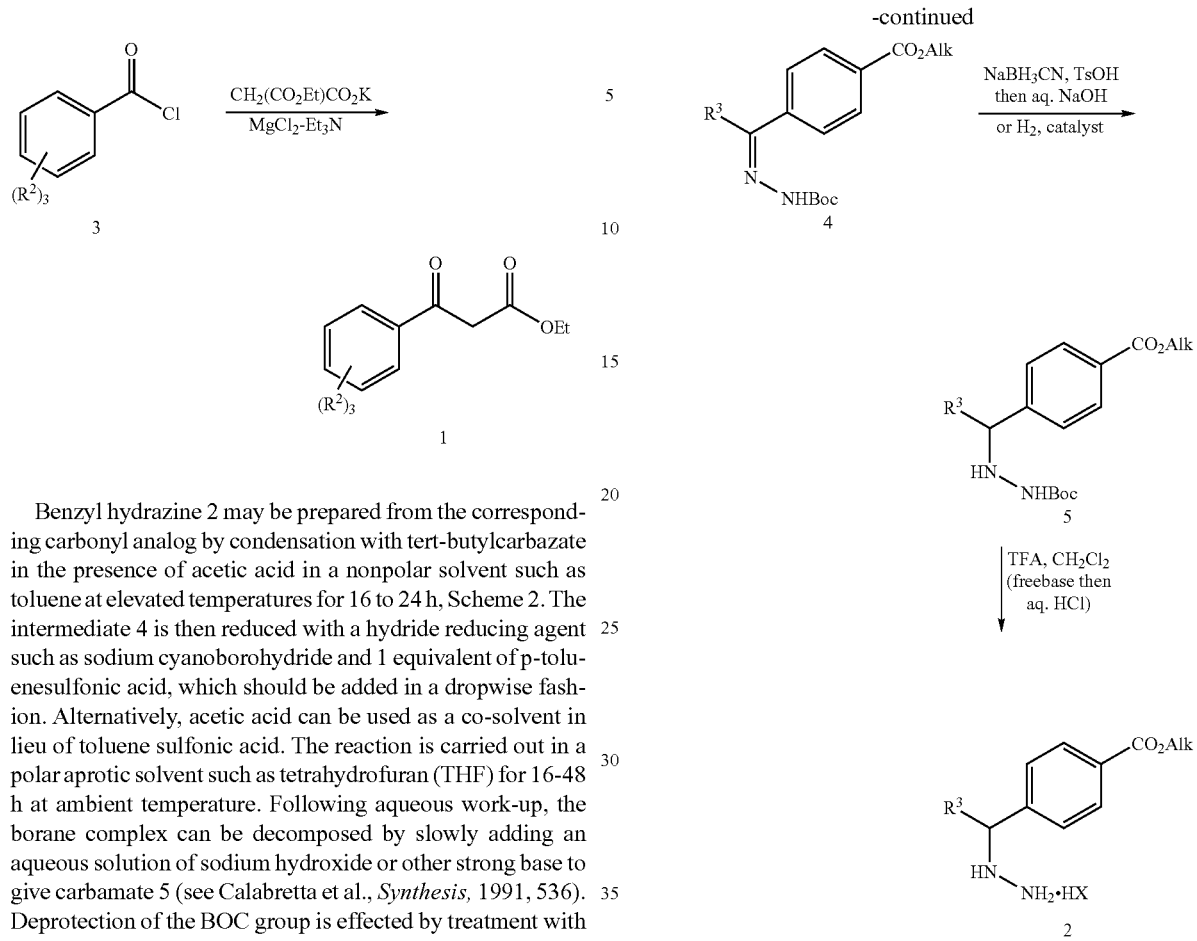

Benzyl hydrazine 2 may be prepared from the corresponding carbonyl analog by condensation with tert-butylcarbazate in the presence of acetic acid in a nonpolar solvent such as toluene at elevated temperatures for 16 to 24 h, Scheme 2. The intermediate 4 is then reduced with a hydride reducing agent such as sodium cyanoborohydride and 1 equivalent of p-toluenesulfonic acid, which should be added in a dropwise fashion. Alternatively, acetic acid can be used as a co-solvent in lieu of toluene sulfonic acid. The reaction is carried out in a polar aprotic solvent such as tetrahydrofuran (THF) for 16-48 h at ambient temperature. Following aqueous work-up, the borane complex can be decomposed by slowly adding an aqueous solution of sodium hydroxide or other strong base to give carbamate 5 (see Calabretta et al., *Synthesis*, 1991, 536). Deprotection of the BOC group is effected by treatment with an acid such as trifluoroacetic acid in methylene chloride at ambient temperature for 0.25-2 h. The reaction can be performed with or without the addition of triisopropylsilane. The hydrazine 2 can either be used as its trifluoroacetate salt directly from the deprotection, or the free-base can be prepared and the material isolated as the hydrochloride salt by addition of aqueous hydrochloric acid and evaporation of the solvent. In the case ($R^3$ not H) that intermediate 5 contains a chiral center, the enantiomers can be resolved at this point by chromatography using a homochiral stationary phase. Alternatively, hydrazone 4 can be directly reduced with hydrogen and a chiral catalyst such as a rhodium DuPHOS complex as described in Burk et al., *Tetrahedron*, 1994, 50, 4399. The solvent used for the reaction was generally an alcohol such as 2-propanol and elevated hydrogen pressure was used. This reaction would give material of enriched enantioselectivity which could be further purified by chiral chromatography as described above.

Scheme 2

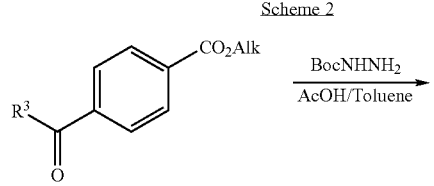

Condensation of the β-ketoester 1 and benzyl hydrazine 2 described in Scheme 3 is carried out by heating the two components in a solvent such as acetic acid or acetonitrile for 1-8 h to give the pyrazolone 6. Elaboration at this point to β-alanine ester 7 can be achieved by saponification of the ester 6 using a base such as aqueous lithium or sodium hydroxide in a polar solvent such as tetrahydrofuran, dioxane, methanol, ethanol or a mixture of similar solvents. Coupling of the beta alanine ester 8 is then achieved using 1-ethyl-3-(3-dimethylaminopropyl)-carbodiimide (EDC) and 1-hydroxybenzotriazole (HOBt) or benzotriazole-1-yloxytrispyrrolidinophosphonium hexafluorophosphate (PyBOP) and a base, generally diisopropylethylamine, in a solvent such as N,N-dimethylformamide (DMF) or methylene chloride for 3 to 48 hours at ambient temperature to yield the compound 7. Pyrazolone 7 is then treated with triflic anhydride in a polar aprotic solvent such as THF in the presence of a base such as triethylamine at −78° C. to room temperature to afford the intermediate II. The product is purified from unwanted side products by recrystallization, trituration, preparative thin layer chromatography, flash chromatography on silica gel as described by W. C. Still et al, *J. Org. Chem.*, 43, 2923, (1978), or HPLC. Purification of intermediates is achieved in the same manner. If the intermediate II is racemic (i.e., $R^3$ is not hydrogen), the compound can be resolved via chiral hplc using either normal phase or supercritical fluid conditions.

Scheme 3

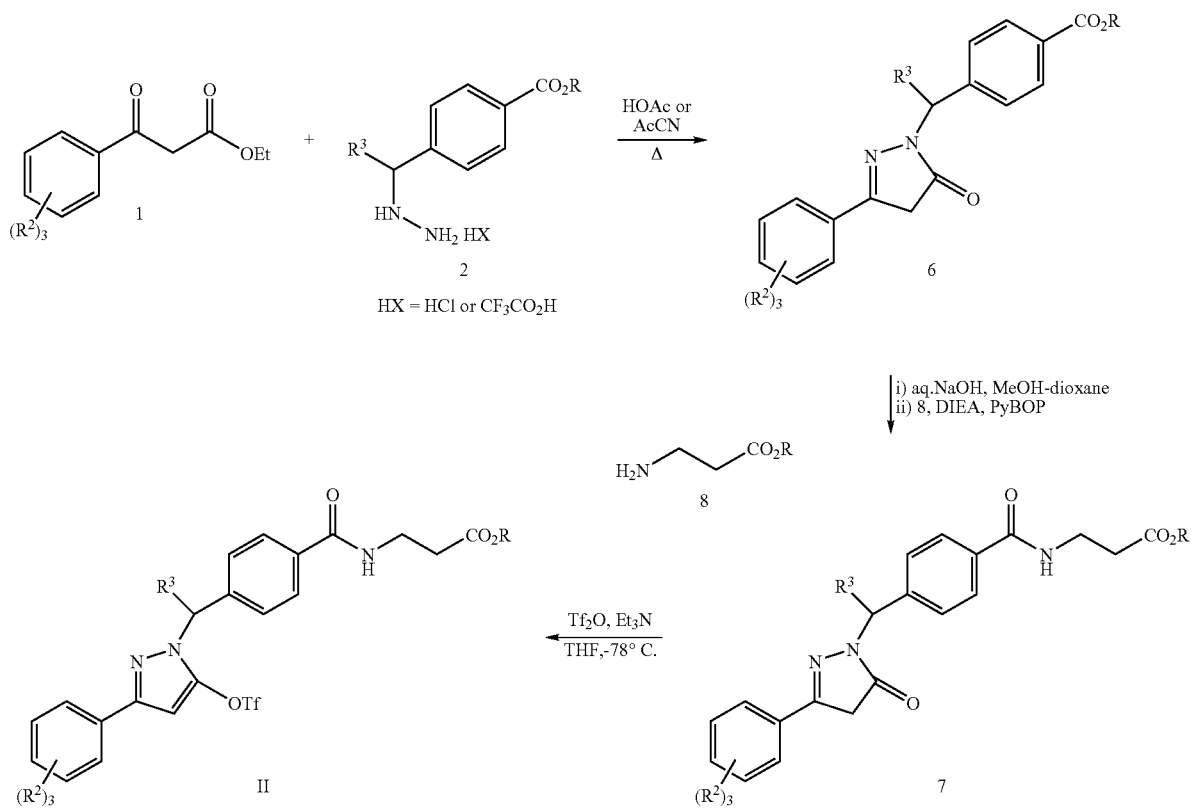

Final products I can then be prepared by coupling of intermediate II with an appropriate napthyl boronic acid 9. These compounds are commercially available, or can be prepared from commercial materials. One such route is illustrated in Scheme 4, tricyclic intermediate 10 is prepared according to Schlosser et al., *Eur. J. Org. Chem.,* 2001, 3991. This can then be aromatized by treatment with sodium iodide in an aprotic solvent such as acetonitrile followed by addition of trimethylsilylchloride. The reaction is stirred at ambient temperature for 1 to 5 h to give bromide 11. This can then be converted to the boronic acid by treatment with bis(pinacolato)diboron, potassium acetate and a palladium catalyst such as palladium II chloride and a ligand such as diphenyl phosphino ferrocene (dppf). The reaction is heated in a polar aprotic solvent such as DMSO for 1-5 h, followed by cleavage of the boronate ester by treatment with dilute acid such as hydrochloric acid in a solvent such as a cetone for a prolonged time. An alternative route to the boronic acid involves treatment of the naphthyl halide 11 with a strong base such as butyl lithium in a polar aprotic solvent such as THF at low temperatures followed by addition of a trialkyl borate such as trimethyl borate. The reaction is stirred a further 1-5 h with warming to ambient temperature, followed by quenching with dilute acid such as dilute hydrochloric acid prior to isolation of the intermediate 9.

Scheme 4

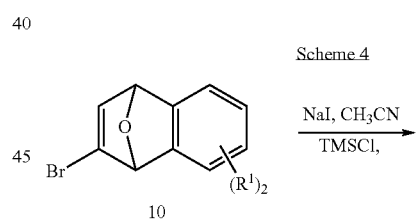

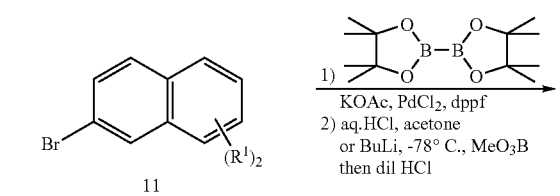

-continued

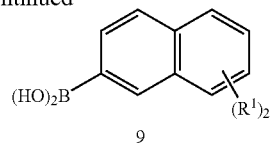

1) II, Pd(PPh₃)₄ DME, ET₃N, Δ
2) TFa/DCM or aq. NaOH/LiOH

I

The aryl triflate II can be coupled with boronic acid 9 using a palladium catalyst such as palladium 2-(di-$^t$butylphosphino)biphenyl or triphenylphosphine. The solvent is generally either dimethoxyethane (DME), ethanol or toluene, and triethylamine, cesium or sodium carbonate or potassium fluoride is also added to the reaction, which may also contain water and is performed at elevated temperatures and may be carried out in a microwave reactor (see Wang et al., *Tet. Lett.*, 2000, 41, 4713 for related cross-coupling reactions). Removal of the ester when R represents Me or Et is accomplished by saponification using a base such as aqueous lithium or sodium hydroxide in a polar solvent such as tetrahydrofuran, methanol, ethanol or a mixture of similar solvents. When R is a tert-butyl ester it is most conveniently removed by treatment with trifluoroacetic acid in methylene chloride for 0.5-3 h at ambient temperature. The product is purified from unwanted side products by recrystallization, trituration, preparative thin layer chromatography, flash chromatography on silica gel as described by W. C. Still et al, *J. Org. Chem.*, 43, 2923, (1978), or HPLC. Purification of intermediates is achieved in the same manner. In some cases, the product from the reactions described in Scheme 4 will be further modified. These manipulations may include, but are not limited to substitution, reduction, oxidation, alkylation, acylation, and hydrolysis reactions, which are commonly known to those skilled in the art.

An alternate route to the compounds (I) involves preparation of intermediate III (vide infra),

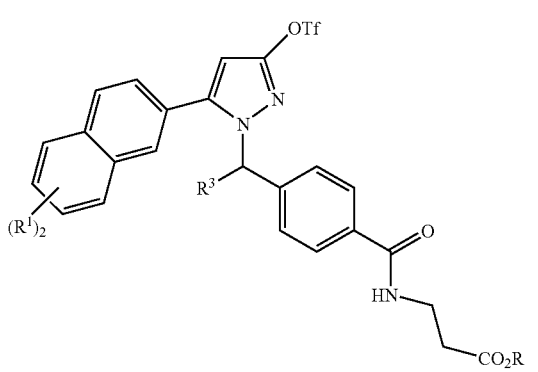

III where $R^1$ and $R^3$ are as defined above and R represents an alkyl group.

Compounds of formula III, can in turn be prepared by condensation of the β-ketoester 12 and hydrazine. Compounds such as 12 may be conveniently prepared by a variety of methods familiar to those skilled in the art. One route is illustrated in Scheme 5. Acid chloride 13, which may be commercially available or readily prepared from the corresponding carboxylic acid by treatment with thionyl chloride at elevated temperatures or oxalyl chloride in a solvent such as methylene chloride in the presence of a catalytic amount of dimethylformamide (DMF) at room temperature, is treated with potassium ethyl malonate and magnesium chloride in the presence a base such as triethylamine in an aprotic solvent such as ethyl acetate for 1-16 h to give ketoester 12. Condensation of the β-ketoester 12 and hydrazine is carried out by heating the two components in a solvent such as acetic acid or acetonitrile for 1-8 h to give the pyrazolone 13-1. Pyrazolone 13-1 is then treated with triflic anhydride in a polar aprotic solvent such as THF in the presence of a base such as triethylamine at −78° C. to room temperature to afford the triflate 14.

Scheme 5

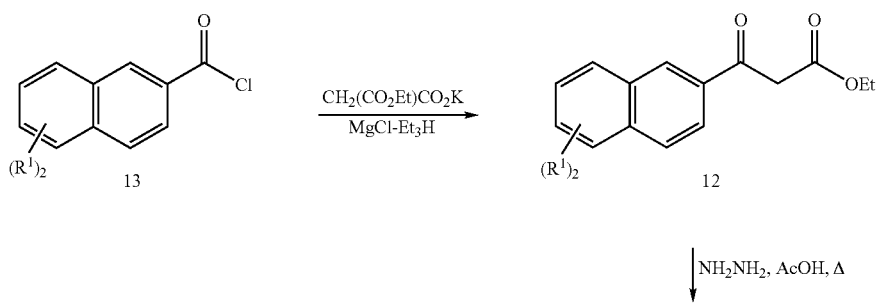

NH₂NH₂, AcOH, Δ

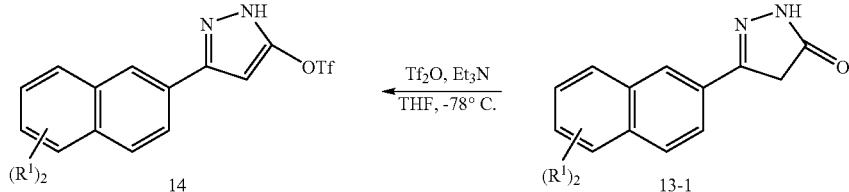

This is then alkylated with benzylic alcohol 15 which is prepared from a carbonyl derivative 16, by saponification of the ester using a base such as aqueous lithium or sodium hydroxide in a polar solvent such as tetrahydrofuran, dioxane, methanol, ethanol or a mixture of similar solvents. Coupling of the beta alanine derivative 8 is then achieved using 1-ethyl-3-(3-dimethylaminopropyl)-carbodiimide (EDC) and 1-hydroxybenzotriazole (HOBt) or benzotriazole-1-yloxytrispyrrolidinophosphonium hexafluorophosphate (PyBOP) and a base, generally diisopropylethylamine, in a solvent such as N,N-dimethylformamide (DMF) or methylene chloride for 3 to 48 hours at ambient temperature. Reduction of the ketone moiety to alcohol 15 is achieved using a hydride reducing agent such as sodium borohydride in a polar aprotic solvent such as methanol.

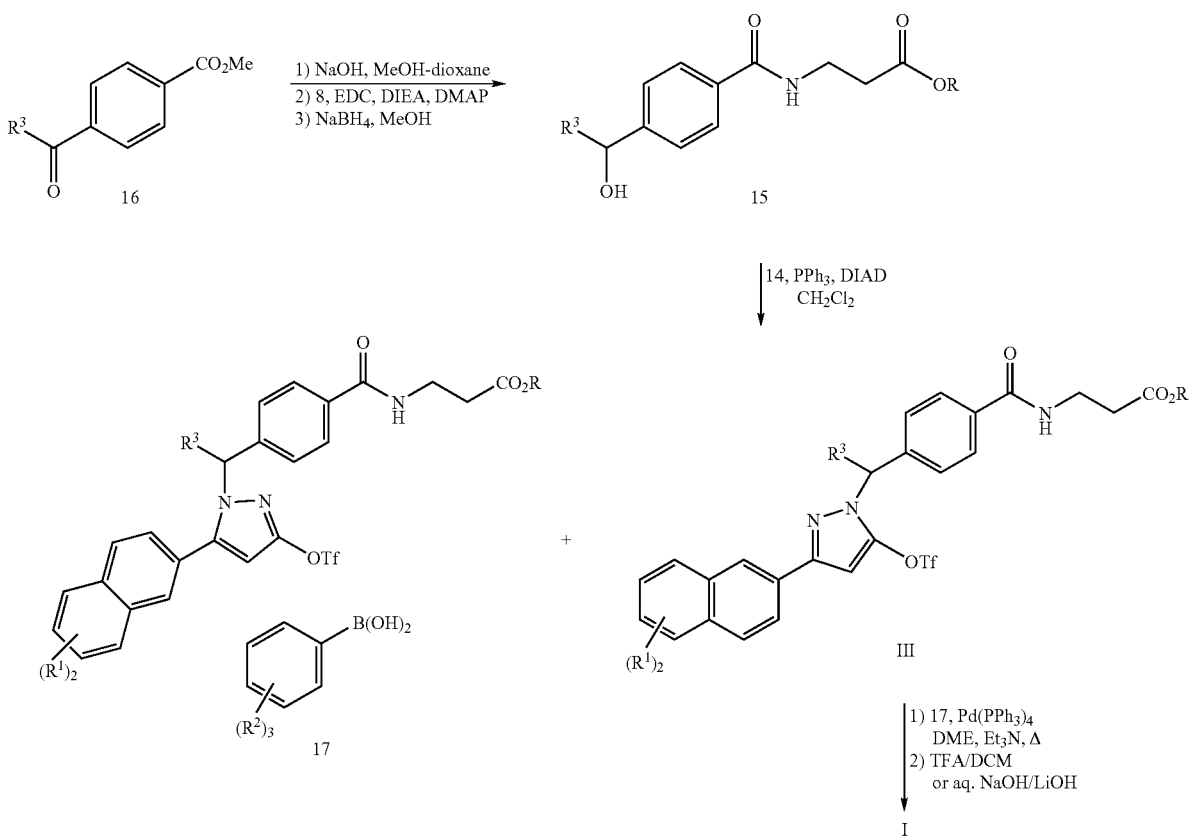

Alcohol 15 is coupled to triflate 14 to give intermediate III by treatment with a coupling reagent such as diisopropylazodicarboxylate (DIAD) and a trialkylphosphine such as triphenylphosphine in a non polar aprotic solvent such as methylene chloride for 0.5-6 h at ambient temperature. In some cases mixtures of regioisomers are formed and these can be separated as the compound is purified from unwanted side products by recrystallization, trituration, preparative thin layer chromatography, flash chromatography on silica gel as described by W. C. Still et al, *J. Org. Chem.*, 43, 2923, (1978), or HPLC. Purification of intermediates is achieved in the same manner. Final products I can then be prepared by coupling of intermediate III with an appropriate aryl boronic acid 17. In some cases these compounds are commercially available, in others they can be prepared from commercial materials by someone skilled in the art, vide supra. The coupling is achieved using a palladium catalyst such as palladium 2-(di-<sup>t</sup>butylphosphino)biphenyl or triphenylphosphine. The solvent is generally either dimethoxyethane, ethanol or toluene, and triethylamine, cesium or sodium carbonate or potassium fluoride is also added to the reaction, which may also contain water and is performed at elevated temperatures and may be carried out in a microwave reactor. Removal of the ester when R=Me or Et is accomplished by saponification using a base such as aqueous lithium or sodium hydroxide in a polar solvent such as tetrahydrofuran, dioxane, methanol, ethanol or a mixture of similar solvents. When R is a tert-butyl ester it is most conveniently removed by treatment with trifluoroacetic acid in methylene chloride for 0.5-3 h at ambient temperature. The product is purified from unwanted side products by recrystallization, trituration, preparative thin layer chromatography, flash chromatography on silica gel as described by W. C. Still et al, *J. Org. Chem.*, 43, 2923, (1978), or HPLC. Purification of intermediates is achieved in the same manner. If the product is racemic (ie $R^3$ is not hydrogen), then this compound can be resolved via chiral hplc using either normal phase or supercritical fluid conditions. In some cases, the product from the reactions described in Scheme 6 will be further modified. These manipulations may include, but are not limited to substitution, reduction, oxidation, alkylation, acylation, and hydrolysis reactions, which are commonly known to those skilled in the art.

Alternatively, modification of pyrazolone 6 can be carried out in a different order, Scheme 7. Pyrazolone 6 is treated with triflic anhydride ($Tf_2O$) in a polar aprotic solvent such as THF in the presence of a base such as triethylamine at −78° C. to room temperature to afford the intermediate 18. Palladium catalyzed coupling with an appropriate napthyl boronic acid 9 can be carried out at this point using a method analogous to that described above. Final elaboration can be achieved by saponification of the ester 19 using a base such as aqueous lithium or sodium hydroxide in a polar solvent such as tetrahydrofuran, dioxane, methanol, ethanol or a mixture of similar solvents. Coupling of the beta alanine 8 is then achieved using 1-ethyl-3-(3-dimethylaminopropyl)-carbodiimide (EDC) and 1-hydroxybenzotriazole (HOBt) or benzotriazole-1-yloxytrispyrrolidinophosphonium hexafluorophosphate (PyBOP) and a base, generally diisopropylethylamine, in a solvent such as N,N-dimethylformamide (DMF) or methylene chloride for 3 to 48 hours at ambient temperature to yield the ester of final product I. Removal of the ester when R=Me or Et is accomplished by saponification using a base such as aqueous lithium or sodium hydroxide in a polar solvent such as tetrahydrofuran, dioxane, methanol, ethanol or a mixture of similar solvents. When R is a tert-butyl ester it is most conveniently removed by treatment with trifluoroacetic acid in methylene chloride for 0.5-3 h at ambient temperature. The product is purified from unwanted side products by recrystallization, trituration, preparative thin layer chromatography, flash chromatography on silica gel as described by W. C. Still et al, *J. Org. Chem.*, 43, 2923, (1978), or HPLC. Purification of intermediates is achieved in the same manner. If compound I is racemic (ie $R^3$ is not hydrogen), then this compound can be resolved via chiral hplc using either normal phase or supercritical fluid conditions.

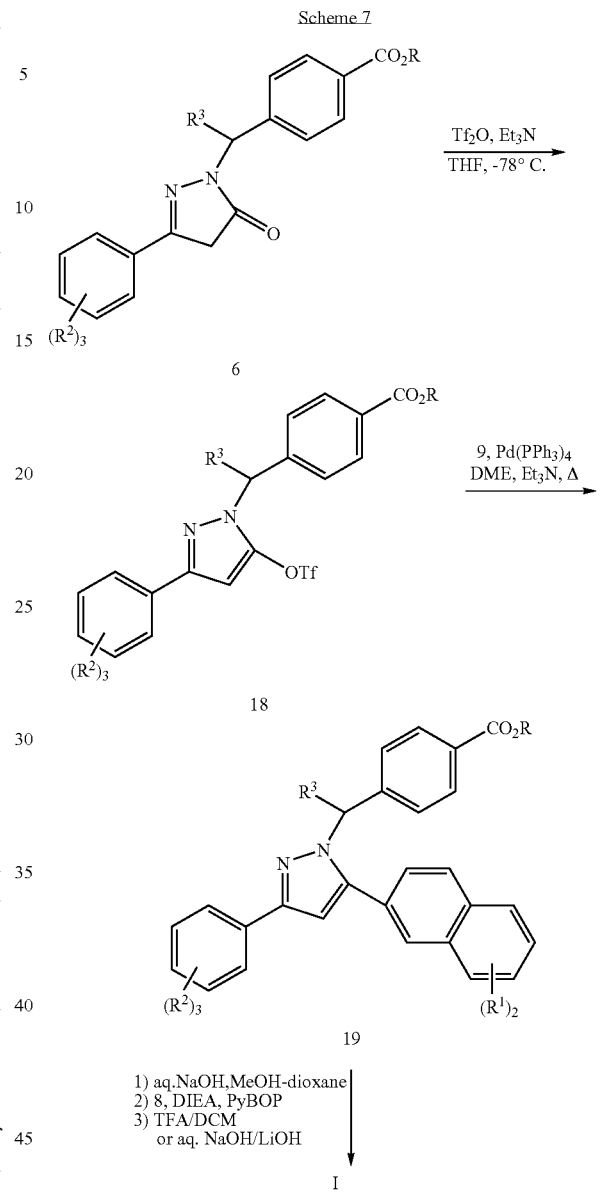

In some cases, the product I or the penultimate ester from the reactions described in the schemes above will be further modified. These manipulations may include, but are not limited to substitution, reduction, oxidation, alkylation, acylation, and hydrolysis reactions, which are commonly known to those skilled in the art. One such modification, illustrated here when one $R^2$ group is a protected phenol as in 20 (R is not hydrogen), involves release of the alcohol and subsequent etherification, Scheme 8. The hydroxyl group may be protected as a silyl ether, in which case a fluoride source, generally hydrofluoric acid or tetrabutylammonium fluoride is used for the reaction. Deprotection of a methoxy ether is routinely effected by treatment of the compound with boron tribromide in a solvent such as methylene chloride for a period of 1-16 h at ambient temperatures. Finally, if the alcohol is protected as an allyl ether, this is removed by treatment with dimethylbarbituric acid and a palladium catalyst, routinely tris(dibenzylideneacetone)dipalladium(0), with a ligand such as 1,4- bis-(diphenylphospino)butane in an aprotic solvent such as methylene chloride for 15 min to 2 h. See "Protective Groups in Organic Synthesis", Greene, published by Wiley and Sons.

skilled in the art as described in Katritsky et al., Advances in Heterocyclic Chemistry, Vol. 6, p 347-429. One route is illustrated in Scheme 9. Ester 22, which may be commercially

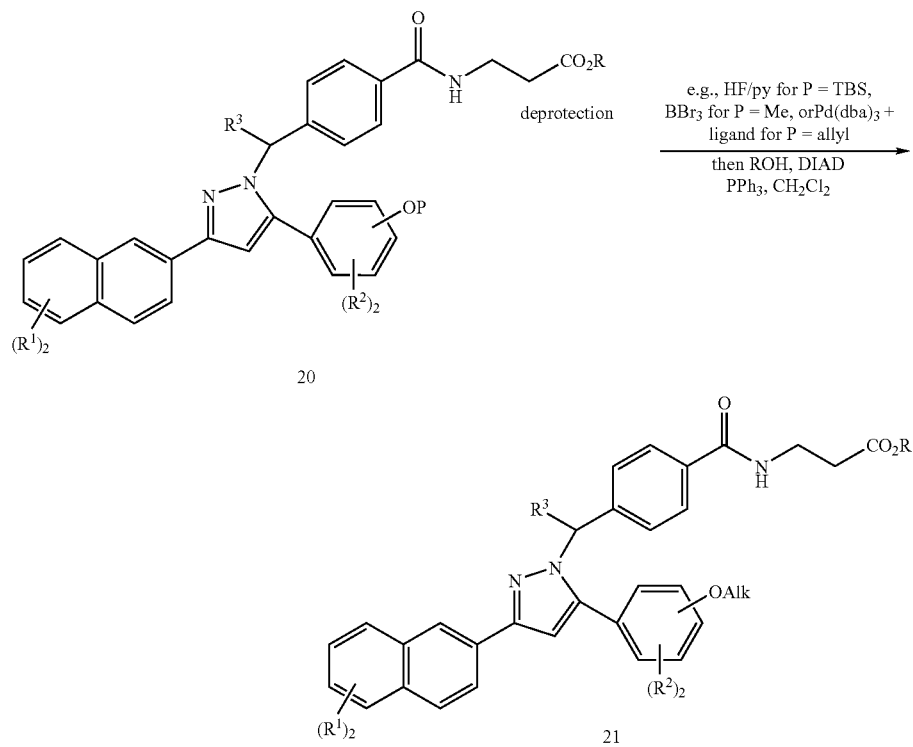

The free hydroxyl group may then be further modified to prepare ethers using an alcohol and coupling agent, such as diisopropylazodicarboxylate, and triphenylphosphine in a non polar solvent such as methylene chloride at temperatures of 0 to 40° C. for 1 to 16 h, Scheme 8. Intermediate 21 can then be converted to the desired products as previously described, vide supra.

An alternative approach to the compounds (I) involves alkylation of pyrazole IV (vide infra),

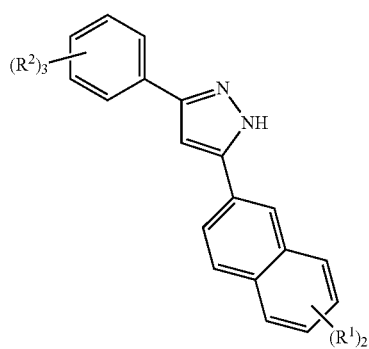

where $R^1$ and $R^2$ are as defined above.

Compounds IV are known in the literature or may be conveniently prepared by a variety of methods familiar to those available or readily prepared from the corresponding carboxylic acid by esterification using, for example, methanol or ethanol containing an acid such as sulphuric acid, is condensed with the anion of methyl ketone 23 to give diketone 24. The reaction is carried out using a base such as sodium hydride in a polar aprotic solvent such as tetrahydrofuran (THF) at 0 to 25° C. for 16 to 24 h, see March, Advanced Organic Chemistry, $3^{rd}$ Ed., pg 439 and ref. therein. Compounds such as 23 are commercially available or can be prepared by a variety of methods familiar to those skilled in the art. Diketone 24 is then condensed with hydrazine in a polar solvent such as methanol which may contain an acid such as acetic or hydrochloric acid, for 16 to 24 h at a temperature of 0 to 25° C.

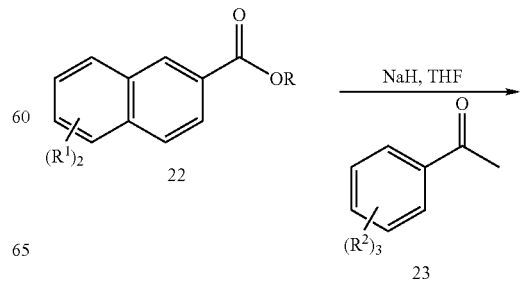

-continued

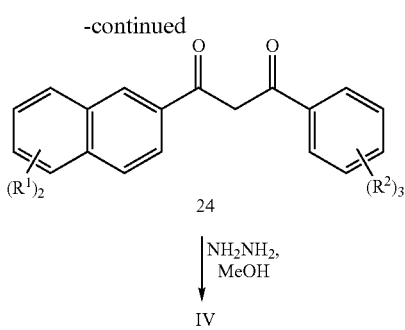
24

↓ NH₂NH₂, MeOH

IV

An alternate route to intermediate IV involves condensation of alkynyl ketone 25 with hydrazine as shown in Scheme 2 and described in Cabarrocas et. al., Tetrahedron Asymmetry, Vol. 11, pg 2483-2493, 2000 and references therein. This is generally carried out in a polar solvent such as DMF at temperatures of 0-25° C. for 16-24 h. Preparation of the intermediates 25 involves coupling of the alkyne 26 with the Weinreb amide of an appropriately functionalised carboxylic acid using a hindered base such as lithium diisopropylamide or butyl lithium in a polar aprotic solvent such as THF at −78° C. This reaction is described in detail in Tetrahedron Lett., Vol. 22, pg 3815, 1981. Alkynes 26 are either commercially available, or prepared from the corresponding halide and alkynyl magnesium iodide, see Negishi et. al., J. Org. Chem., Vol. 62, pg 8957-8960, 1997 and Org. Lett. Vol. 3, pg 3111-3113, 2001.

Scheme 10

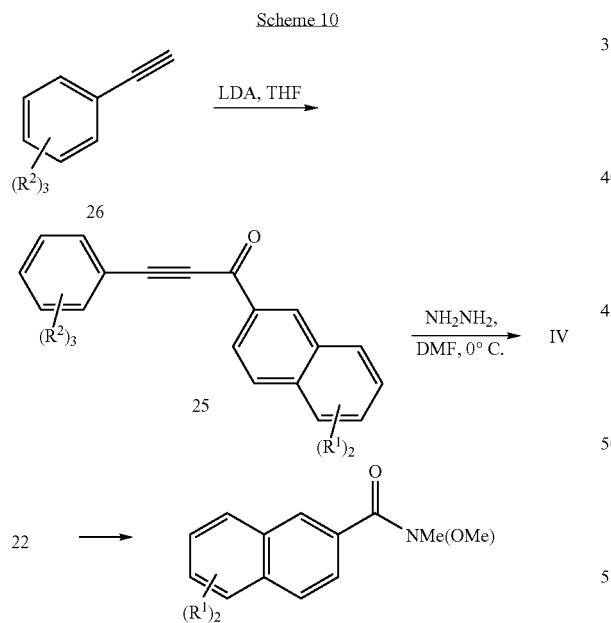

Intermediate IV can then be converted to compounds I as shown in Scheme 11. Alkylation of pyrazole IV with a 4-carboalkoxy benzylbromide can be achieved following deprotonation of the pyrazole with a base such as sodium hydride or cesium carbonate in a polar solvent, generally dimethyl formamide (DMF), at 0 to 25° C. for 3 to 24 h. Alternatively alkylation can be accomplished using alcohol 15 as described in Scheme 6, vide supra. In some cases mixtures of isomers will be formed. These are generally separable by recrystallization, trituration, preparative thin layer chromatography, flash chromatography on silica gel as described by W. C. Still et al, *J. Org. Chem.*, 43, 2923, (1978), or HPLC. Compounds purified by HPLC may be isolated as the corresponding salt. Conversion to final compounds is then achieved as described previously for ester 19. In some cases, the product from the reactions described in Scheme 3 will be further modified. These manipulations may include, but are not limited to substitution, reduction, oxidation, alkylation, acylation, and hydrolysis reactions, which are commonly known to those skilled in the art.

Scheme 11

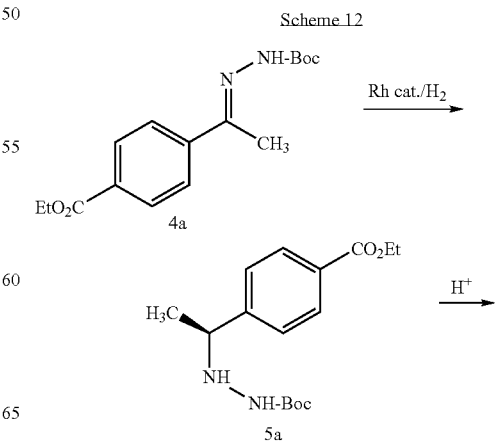

An alternate process describing an enantioselective route to compounds I is disclosed in Schemes 12 and 13.

Scheme 12

31

-continued

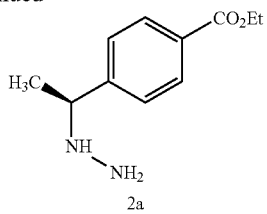

Compound 4a, prepared as described in Scheme 2, vide supra, is reduced with a rhodium catalyst typically Rh(COD)2BF4, in the presence of a ligand such as those shown below in isopropanol, methanol, or ethyl acetate to give 5a.

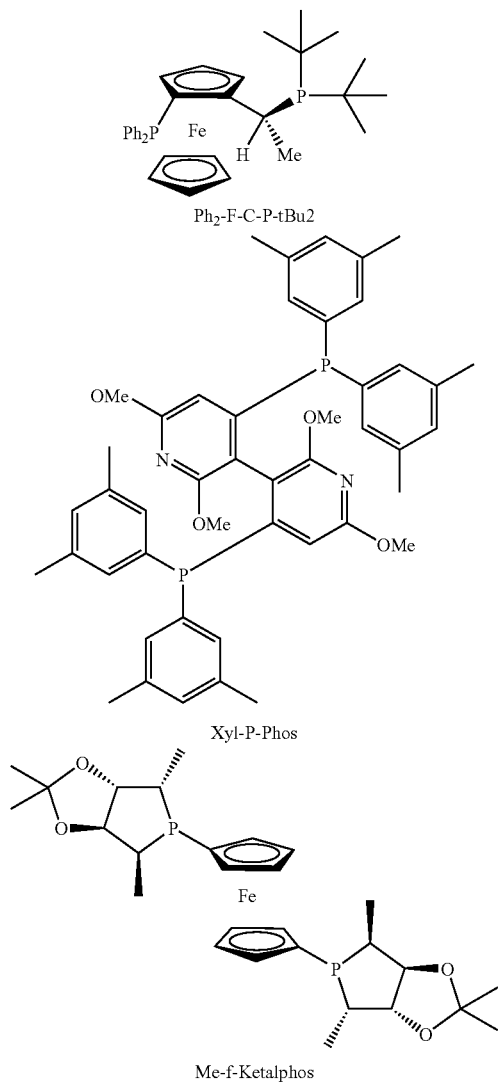

Ph2-F—C—P-tBu2 is a Josiphos catalyst which is disclosed in U.S. Pat. No. 6,777,567B2 (Solvias) and commercially available from Strem. Xyl-P-Phos is disclosed in U.S. Pat No. 5,886,182 (Synetix) and commercially available from Strem. Me-f-Ketal phos is similarly commercially available from Chiral Quest.

32

Deprotection of the BOC carbamate with acid, for example, benzene sulfonic acid, under substantially anhydrous conditions, provides the deprotected intermediate 2a.

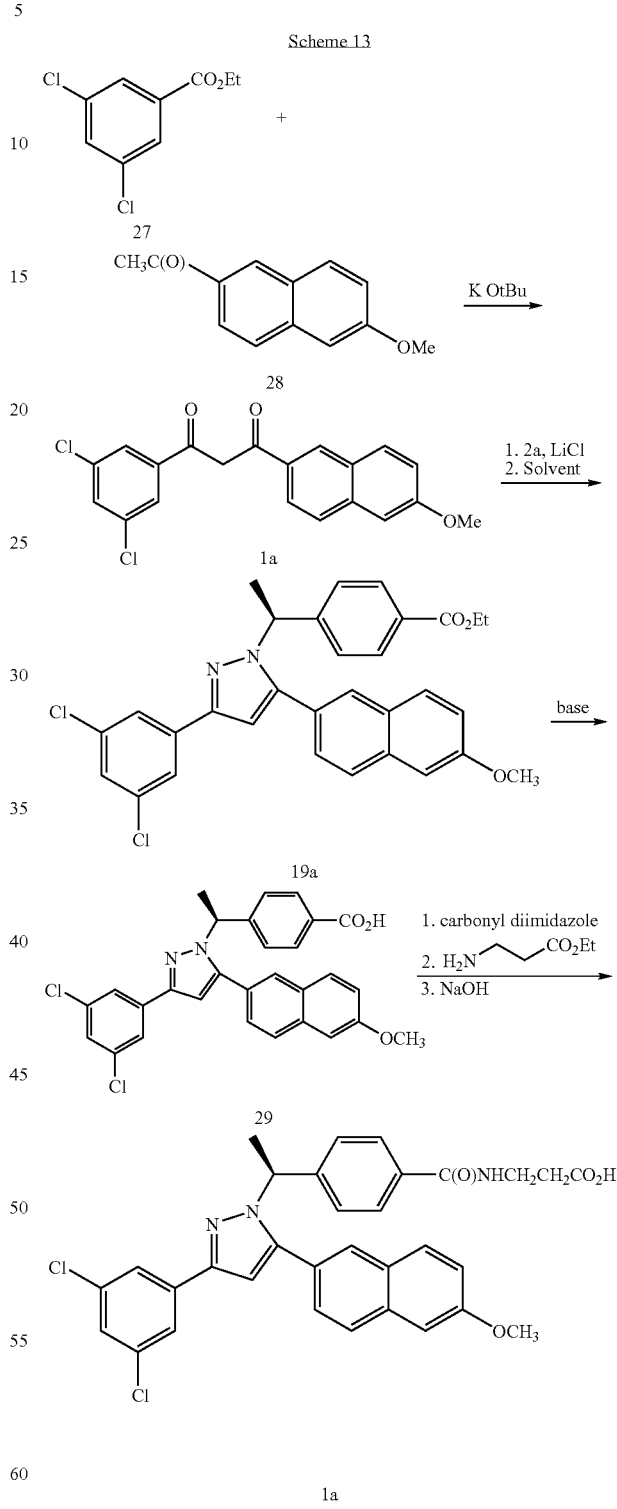

As shown above in Scheme 13, commercially available compounds 27 and 28, are condensed. Compound 28 is initially combined with a THF solution of potassium t-butoxide at reduced temperature, such as about −20° C. to about −5° C., to provide the enolate (not shown). Ester 27 is added with warming to about 20° C., producing the diketone 1a.

The diketone 1a is combined with compound 2a in a suitable solvent. Examples include EtOH, THF, HOAc, DMF, IPA, DMSO, DMAc, DMPU, MeCN, toluene and IPAc. Anhydrous LiCl is added to produce the desired ethyl ester intermediate 19 in a regioselective manner. Conversion of the ethyl ester to the pyrazole acid 29 is performed under hydrolytic conditions, for example, in a mixture of THF and MeOH, with NaOH at room temperature.

The acid product 29 can thereafter be isolated, via such methods as crystallization. By adjusting the pH to neutrality, unreacted material and side products can be precipitated and removed. Suitable crystallization solvents and solvent mixtures include MTBE/heptane and MeOF/water.

Compound 29 is thereafter reacted with beta alanine ethyl ester, HCl salt through formation of the acid chloride (not shown) which can be prepared using oxalyl or thionyl chloride, with subsequent removal of HCl via distillation. Alternatively, as shown in the schemes, amidation can be undertaken using CDI as an activating agent in a suitable solvent, e.g., THF at RT, followed by the addition of beta alanine in the form of the ethyl ester, HCl salt, at 50° C. Base, e.g., NaOH, is added at RT in a solvent such as MeOH to hydrolyze the ethyl ester. Acidification with HCl provides the product which can be extracted with iPAc, and isolated via further crystallization from acetonitrile/H$_2$O.

General experimental: Preparative HPLC was performed on a YMC-Pack Pro C18 column (150×20 mm i.d.) eluting at 20 mL/min with 0-100% acetonitrile in water (0.5% TFA).

The following examples are provided so that the invention might be more fully understood. They should not be construed as limiting the invention in any way.

Preparation of intermediates is described below, these are used in the synthesis of Examples 1-149.

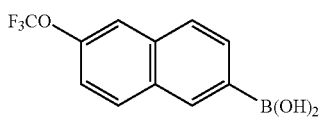

Intermediate A

Step A 2-Bromo-6-(trifluoromethoxy)naphthalene. 2-Bromo-6-(trifluoromethoxy)-1,4-dihydro-1,4-epoxynaphthalene [ref: Schlosser, M., Castgnetti, E., *Eur. J. Org. Chem.* 2001, 3991-3997] (1.09 g, 3.55 mmol) and NaI (1.6 g, 10.7 mmol) were dissolved in dry CH$_3$CN (40 ml), followed by addition of TMSCl (1.35 ml, 10.7 mmol). The reaction was stirred for 2.5 h, quenched with 5% Na$_2$SO$_3$, and extracted with ether. The ether solution was washed with 5% Na$_2$SO$_3$, brine, and dried over Na$_2$SO$_4$. The crude product was chromatographed (SiO$_2$, hexanes) to give 2-bromo-6-(trifluoromethoxy)naphthalene as white crystals. NMR (500 MHz, CDCl$_3$) δ: 7.36 (dd, J=2.6, 9.0 Hz, 1H); 7.60 (dd, J=2.0, 8.8 Hz, 1H); 7.63 (br s, 1H); 7.69 (d, J=8.8 Hz, 1H); 7.77 (d, J=9.0 Hz, 1H); 8.01 (d, J=2.0 Hz, 1H).

Step B [6-(Trifluoromethoxy)-2-naphthyl]boronic acid. 2-Bromo-6-(trifluoromethoxy)naphthalene (428 mg, 1.47 mmol), bis(pinacolato)diboron (410 mg, 1.62 mmol), and KOAc (433 mg, 4.41 mmol) were suspended in DMSO (12 ml). The mixture was de-oxygenated by vacuum-N$_2$ fill cycles, followed by the addition of catalyst PdCl$_2$(dppf) (30 mg, 2.5 mol %). The reaction was heated under N$_2$ atmosphere to 80° C. for 2 hr. The reaction was diluted with hexane (100 ml), washed with water, brine, and dried over Na$_2$SO$_4$.

After evaporation of solvent, the residue obtained was treated with acetone (20 ml) and 2N HCl (5 ml) for 24 h. The crude boronic acid was purified by reverse phase HPLC to give [6-(trifluoromethoxy)-2-naphthyl]boronic acid as a white powder. NMR (500 MHz, CDCl$_3$) δ: 7.44 (dd, J=2.3, 9.0 Hz, 1H); 7.74 (br s, 1H); 7.98 (d, J=8.2 Hz, 1H); 8.11 (d, J=9.0 Hz, 1H); 8.35 (dd, J=1.1 8.2 Hz, 1H); 8.85 (br s, 1H).

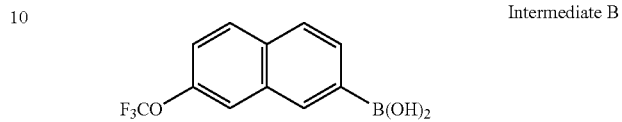

Intermediate B

Step A 2-Bromo-7-(trifluoromethoxy)naphthalene. This compound was prepared according to the conditions for 2-bromo-6-(trifluoromethoxy)naphthalene described above. NMR (500 MHz, CDCl$_3$) δ: 7.35 (dd, J=2.4, 8.9 Hz, 1H); 7.58 (br s, 1H); 7.59 (dd, J=2.0, 8.8 Hz, 1H); 7.73 (d, J=8.8 Hz, 1H); 7.84 (d, J=9.0 Hz, 1H); 8.00 (d, J=2.0 Hz, 1H).

Step B [7-(Trifluoromethoxy)-2-naphthyl]boronic acid. This compound was prepared according to the conditions for [6-(trifluoromethoxy)-2-naphthyl]boronic acid described above. NMR (500 MHz, CDCl$_3$) δ: 7.74 (dd, J=2.2, 8.9 Hz, 1H); 7.93 (br s, 1H); 7.97 (d, J=8.9 Hz, 1H); 8.02 (d, J=8.3 Hz, 1H); 8.34 (d, J=8.3 Hz, 1H); 8.85 (br s, 1H).

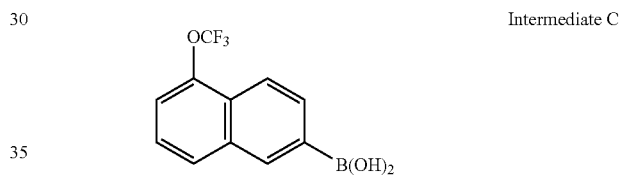

Intermediate C

Step A 2-Bromo-5-(trifluoromethoxy)naphthalene. This compound was prepared according to the conditions for 2-bromo-6-(trifluoromethoxy)naphthalene described above. NMR (500 MHz, CDCl$_3$) δ: 7.39 (pd, J=1.6, 7.8 Hz, 1H); 7.48 (t, J=8 Hz, 1H); 7.66 (dd, J=1.9, 9.0 Hz, 1H); 7.69 (d, J=8.3 Hz, 1H); 8.01 (d, J=9.0 Hz, 1H); 8.05 (d, J=1.9 Hz, 1H).

Step B [5-(Trifluoromethoxy)-2-naphthyl]boronic acid. This compound was prepared according to the conditions for [6-(trifluoromethoxy)-2-naphthyl]boronic acid described above. NMR (500 MHz, CDCl$_3$) δ: 7.51 (dd, J=1.4, 7.6 Hz, 1H); 7.55 (t, J=8 Hz, 1H); 8.02 (d, J=8.0 Hz, 1H); 8.29 (d, J=8.5 Hz, 1H); 8.40 (dd, J=1.1, 8.5 Hz, 1H); 8.86 (br s, 1H).

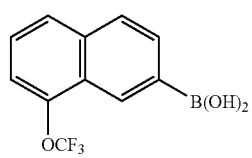

Intermediate D

Step A 2-Bromo-8-(trifluoromethoxy)naphthalene. This compound was prepared according to the conditions for 2-bromo-6-(trifluoromethoxy)naphthalene described above. NMR (500 MHz, CDCl$_3$) δ: 7.41 (dd, J=1.9, 7.7 Hz, 1H); 7.47 (t, J=8 Hz, 1H); 7.64 (dd, J=2.0, 8.8 Hz, 1H); 7.75 (d, J=8.7 Hz, 2H); 8.29 (d, J=1.9 Hz, 1H).

Step B [8-(Trifluoromethoxy)-2-naphthyl]boronic acid. This compound was prepared according to the conditions for

[6-(trifluoromethoxy)-2-naphthyl]boronic acid described above. NMR (500 MHz, CDCl$_3$) δ: 7.48 (d, J=7.6 Hz, 1H); 7.59 (t, J=7.9 Hz, 1H); 7.88 (d, J=8.2 Hz, 1H); 8.05 (d, J=8.2 Hz, 1H); 8.40 (dd, J=1.2, 8.2 Hz, 1H); 8.18 (s, 1H).

Intermediate E

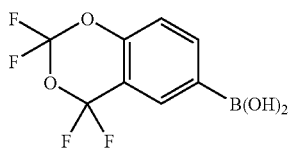

(2,2,4,4-Tetrafluoro-4H-1,3-benzodioxin-6-yl)boronic acid. This compound was prepared according to the conditions for [6-(trifluoromethoxy)-2-naphthyl]boronic acid described above. NMR (500 MHz, CDCl$_3$) δ: 7.32 (d, J=8.3 Hz, 1H); 8.43 (d, J=8.3 Hz, 1H); 8.44 (s, 1H).

Intermediate F

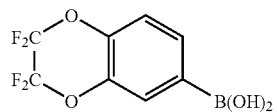

(2,2,3,3-Tetrafluoro-2,3-dihydro-1,4-benzodioxin-6-yl) boronic acid. This compound was prepared according to the conditions for [6-(trifluoromethoxy)-2-naphthyl]boronic acid described above. NMR (500 MHz, CDCl$_3$) δ: 7.30 (d, J=8.2 Hz, 1H); 7.96 (d, J=1.4 Hz, 1H); 8.01 (dd, J=1.4 8.2 Hz, 1H).

Intermediate G

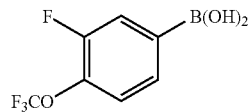

[3-Fluoro-4-(trifluoromethoxy)phenyl]boronic acid. A solution of 4-bromo-2-fluoro-1-(trifluoromethoxy)benzene (1.0 g, 3.9 mmol) in THF (5 ml) was added slowly to n-BuLi (3.0 ml, 1.6M in hexane) in THF (5 ml) at −78° C. After 20 min, trimethyl borate (1.4 ml, 12 mmol) was added; the mixture was stirred at −78° C. for 2 hr. The cooling bath was removed, the reaction was allowed to warm up to room temperature (1-2 h). The reaction was then quenched with 2N HCl (10 ml) and stirred overnight. Solvent was removed under reduced pressure, and the residue dissolved in CH$_3$CN—H$_2$O-dioxane. Chromatography by reverse phase HPLC gave, after lyophilization, [3-fluoro-4-(trifluoromethoxy)phenyl]boronic acid as a fine powder. NMR (500 MHz, CDCl$_3$) δ: 7.47 (m, 1H); 7.99 (m, 2H).

Intermediate H

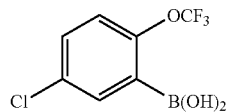

[5-Chloro-2-(trifluoromethoxy)phenyl]boronic acid. A solution of n-BuLi (17 ml, 1.6M in hexane) was added via syringe pump in one hour to a THF (50 ml) solution of 1-chloro-4-(trifluoromethoxy)benzene (5.0 g, 25.5 mmol) and diisopropylamine (0.42 ml, 3 mmol) at −78° C. After 20 min, trimethyl borate (8 ml, 70 mmol) was added, the mixture was stirred at −78° C., for 2 hr. The cooling bath was removed, the reaction was allowed to warm up to room temperature (1-2 h). The reaction was then quenched with 2N HCl (40 ml) and stirred overnight. Solvent was removed under reduced pressure, and the residue dissolved in CH$_3$CN—H$_2$O-dioxane. Chromatography by reverse phase HPLC gave, after lyophilization, [5-chloro-2-(trifluoromethoxy)phenyl]boronic acid as a white powder. NMR (500 MHz, CDCl$_3$) δ: 7.32 (d, J=8.8 Hz, 1H); 7.60 (dd, J=2.7, 8.8 Hz, 1H); 8.20 (d, J=2.7 Hz, 1H).

Intermediate I

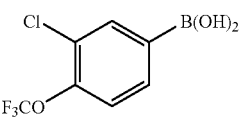

[3-Chloro-4-(trifluoromethoxy)phenyl]boronic acid. A solution of NaNO$_2$ (2.4 g, 33 mmol) in water (6 ml) was added slowly to a suspension of [3-chloro-4-(trifluoromethoxy)phenyl]amine (2.95 g, 13.9 mmol) in 20 ml of 15% HCl at 0° C. The solid material was removed by filtration and a solution of NaBF$_4$ (2.4 g, 22 mmol) in water (15 ml) was mixed with the filtrate. The solid was collected by filtration, dried at 40° C., to give 2.62 g of the diazonium salt. LC-MS: single peak with correct MS (223.6).

The above solid was then mixed with bis(pinacolato)diboron (2.14 g, 8.4 mmol), PdCl$_2$(dppf) (180 mg, 2.5%) in a flask, de-oxygenated by vacuum-N$_2$ fill cycles, followed by addition of MeOH (N$_2$ purged). The mixture was stirred at room temperature for 2 h. Solvent was evaporated and the residue chromatographed (SiO$_2$, 0-10% ethyl acetate in hexane gradient) to give the borate ester as an oil. NMR (500 MHz, CDCl$_3$) δ: 1.34 (s, 12H); 7.31 (qd, J=1.5, 8.2 Hz, 1H); 7.71 (dd, J=1.5 8.2 Hz, 1H); 7.90 (d, J=1.5 Hz, 1H).

The borate ester was hydrolyzed in acetone-HCl as described for [6-(trifluoromethoxy)-2-naphthyl]boronic acid to give [3-chloro-4-(trifluoromethoxy)phenyl]boronic acid as a fine powder. NMR (500 MHz, CDCl$_3$) δ: 7.48 (qd, J=1.6, 8.1 Hz, 1H); 8.13 (dd, J=1.6, 8.1 Hz, 1H); 8.25 (d, J=1.6 Hz, 1H).

Intermediate J

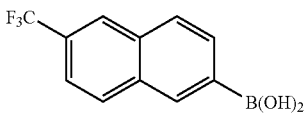

Step A 6-(Trifluoromethyl)-1,4-dihydro-1,4-epoxynaphthalene. To 25 mL of tetrahydrofuran at −78° C. was added n-butyllithium (13.9 mL, 22.2 mmol) followed by diisopropylamine (3.1 mL, 22.2 mmol). The resultant mixture was stirred at −78° C. for 10 min. then furan (24 mL, 330 mmol) was added slowly. 4-Bromobenzotrifluoride (5 g, 22.2 mmol) was added to the reaction mixture as a solution in 10 mL of tetrahydrofuran, the cold bath was removed, and the mixture allowed to warm to ambient temperature over 2.5 h. Water was added, the mixture poured into hexanes, and the organic layer washed successively with two portions of 1N HCl and one portion of brine. The organic layer was dried over magnesium sulfate, concentrated in vacuo, and the oily residue purified by flash column chromatography (SiO₂, 5% ethyl acetate/hexanes) to give the title compound. ¹H NMR (500 MHz, CDCl₃) δ: 7.51 (s, 1H); 7.35 (m, 2H); 7.10 (m, 2H); 5.81 (br s, 2H). HPLC/MS: m/z=213.00 (M+1).

Step B 2-Bromo-6-(trifluoromethyl)-1,4-dihydro-1,4-epoxynaphthalene and 2-bromo-7-(trifluoromethyl)-1,4-dihydro-1,4-epoxynaphthalene. 6-(Trifluoromethyl)-1,4-dihydro-1,4-epoxynaphthalene (380 mg, 1.79 mmol) and sodium carbonate (200 mg, 1.89 mmol) were combined in 11 mL of carbon tetrachloride and heated to 70° C. Bromine (288 mg, 1.80 mmol) was added drop-wise as a solution in 3 mL of carbon tetrachloride and the resultant mixture heated at 80° C. for 10 min. The pale yellow solution was cooled, filtered through a pad of sodium sulfate, and concentrated in vacuo. The oily residue obtained was suspended in 4 mL of tetrahydrofuran and added to a suspension of potassium tert-butoxide (638 mg, 5.4 mmol) in 5 mL of tetrahydrofuran at 50° C. After heating at 50° C. for 24 h, the mixture was cooled, poured into hexanes, and washed successively with two portions of water and one portion of brine. The organic layer was dried over magnesium sulfate, concentrated in vacuo, and purified by preparative TLC (SiO₂, 5% ethyl acetate/hexanes) to give the title compounds. 2-Bromo-6-(trifluoromethyl)-1, 4-dihydro-1,4-epoxynaphthalene: ¹H NMR (500 MHz, CDCl₃) δ: 7.51 (m, 2H); 7.40 (d, J=7.3 Hz); 7.02 (d, J=2 Hz, 1H); 5.84 (br s, 1H); 5.55 (s, 1H) and 2-bromo-7-(trifluoromethyl)-1,4-dihydro-1,4-epoxynaphthalene (obtained as a 2:1 mixture with the reaction intermediate (1R,2R,3S,4S),-2,3-dibromo-6-(trifluoromethyl)-1,2,3,4-tetrahydro-1,4-epoxynaphthalene). This mixture was separated at the next step. ¹H NMR (500 MHz, CDCl₃) δ: 7.65 (m, 2.5H); 7.61 (d, J=8.0 Hz, 0.5H); 7.52, (d, J=7.8 Hz, 0.5H); 7.40 (m, 2H); 7.00 (d, J=2.1 Hz, 1H); 5.83 (br s, 1H); 5.61 (s, 0.5H); 5.55 (s, 1H); 4.27 (m, 0.5H).

Step C 2-Bromo-6-(trifluoromethyl)naphthalene. 2-Bromo-6-(trifluoromethyl)-1,4dihydro-1,4-epoxynaphthalene (624 mg, 2.14 mmol) and sodium iodide (980 mg, 6.54 mmol) were dissolved in 13 mL of dry acetonitrile and trimethylsilyl chloride (0.823 mL, 6.54 mmol) added. The resultant mixture was stirred at ambient temperature for 3.5 h, poured into hexanes, and the organic layer washed successively with two portions of water and one portion of brine. The organic layer was dried over magnesium sulfate, concentrated in vacuo, and the residue purified by flash column chromatography (SiO₂, 5% ethyl acetate/hexanes) to give 2-bromo-6-(trifluoromethyl)naphthalene as a white solid. ¹H NMR (500 MHz, CDCl₃) δ: 8.15 (s, 1H); 8.11 (s, 1H); 7.89 (d, J=8.7 Hz, 1H); 7.83 (d, J=8.7 Hz, 1H); 7.70 (dd, J=1.6, 8.7 Hz, 1H); 7.69 (dd, J=1.8, 8.7 Hz, 1H).

Step D [6-(Trifluoromethyl)-2-naphthyl]boronic acid. 2-Bromo-6-(trifluoromethyl)-naphthalene (50 mg, 0.182 mmol), bis(pinacolato)diboron (92 mg, 0.362 mmol), and potassium acetate (53 mg, 0.540 mmol) were suspended in 2.5 mL of methyl sulfoxide. The mixture was de-oxygenated by four vacuum-nitrogen fill cycles, and dichloro[1,1'-bis (diphenylphosphino)ferrocene]palladium (II) dichloromethane adduct (3.7 mg, 0.0045 mmol) added, and the resultant mixture heated at 80° C. under a nitrogen atmosphere for 1 h. The mixture was cooled, diluted with ethyl acetate, and washed successively with two portions of water and one portion of brine. The organic layer was dried over magnesium sulfate, concentrated in vacuo, and the residue suspended in a mixture of 10 mL of acetone and 2 mL of aqueous 2N hydrochloric acid. The resultant mixture was heated at 60° C. for 16 hours and the crude boronic acid purified by reverse phase HPLC to give [6-(trifluoromethyl)-2-naphthyl]boronic acid as a white powder. ¹H NMR (500 MHz, DMSO) δ: 8.47 (s, 1H); 8.38 (s, 1H); 8.33 (br s, 2H); 8.14 (d, J=8.7 Hz, 1H); 8.07 (d, J=8.2 Hz, 1H); 8.00 (d, J=8.2 Hz, 1H); 7.73 (dd, J=1.6, 8.5 Hz, 1H).

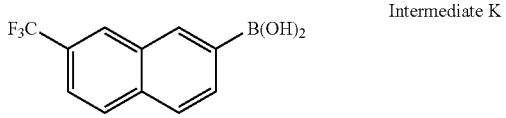

Intermediate K

Step A 2-Bromo-7-(trifluoromethyl)naphthalene. This compound was made in the same manner as the 2,6-isomer described above for Intermediate J. ¹H NMR (500 MHz, CDCl₃) δ: 8.11 (d, J=1.6 Hz, 1H); 8.07 (s, 1H); 7.94 (d, J=8.7 Hz, 1H); 7.79 d, J=9.0 Hz, 1H); 7.70 (dd, J=1.8, 8.9 Hz, 1H); 7.68 (dd, J=1.9, 8.9 Hz, 1H).

Step B [7-(Trifluoromethyl)-2-naphthyl]boronic acid. This was made in the same manner as the 2.6-isomer described above for Intermediate J. ¹H NMR (500 MHz, CD₃OD) δ: 8.29 (m, 2H); 8.05 (d, J=8.7 Hz, 1H); 8.00-7.88 (m, 2H); 7.69 (d, J=8.5 Hz, 1H).

Intermediate L

Step A 2-Bromo-6-chloronaphthalene. 6-Bromo-2-naphthoic acid (4.00 g, 15.9 mmol) was treated with 40 mL of thionyl chloride at 80° C. for 1 h. The mixture was concentrated in vacuo, and the resultant unpurified acid chloride (3 g, 11.1 mmol) was combined with 2,2'-azobisisobutyronitrile (731 mg, 4.45 mmol) in 25 mL of carbon tetrachloride and 15 mL of chlorobenzene. This mixture was added slowly via dropping funnel to a mixture of 2-mercaptopyridine-1-oxide sodium salt (1.99 g, 13.7 mmol) and 4-(dimethylamino)pyridine (150 mg, 1.23 mmol) at 100° C. After the addition was complete, the mixture was stirred for an additional 4 h, cooled, and the solid by-product precipitate removed by filtration. The filtrate was concentrated in vacuo and the residue purified by flash column chromatography (SiO₂, hexanes) to provide the title compound as a white solid. ¹H NMR (500 MHz, CDCl₃) δ: 8.02 (br s, 1H); 7.83 (d, J=1.6 Hz, 1H); 7.72 (d, J=8.7 Hz, 1H); 7.66 (d, J=8.7 Hz, 1H); 7.60 (dd, J=2.0 8.9 Hz, 1H); 7.47 (dd, J=2.1, 8.7 Hz, 1H).

Step B 2-(6-Chloro-2-naphthyl)-4,4,5,5-tetramethyl-1,3, 2-dioxaborolane. 2-Bromo-6-chloronaphthalene (205 mg, 0.849 mmol), bis(pinacolato)diboron (432 mg, 1.70 mmol), and potassium acetate (250 mg, 2.55 mmol) were dissolved in 12 mL of methyl sulfoxide. The mixture was de-oxygenated by four vacuum-nitrogen fill cycles, and dichloro[1,1'-bis (diphenylphosphino)ferrocene]palladium (II) dichloromethane adduct (70 mg, 0.085 mmol) added. The resultant mixture was heated at 80° C. under a nitrogen atmosphere for 3 h then was allowed to sit at ambient temperature for 16 h. The mixture was diluted with ethyl acetate, and washed successively with two portions of water and one portion of brine. The organic layer was dried over magnesium sulfate, concentrated in vacuo, and the residue purified by flash column chromatography to provide the title compound. ¹H NMR (500 MHz, DMSO) δ: 8.34 (s, 1H); 8.10 (m, 2H); 7.89 (d, J=8.3 Hz, 1H), 7.76 (d, J=8.3 Hz, 1H); 7.54 (dd, J=1.8, 8.7 Hz, 1H); 1.33 (br s, 12H).

Step C (6-Chloro-2-naphthyl)boronic acid. 2-(6-Chloro-2-naphthyl)-4,4,5,5-tetramethyl-1,3,2-dioxaborolane (340 mg, 1.18 mmol) was suspended in a mixture of 20 mL of acetone and 5 mL of aqueous 2N hydrochloric acid and heated at 50° C. for 16 h. The product was purified by reverse phase HPLC to provide the title compound as a white powder. $^1$H NMP (500 MHz, DMSO) δ: 8.38 (s, 1H); 8.23 (s, 2H); 8.01 (d, J=2.1 Hz, 1H); 7.95 (d, J=8.7 Hz, 1H); 7.91 (d, 8.2 Hz, 1H); 7.84 (d, J=8.2 Hz, 1H); 7.50 (dd, J=2.3, 8.7 Hz, 1H).

Intermediate M

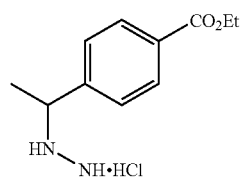

Step A tert-Butyl 2-{1-[4-(ethoxycarbonyl)phenyl]ethylidene}hydrazinecarboxylate. A solution of tert-butyl carbazate (13.90 g, 105 mmol) and ethyl 4-acetylbenzoate (20.00 g, 0.104 mol) in toluene (120 mL) was stirred at 80° C. overnight (15 h). tert-butyl-2-{1-[4-(ethoxycarbonyl)phenyl]ethylidene}hydrazinecarboxylate separated as crystalline solid and was collected by filtration of the mixture. HPLC/MS: m/z=307.3 (M+1)$^+$, R$_t$=3.47 min. $^1$H NMR (500 MHz, CDCl$_3$): δ 8.05 (2H, d, J=8.5 Hz), 7.88 (2H, d, J=8.5 Hz), 7.79 (1H, br s), 4.41 (2H, q, J=7.0 Hz), 2.24 (3H, s), 1.58 (9H, s), 1.43 (3H, t, J=7.0 Hz).

Step B tert-Butyl 2-{1-[4-(ethoxycarbonyl)phenyl]ethyl}hydrazinecarboxylate. In a N$_2$ filled round-bottomed flask equipped with serum caps and magnetic stirrer, NaBH$_3$CN (6.0 g, 0.095 mol) and tert-butyl-2-{1-[4-(ethoxycarbonyl)phenyl]ethylidene}hydrazinecarboxylate (25.6 g, 0.084 mol) were dissolved in THF (200 mL). A solution of p-toluenesulfonic acid monohydrate (17.3 g, 0.091 mol) in THF (50 mL) was slowly added via syringe pump. Completion of addition required about 10 h. The mixture was diluted with EtOAc (200 mL) and the suspension extracted with brine (150 mL). The organic phase was separated, dried (Na$_2$SO$_4$) and concentrated on a rotovap to give white solid. The white solid was taken in CH$_2$Cl$_2$ (100 mL) and 1 N NaOH (100 mL) was added. The suspension was stirred vigorously at r.t. for 1 h and then diluted with CH$_2$Cl$_2$ (100 mL). The organic phase was separated and extracted with 1N HCl (2×150 mL), brine (2×150 mL), dried (Na$_2$SO$_4$) and concentrated to approximately 50 mL. Product precipitated as white solid and was collected by filtration and washed with hexane to yield tert-butyl 2-{1-[4-(ethoxycarbonyl)phenyl]ethyl}hydrazinecarboxylate. HPLC/MS: m/z=331.3 (M+Na)$^+$, R$_t$=3.24 min. $^1$H NMR (500 MHz, CDCl$_3$): δ 8.03 (2H, d, J=8.0 Hz), 7.44 (2H, d, J=8.0 Hz), 5.99 (1H, br s), 4.40 (2H, q, J=7.0 Hz), 4.29 (1H, m), 1.45 (9H, s), 1.41 (3H, t, J=7.0 Hz), 1.35 (3H, d, J=6.5 Hz).

Step C {1-[4-(Ethoxycarbonyl)phenyl]ethyl}hydrazinium chloride tert-Butyl 2-{1-[4-(ethoxycarbonyl)phenyl]ethyl}hydrazinecarboxylate (29 g, 94 mmol) was treated with 100 ml of TFA-DCM-triisopropylsilane (20:20:1) at room temperature for one hour. The mixture was concentrated under reduced pressure, and the residue was dissolved in water (100 ml), washed with DCM 2×. The DCM was back extracted with water 3×. HCl (5N, 20 ml) was added to the combined water solution and concentrated to ~50 ml. CH$_3$CN (50 ml) was added and this was lyophilized to give 22.7 g of {1-[4-(ethoxycarbonyl)phenyl]ethyl)}-hydrazinium chloride. NMR (500 MHz, acetone-d$_6$) δ: 1.34 (t, J=7.1 Hz, 3H); 1.67 (d, J=6.8 Hz, 3H); 4.33 (q, J =7.1 Hz, 2H), 4.907 (q, J=6.8 Hz, 1H), 7.76 (d, J=8.5 Hz, 2H), 7.97 (d, J=8.5 Hz, 2H). MS C$_{11}$H$_{16}$N$_2$O$_2$ Cald: 208.12; Obsd (M+1): 209.19.

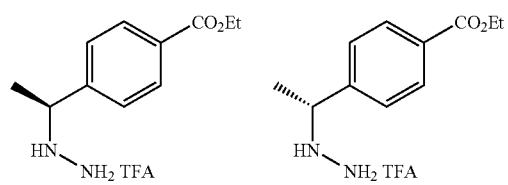

Step D {(1S)-1-[4-(ethoxycarbonyl)phenyl]ethyl}hydrazinium trifluoroacetate and {(1R)-1-[4-(ethoxycarbonyl)phenyl]ethyl}hydrazinium trifluoroacetate. tert-Butyl 2-{1-[4-(ethoxycarbonyl)phenyl]ethyl}hydrazinecarboxylate was analyzed by chiral HPLC using two sets of conditions. 1) Daicel column Chiralcel OJ, 40° C., 0.75 ml/min, 10% EtOH/90% n-heptane: t$_1$ 6.66 min; t$_2$ 12.25 min. Enantiomers were resolved on a preparative scale using this column (30% EtOH/70% n-Heptane). 2) Daicel column ChiralPak AD, 0.75 mL/min, 10% EtOH/90% n-heptane: t$_1$ 12.17 min; t$_2$ 15.49 min. Enantiomers were resolved on a preparative scale using this column (20% EtOH/80% n-Heptane). The fast moving enantiomer was identical in each case and was subsequently established to be the (S)enantiomer ([α]$_D^{20}$=−120° (c1.1, MeOH)), vide infra. The slower (R)-enantiomer was also isolated ([α]$_D^{20}$=+122° (c1.1, MeOH)).

Either enantiomer could be deprotected with 45:45:10 TFA:DCM:TIPS (40° C., 1.5 hr). The excess reagent and solvent was evaporated, and the residue was dissolved in water. The water solution was washed with DCM 2×. The DCM layers were back extracted with more water. The combined water solution was evaporated under vacuum (temp<45° C.), followed by azeotropic drying with toluene to give for the (S)-isomer-{(1S)-1-[4-(ethoxycarbonyl)phenyl]-ethyl}hydrazinium trifluoroacetate as a viscous oil. NMR (500 MHz, CD$_3$OD) δ: 1.38 (t, J=7.1 Hz, 3H); 1.49 (br d, J=7.0 Hz, 3H); 4.26 (br q, J=7.0 Hz, 1H); 4.37 (q, J=7.1 Hz, 2H); 7.54 (d, J=8.2 Hz, 2H); 8.07 (d, J=8.2 Hz, 2H). MS C$_{11}$H$_{16}$N$_2$O$_2$ Cald: 208.12; Obsd (M+1): 209.19. {(1R)-1-[4-(ethoxycarbonyl)phenyl]ethyl}hydrazinium trifluoroacetate could be prepared in an identical fashion.

Determination of Absolute Configuration of Enantiomeric Hydrazines

Absolute configuration of the enantiomers of tert-butyl 2-{1-[4-(ethoxycarbonyl)phenyl]ethyl}hydrazinecarboxylate was established by conversion to ethyl 4-[1-(2-benzoylhydrazino)ethyl]benzoate, followed by comparison of the sign of optical rotation with reported data [Burk et al., *Tetrahedron*, 1994, 50, 4399-(S)-1-p-carboethoxyphenyl-1-(2-benzoylhydrazino)ethane (95% ee; [α]$_D^{20}$=−200.0° (cl, CHCl$_3$), HPLC Daicel Chiracel OJ, 40° C., 0.5 mL/min, 10% 2-propanol/90% hexane: R$_t$=33.1 min). (R)-isomer R$_t$=37.4 min.].

Thus the slow moving enantiomer tert-butyl 2-{1-[4-(ethoxycarbonyl)phenyl]ethyl}hydrazinecarboxylate (0.74 g, 2.42 mmol) from a chiral separation as described above was treated with TFA/CH$_2$Cl$_2$ (1:1, 10 mL) for 1 h at r.t. The reaction was concentrated on a rotovap and the residual TFA was removed by co-evaporation from toluene. The resulting ethyl 4-(1-hydrazinoethyl)benzoate was then dissolved in $CH_2Cl_2$ (15 mL) and cooled to −78° C. A solution of benzoyl chloride (365 μL, 3.15 mmol) and 2,6-di-tert-butyl-4-methylpyridine (745 mg, 3.63 mmol) in $CH_2Cl_2$ (5 mL) was added slowly at −78° C. After 3 h at −78° C., the reaction mixture was loaded quickly on a $SiO_2$ column and eluted with 30% EtOAc/hexane. Fractions containing product were concentrated and purified further on HPLC using Kromasil $C_8$ column (10% to 70% $CH_3CN/H_2O/0.1\%$ TFA, 12 min), and again on silica gel column (30% EtOAc/Hexane) to give (R)-(+)-ethyl 4-[1-(2-benzoylhydrazino)ethyl]benzoate. HPLC/MS: m/z=313.3 (M+1)$^+$, $R_f$=3.08 min. Daicel column Chiralcel OJ, 40° C., 0.5 mL/min, 10% isopropanol/90% n-heptane: t 35.79 min; $[\alpha]_D^{20}$=+192.4° (cl, $CHCl_3$); $^1$H NMR (500 MHz, $CDCl_3$): δ 8.03 (2H, d, J=8.0 Hz), 7.94 (1H, br s), 7.66 (2H, d, J=7.5 Hz), 7.51 (1H, t, J=7.5 Hz), 7.54 (2H, d, J=8.0 Hz), 7.40 (2H, t, J=8.0 Hz), 4.39 (2H, q, J=7.0 Hz), 4.36 (1H, q, J=7.0 Hz), 1.46 (3H, d, J=6.0 Hz), 1.41 (3H, t, J=7.0 Hz); $^{13}$C NMR (500 MHz, $CDCl_3$): δ 167.76, 166.69, 148.16, 132.70, 132.27, 130.21, 130.18, 128.94, 127.47, 127.15, 61.22, 60.21, 21.21, 14.58. (S)-(−)-ethyl 4-[1-(2-benzoylhydrazino)ethyl]-benzoate was similarly prepared from the faster moving isomer of tert-butyl 2-{1-[4-(ethoxycarbonyl)phenyl]ethyl}hydrazinecarboxylate. HPLC/MS: m/z=313.4 (M+1)$^+$, $R_f$=3.09 min. Daicel column Chiralcel OJ, 40° C., 0.5 mL/min, 10% isopropanol/90% n-heptane: t 34.99 min; $[\alpha]_D^{20}$=−194.4° (cl, $CHCl_3$); $^1$H NMR (500 MHz, $CDCl_3$): δ 8.02 (2H, d, J=8.0 Hz), 7.73 (1H, br s), 7.65 (2H, d, J=8.0 Hz), 7.49 (1H, t, J=8.0 Hz), 7.48 (2H, d, J=8.0 Hz), 7.39 (2H, t, J=8.0 Hz), 4.38 (2H, q, J=7.0 Hz), 4.34 (1H, q, J=7.0 Hz), 1.44 (3H, d, J=6.5 Hz), 1.41 (3H, t, J=7.0 Hz); $^{13}$C NMR (500 MHz, $CDCl_3$): δ 167.81, 166.74, 148.73, 132.92, 132.15, 130.13, 130.02, 128.90, 127.43, 127.12, 61.20, 60.09, 21.52, 14.58.

Intermediate N

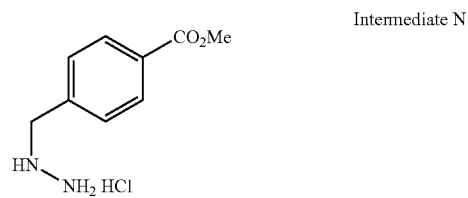

Step A tert-Butyl (2E)-2-[4-(methoxycarbonyl)benzylidene]hydrazinecarboxylate. Using chemistry described in Intermediate M, Step A above, the title compound was prepared. NMR (500 MHz, $CDCl_3$) δ: 1.55 (s, 9H); 3.92 (s, 3H); 7.74 (d, J=8.5 Hz, 2H), 7.88 (br s, 1H); 7.96 (br s, 1H); 8.04 (d, J=8.5 Hz, 2H).

Step B tert-Butyl 2-[4-(methoxycarbonyl)benzyl]hydrazinecarboxylate. Using chemistry described in Intermediate M, Step B above, the title compound was prepared. NMR (500 MHz, $CDCl_3$) δ: 1.46 (s, 9H); 3.91 (s, 3H); 4.06 (s, 2H); 6.03 (br s, 1H); 7.42 (q, J=8.3 Hz, 2H); 8.00 (d, J=8.3 Hz, 2H).

Step C [4-(Methoxycarbonyl)benzyl]hydrazinium chloride. Using chemistry described in Intermediate M, Step C above, the title compound was prepared. NMR (500 MHz, $CD_3OD$) δ: 3.9i (s, 3H); 4.19 (s, 2H); 7.54 (d, J=8.3 Hz, 2H); 8.05 (d, J=8.3 Hz, 2H). MS $C_9H_{12}N_2O_2$ Cald: 180,09; Obsd (M+1): 181.12.

Generic Synthesis of Pyrazoles, Method A

EXAMPLE 1

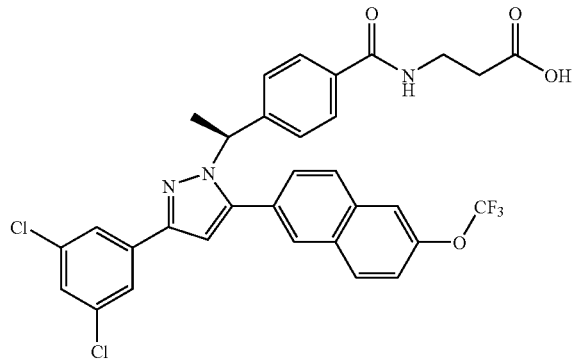

Step A Ethyl 4-{1-[3-(3,5-dichlorophenyl)-5-oxo-4,5-dihydro-1H-pyrazol-1-yl]ethyl}benzoate. A solution of ethyl (3,5-dichlorobenzoyl)acetate (3.0 g, 11.5 mmol) and {1-[4-(ethoxycarbonyl)phenyl]ethyl}hydrazinium chloride (2.55 g, 10.4 mmol) was refluxed in HOAc (80 ml) for 4 hr. The solvent was removed under reduced pressure, and the residue taken up with ethyl acetate, washed with sat. $NaHCO_3$ 2x, brine, and dried over $Na_2SO_4$. Flash column chromatography ($SiO_2$, 0-5% ethyl acetate in DCM gradient) gave ethyl 4-{1-[3-(3,5-dichlorophenyl)-5-oxo-4,5-dihydro-1H-pyrazol-1-yl]ethyl}benzoate as a white solid. TLC (5% ethyl acetate-DCM) $R_f$ 0.43. NMR (500 MHz, $CDCl_3$) δ: 1.38 (t, J=7.1 Hz, 3H); 1.78 (d, J=7.0 Hz, 3H); 3.55 (d, J=22.6 Hz, 1H); 3.60 (d, J=22.6 Hz, 1H); 4.36 (q, J=7.1 Hz, 2H); 5.57 (q, J=7.0 Hz, 1H); 7.39 (t, J=1.9 Hz, 1H); 7.50 (d, J=8.4 Hz, 2H). 7.52 (d, J=1.9 Hz, 2H); 8.02 (d, J=8.4 Hz, 2H). MS $C_{20}H_{18}Cl_2N_2O_3$ Cald: 404.07; Obsd (M+1): 405.20.

Step B tert-Butyl N-(4-{1-[3-(3,5-dichlorophenyl)-5-oxo-4,5-dihydro-1H-pyrazol-1-yl]ethyl}benzoyl)-β-alaninate. Ethyl 4-{1-[3-(3,5-dichlorophenyl)-5-oxo-4,5-dihydro-1H-pyrazol-1-yl]ethyl}benzoate (2.23 g, 5.50 mmol) was dissolved in MeOH-dioxane (1:1, 50 ml). A solution of NaOH (0.7 g/15 ml) was added. The mixture was heated to 60° C. for 1 hr. This was acidified with 2N HCl (10 ml), and the solvent was removed and residue vacuum dried to give a pale yellow solid (mixture of product acid and NaCl). This solid was suspended in DMF (15 ml), followed with DIEA (4.8 ml), beta-alanine t-butyl ester hydrochloride (3 g ). A solution of PyBOP (3.43 g) in DMF (5 ml) was then added. After stirring at room temperature for 3 hr, more PyBOP (1 g) was added and the reaction mixture was stirred overnight. After addition of water (5 ml), the mixture was heated to 60° C. for 30 min. Ethyl acetate (150 ml) was added, and the organic layer was washed with 0.5 N HCl 2x, 5% $K_2CO_3$ 2x, brine 2x. Evaporation of solvent gave an oily residue, which after flash column chromatography ($SiO_2$, 0-30% ethyl acetate in DCM) afforded tert-butyl N-(4-{1-[3-(3,5-dichlorophenyl)-5-oxo-4,5-dihydro-1H-pyrazol-1-yl]ethyl}benzoyl)-β-alaninate as a white solid. NMR (500 MHz, DMSO-$d_6$) δ: 1.37 (s, 9H); 1.78 (d, J=7.1 Hz, 3H); 2.45 (t, J=7.0 Hz, 2H); 3.42 (q, J=7.0 Hz, 2H); 5.99 (s, 1H); 7.30 (d, J=8.3 Hz, 2H); 7.47 (t, J=1.0 Hz, 1H). 7.73 (d, J=8.3 Hz, 2H); 7.76 (d, J=1.9 Hz, 2H); 8.43

(t, J=5.6 Hz, 1H); 11.34 (s, 1H). MS $C_{25}H_{27}Cl_2N_3O_4$ Cald: 503.14; Obsd (M+Na): 526.05.

Step C tert-Butyl N-{4-[1-(3-(3,5-dichlorophenyl)-5-{[(trifluoromethyl)sulfonyl]oxy}-1H-pyrazol-1-yl)ethyl]benzoyl}-β-alaninate. tert-Butyl N-(4-{1-[3-(3,5-dichlorophenyl)-5-oxo-4,5-dihydro-1H-pyrazol-1-yl]ethyl}benzoyl)-β-alaninate (2.05 g, 4.06 mmol), TEA (1.7 ml, 12 mmol) were dissolved in THF (35 ml) at −78° C. Triflic anhydride (1.1 ml, 6.2 mmol) was added. The cooling bath was removed and the reaction mixture was stirred for 1 hr. The reaction was quenched by adding ethyl acetate, water. The organic layer was washed with 0.5 N HCl 2×, brine 2×, and dried over $Na_2SO_4$. Evaporation of solvent and flash column chromatography ($SiO_2$, 0-10% ethyl acetate in DCM gradient) gave tert-butyl N-{4-[1-(3-(3,5-dichlorophenyl)-5-{[(trifluoromethyl)sulfonyl]oxy}-1H-pyrazol-1-yl)ethyl]benzoyl}-β-alaninate as a colorless dry film. NMR (500 MHz, $CDCl_3$) δ: 1.45 (s, 9H); 1.97 (d, J=7.1 Hz, 3H); 2.53 (t, J=5.9 Hz, 2H); 3.67 (q, J=5.9 Hz, 2H); 5.54 (q, J=7.1 Hz, 1H); 6.43 (s, 1H); 6.86 (t, J=6.2 Hz, 1H); 7.33 (t, J=2.0 Hz, 1H); 7.36 (d, J=8.4 Hz, 2H). 7.67 (d, J=2.0 Hz, 2H); 7.74 (d, J=8.4 Hz, 2H). MS $C_{26}H_{26}Cl_2F_3N_3O_6S$ Cald: 635.09; Obsd (M+Na): 657.89.

tert-Butyl N-{4-[1-(3-(3,5-dichlorophenyl)-5-{[(trifluoromethyl)sulfonyl]oxy}-1H-pyrazol-1-yl)ethyl]benzoyl}-β-alaninate can be resolved via chiral HPLC (ChiralPak AD column, analytical conditions—6% isopropanol/heptane, (S)-isomer $R_t$=16.1 and (R)-isomer 18.1 min, or using SFC chromatography 15% $MeOH:CO_2$, 1.5 mL/min-(R)-isomer $R_t$=5.5 and (S)-isomer 6.1 min, preparative conditions using SFC chromatography 15% $MeOH:CO_2$, 50 mL/min). The absolute stereochemistry of the two samples was established by preparation of an authentic sample of tert-butyl N-{4-[(S) 1-(3-(3,5-dichlorophenyl)-5-{[(trifluoromethyl)sulfonyl]oxy}-1H-pyrazol-1-yl)ethyl]benzoyl}-β-alaninate (Chiral-Pak AD column, 6% isopropanol/heptane, $R_t$=15.8 min, coinjection with (S)-isomer from above $R_t$=16.1 min) from {(1S)-1-[4-(ethoxycarbonyl)phenyl]-ethyl}hydrazinium trifluoroacetate, vide supra). The (S) isomer was used in Step D.

Alternatively, tert-butyl N-{4-[(S)1-(3-(3,5-dichlorophenyl)-5-{[(trifluoromethyl)sulfonyl]oxy}-1H-pyrazol-1-yl)ethyl]benzoyl}-β-alaninate can be prepared without chromatographic separation of the enantiomers from ethyl 4-{(1S)-1-[3-(3,5-dichlorophenyl)-5-oxo-4,5-dihydro-1H-pyrazol-1-yl]ethyl}benzoate (Method C, Example 4, Step A) as described in Steps B and C above.

Step D N-[4-((1S)-1-{3-(3,5-Dichlorophenyl)-5-[6-(trifluoromethoxy)-2-naphthyl]-1H-pyrazol-1-yl}ethyl)benzoyl]-β-alanine. tert-Butyl N-{4-[(1S)-1-(3-(3,5-dichlorophenyl)-5-{[(trifluoromethyl)sulfonyl]oxy}-1H-pyrazol-1-yl)ethyl]benzoyl}-β-alaninate (10 mg, 0.016 mmol), 6-trifluoromethoxy-2-naphthylboronic acid (5.1 mg, 0.02 mmol), and TEA (14 ul, 0.1 mmol) were dissolved in dimethoxyethane (0.5 ml) and deoxygenated by vacuum-$N_2$ fill cycles. The catalyst $Pd(PPh_3)_4$ (2 mg, 10% mol) was added and the mixture was deoxygenated again before heated in microwave reactor to 100° C. for 10 min. The mixture was quenched with 1.5 ml of $CH_3CN:H_2O$ (3:1, with 5% TFA) and product separated through reverse phase preparative HPLC. The collected product was treated with 1 ml of TFA-DCM (1:2) for 30 min, and the residue lyophilized to give N-[4-((1S)-1-{3-(3,5-dichlorophenyl)-5-[6-(trifluoromethoxy)-2-naphthyl]-1H-pyrazol-1-yl}ethyl)benzoyl]-β-alanine as fine powder. NMR (500 MHz, DMSO-$d_6$) δ: 1.91 (d, J=7.0 Hz, 3H); 2.46 (t, J=7.0 Hz, 2H); 3.41 (q, J=7.0 Hz, 2H); 5.78 (q, J=7.0 Hz, 1H); 7.21 (d, J=8.4 Hz, 2H); 7.22 (s, 1H); 7.57 (t, J=1.9 Hz, 1H; 7.58~7.60 (m, 2H); 7.72 (d, J=8.4 Hz, 2H); 7.94 (d, J=1.9 Hz, 2H); 8.04 (br s, 1H); 8.06 (br s, 1H); 8.09 (d, J=9.1 Hz, 1H); 8.13 (d, J=8.6 Hz, 1H); 8.44 (t, J=5.5 Hz, 1H). MS $C_{32}H_{24}Cl_2F_3N_3O_4$ Cald: 641.11; Obsd (M+1): 642.22.

EXAMPLE 2

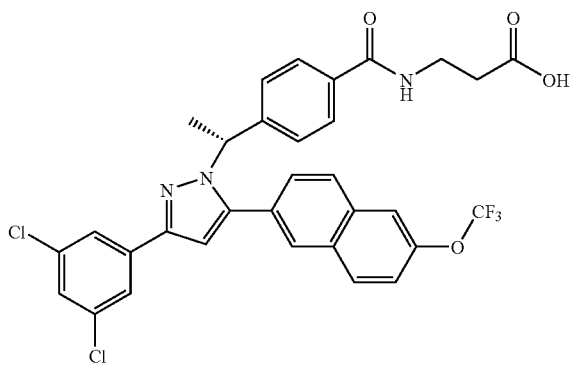

N-[4-((1R)-1-{3-(3,5-Dichlorophenyl)-5-[6-(trifluoromethoxy)-2-naphthyl]-1H-pyrazol-1-yl}ethyl)benzoyl]-β-alanine. tert-Butyl N-{4-[(1R)-1-(3-(3,5-dichlorophenyl)-5-{[(trifluoromethyl)sulfonyl]oxy}-1H-pyrazol-1-yl)ethyl]benzoyl}-β-alaninate was converted as described in Example 1, Step D to N-[4-((1R)-1-{3-(3,5-dichlorophenyl)-5-[6-(trifluoromethoxy)-2-naphthyl]-1H-pyrazol-1-yl}ethyl)benzoyl]-β-alanine as fine powder. NMR (500 MHz, DMSO-$d_6$) δ: 1.91 (d, J=7.0 Hz, 3H); 2.46 (t, J=7.0 Hz, 2H); 3.4 (m, 2H); 5.77 (q, J=7.0 Hz, 1H); 7.20 (d, J=8.2 Hz, 2H); 7.21 (s, 1H); 7.56 (t, J=2.0 Hz, 1H); 7.57~7.60 (m, 2H); 7.71 (d, J=8.4 Hz, 2H); 7.93 (d, J=2 Hz, 2H); 8.04 (br s, 1H); 8.06 (br s, 1H); 8.09 (d, J=9.1 Hz, 1H); 8.13 (d, J=8.6 Hz, 1H); 8.44 (t, J=5.5 Hz, 1H). MS $C_{32}H_{24}Cl_2F_3N_3O_4$ Cald: 641.11; Obsd (M+1): 642.22.

Generic Synthesis of Pyrazoles, Method B

EXAMPLE 3

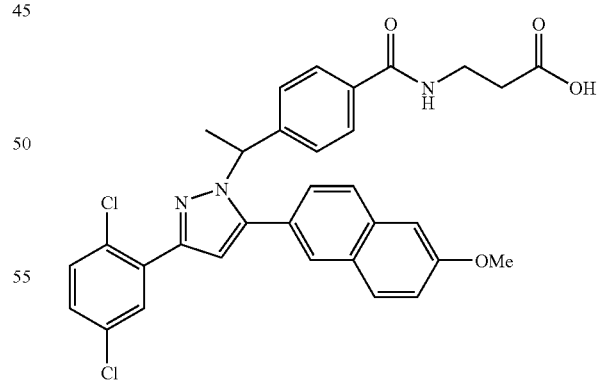

Step A Ethyl 3-(6-methoxy-2-naphthyl)-3-oxopropanoate. A suspension of $MgCl_2$ (3.5 g, 35 mmol), potassium ethyl malonate (4.6 g, 30 mmol), and triethylamine (15 ml, 105 mmol) in dry ethyl acetate (100 ml) was stirred at 40° C. overnight. A suspension of 6-methoxynaphthyl-2-acid chloride (4.9 g, 22.2 mmol) in ethyl acetate (20 ml) was then added to the above mixture. The reaction was stirred at room temperature for 2.5 hour. The reaction was quenched with 60 ml of 2N HCl, stirred for 5 min and then washed with 0.5 N HCl 2×, 5% $K_2CO_3$ 2×, brine 2×. Evaporation of solvent and vacuum drying afforded ethyl 3-(6-methoxy-2-naphthyl)-3-oxopropanoate as an oil. NMR (500 MHz, $CDCl_3$) δ: 1.26 (t, J=7.1 Hz, 3H); 3.95 (s, 3H); 4.09 (s, 2H); 4.23 (q, J=7.1 Hz, 2H); 7.15 (d, J=2.5 Hz, 1H); 7.21 (dd, J=2, 5 Hz, 9.0 Hz, 1H); 7.77 (d, J=8.7 Hz, 1H); 7.85 (d, J=9.0 Hz, 1H); 7.98 (dd, J=1.8 Hz, 8.7 Hz, 1H); 8.38 (d, J=1.8 Hz, 1H). About 10% of the enol form is observed in the NMR.

Step B 5-(6-Methoxy-2-naphthyl)-2,4-dihydro-3H-pyrazol-3-one. Ethyl 3-(6-methoxy-2-naphthyl)-3-oxopropanoate (5.0 g, 18.3 mmol) and anhydrous hydrazine (0.63 ml 20 mmol) were refluxed in HOAc (100 ml) for 3 hours. Solvent was removed under reduced pressure, and the residue was washed with DCM and collected by filtration to give 5-(6-methoxy-2-naphthyl)-2,4-dihydro-3H-pyrazol-3-one as an off-white solid. This compound exists in the enol form in DMSO. NMR (500 MHz, DMSO-$d_6$) δ: 3.87 (s, 3H); 5.95 (s, 1H); 7.17 (dd, J=2.7 Hz, 9.0 Hz, 1H); 7.31 (d, J=2.7 Hz, 1H); 7.74~7.84 (m, 3H); 8.11 (br s, 1H); 9.66 (br s, 1H); 12 (br, 1H). MS $C_{14}H_{12}N_2O_2$ Cald: 240.09, Obsd: (M+1) 241.08.

Step C 3-(6-Methoxy-2-naphthyl)-1H-pyrazol-5-yl trifluoromethanesulfonate. 3-(6-Methoxynaphth-2-yl)-5-pyrazolin-5-one (1.58 g, 6.58 mmol) and pyridine (1.62 ml, 20 mmol) were dissolved in THF (20 ml) at −78° C. Triflic anhydride (1.68 ml, 10 mmol) was added via syringe. The cooling bath was removed, and the reaction mixture was stirred for 2 hours. The mixture was cooled down to −78° C. and diluted with ethyl acetate (50 ml) and 2N HCl (10 ml). The ethyl acetate layer was washed with dilute HCl 2×, brine 2×. Evaporation of solvent left a purple residue, which was purified by column chromatography ($SiO_2$, 0-2.5% ethyl acetate in DCM) to give 3-(6-methoxy-2-naphthyl)-1H-pyrazol-5-yl trifluoromethanesulfonate as a white solid. NMR (500 MHz, DMSO-$d_6$) δ: 3.89 (s, 3H); 6.93 (d, J=2.2 Hz, 1H); 7.23 (dd, J=2.7 Hz, 8.8 Hz, 1H); 7.37 (d, J=2.7 Hz, 1H); 7.82~7.86 (m, 2H); 7.92 (d, J=8.7 Hz, 1H); 8.82 (s, 1H). MS $C_{15}H_{11}F_3N_2O_4S$, Cald: 372.04; Obsd (M+1): 373.06.

Step D tert-Butyl N-(4-acetylbenzoyl)-β-alaninate. A solution of NaOH (1.7 g/12 ml) was added to methyl 4-acetylbenzoate (5.04 g, 28.3 mmol) in MeOH-dioxane (2:1, 60 ml). After stirring at room temperature for 12 hr, the mixture was acidified with 5N HCl, and extracted with ethyl acetate. The organic layer was washed with brine, dried over $Na_2SO_4$. Evaporation of solvent gave 4-acetylbenzoic acid as a white solid.

4-Acetylbenzoic acid (2.45 g, 14.9 mmol), beta-alanine t-butyl ester hydrochloride (4.0 g, 22 mmol), DIEA (3.9 ml, 22 mmol) and DMAP (100 mg) were dissolved in DCM (100 ml). EDC hydrochloride (3.5 g, 18 mmol) was added in portions. Additional EDC (0.7 g) was added one hour later to complete the reaction. After a total of 3 hours, the reaction was partitioned between ethyl acetate and 0.5 N HCl. The organic layer was washed with 0.5 N HCl 3×, 5% $K_2CO_3$ 2×, brine 2×. Evaporation of solvent, and chromatography over $SiO_2$ (10-20% ethyl acetate in DCM) afforded tert-butyl N-(4-acetylbenzoyl)-β-alaninate as a while solid. NMR (500 MHz, $CD_3OD$) δ: 1.44 (s, 9H); 2.57 (t, J=7.0 Hz, 2H); 2.63 (s, 3H); 3.61 (t, J=7.0 Hz, 2H); 7.89 (d, J=8.5 Hz, 2H); 8.05 (d, J=8.5 Hz, 2H).

Step E tert-Butyl N-[4-(1-hydroxyethyl)benzoyl]-β-alaninate. Sodium borohydride (0.28 g, 7.4 mmol) was added as solid to a solution of tert-butyl N-(4-acetylbenzoyl)-β-alaninate (2.11 g, 7.24 mmol) in MeOH (50 ml). After stirring at room temperature for 30 min, the reaction was quenched by adding ethyl acetate (150 ml) and 2N HCl (50 ml). The organic layer was washed with 1 NHCl 2×, brine 2×, and dried over $Na_2SO_4$. Evaporation of solvent and vacuum drying afforded tert-butyl N-[4-(1-hydroxyethyl)benzoyl]-β-alaninate as a colorless oil. NMR ($CDCl_3$) δ: 1.46 (s, 9H); 1.49 (d, J=6.6 Hz, 3H); 2.55 (t, J=6.0 Hz, 2H); 3.67 (q, J=6.0 Hz, 2H); 4.94 (q, J=6.6 Hz, 1H); 6.88 (br, 1H); 7.42 (d, J=8.2 Hz, 2H); 7.72 (d, J=8.2 Hz, 2H). MS $C_{16}H_{23}NO_4$ Cald: 293.16; Obsd: (M+Na) 316.12.

Step F tert-Butyl N-{4-[1-(5-(6-methoxy-2-naphthyl)-3-{[(trifluoromethyl)sulfonyl]oxy}-1H-pyrazol-1-yl)ethyl]benzoyl}-β-alaninate. 3-(6-Methoxy-2-naphthyl)-1H-pyrazol-5-yl trifluoromethanesulfonate (1.36 g, 3.65 mmol), tert-butyl N-[4-(1-hydroxyethyl)benzoyl]-β-alaninate (1.2 g, 4.02 mmol), and triphenylphosphine (1.44 g, 5.48 mmol) were suspended in DCM (25 ml). Diisopropyl azodicarboxylate (0.87 ml, 4.38 mmol) was added slowly. The mixture was stirred for 2 hr and then concentrated to ~10 ml. This residue was chromatographed ($SiO_2$, 25-30% ethyl acetate gradient) to give 0.727 g of tert-butyl N-{4-[1-(3-(6-methoxy-2-naphthyl)-5-{[(trifluoromethyl)sulfonyl]oxy}-1H-pyrazol-1-yl)ethyl]benzoyl}-β-alaninate, NMR (500 MHz, $CDCl_3$) δ: 1.45 (s, 9H); 2.01 (d, J=7.1 Hz, 3H); 2.53 (t, J=5.9 Hz, 2H); 3.67 (q, J=5.9 Hz, 2H); 3.94 (s, 3H); 5.56 (q, J=7.1 Hz, 1H); 6.54 (s, 1H); 6.78 (br, 1H); 7.16 (br, 1H); 7.17 (dd, J=2.6 Hz, 9 Hz, 1H); 7.41 (d, J=8.4 Hz, 2H); 7.74 (d, J=8.4 Hz, 2H); 7.78 (d, J=8.4 Hz, 1H); 7.79 (d, J=8.5 Hz, 1H); 7.93 (dd, J=1.8 Hz, 8.5 Hz, 1H); 8.14 (d, J=1.6 Hz, 1H). MS $C_{31}H_{32}F_3N_3O_7S$ Cald: 647.19; Obsd (M+Na): 670.02 and 1.165 g of tert-butyl N-{4-[1-(5-(6-methoxy-2-naphthyl)-3-{[(trifluoromethyl)sulfonyl]oxy}-1H-pyrazol-1-yl)ethyl]benzoyl}-β-alaninate. NMR (500 MHz, $CDCl_3$) δ: 1.46 (s, 9H); 1.85 (d, J=7.1 Hz, 3H); 2.55 (t, J=5.8 Hz, 2H); 3.68 (q, J=5.8 Hz, 2H); 3.95 (s, 3H); 5.52 (q, J=7.1 Hz, 1H); 6.23 (s, 1H); 6.85 (br, 1H); 7.16 (d, J=2.6 Hz, 1H); 7.21 (dd, J=2.6 Hz, 8.7 Hz, 1H); 7.22 (d, J=8.4 Hz, 2H); 7.24 (dd, J=1.5 Hz, 8.4 Hz, 1H); 7.62 (d, J=1.5 Hz, 1H); 7.67 (d, J=8.7 Hz, 1H); 7.71 (d, J=8.3 Hz, 2H); 7.76 (d, J=8.4 Hz, 1H). MS $C_{31}H_{32}F_3N_3O_7S$ Cald: 647.19; Obsd (M+Na): 670.20.

Step G N-(4-{1-[3-(2,5-Dichlorophenyl)-5-(6-methoxy-2-naphthyl)-1H-pyrazol-1-yl]ethyl}benzoyl)-β-alanine. tert-Butyl N-{4-[1-(5-(6-methoxy-2-naphthyl)-3-{[(trifluoromethyl)sulfonyl]oxy}-1H-pyrazol-1-yl)ethyl]benzoyl}-β-alaninate (26 mg, 0.04 mmol), 2,-5-dichlorophenylboronic acid (15 mg, 0.08 mmol), and $PdCl_2$(dppf) (12 mg, 0.014 mmol), were suspended in toluene (0.6 ml) in a glass tube. A solution of $Cs_2CO_3$ (5 M, 25 ul) was added. The mixture was deoxygenated by vacuum-$N_2$ fill cycles, and heated in microwave reactor to 140° C. for 10 min. The reaction mixture was filtered through a glass-fiber plug, and solvent removed under reduced pressure. The residue was dissolved in $CH_3CN$—$H_2O$, and purified by reverse phase preparatory HPLC. The intermediate ester thus obtained was de-protected by treatment with TFA-DCM (1:2, 1 ml) for 30 min. Evaporation of solvent and lyophilization from $CH_3CN$—$H_2O$ yielded N-1-(4-(2-hydroxycarbonylethylaminocarbonyl)phenyl)ethyl-3-(2,5-dichlorophenyl)-5-(6-methoxynaphth-2-yl)pyrazole as a fine powder. NMR (500 MHz, DMSO-$d_6$) δ: 1.90 (d, J=6.9 Hz, 3H); 2.47 (t, J=7.1 Hz, 2H); 3.41 (q, J=7.1 Hz, 2H); 3.89 (s, 3H); 5.79 (q, J=6.9 Hz, 1H); 7.02 (s, 1H); 7.22 (d, J=8.4 Hz, 2H); 7.23 (d, J=9.0 Hz, 1H); 7.39 (d, J=2.6 Hz, 1H); 7.44 (dd, J=1.7 Hz, 8.3 Hz, 1H); 7.47 (dd, J=2.6 Hz, 8.6 Hz, 1H); 7.61 (d, J=8.6 Hz, 1H); 7.74 (d, J=8.4 Hz, 2H); 7.83 (d, J=9.0 Hz, 1H); 7.88 (d, J=1.7 Hz, 1H); 7.90 (d, J=8.6 Hz, 1H); 7.92 (d, J=2.6 Hz, 1H). MS $C_{32}H_{27}Cl_2N_3O_4$ Cald: 587.14; Obsd (M+1), 588.21.

Racemic N-(4-{1-[3-(2,5-dichlorophenyl)-5-(6-methoxy-2-naphthyl)-1H-pyrazol-1-yl]ethyl}benzoyl)-β-alanine prepared in Example 3 was separated into its enantiomers by chromatography using a ChiralPak AS column (10×250 mm), eluting with 40% MeOH:CO$_2$ (0.1% TFA) at 10 mL/min, 40° C. to give Example 82 (Table 3) and Example 106 (Table 4). Stereochemical assignment was tentative based on comparison of biological data with other analogues. This also applies to Examples 69, 83, 89, and 107.

Generic Synthesis of Pyrazoles, Method C

EXAMPLE 4

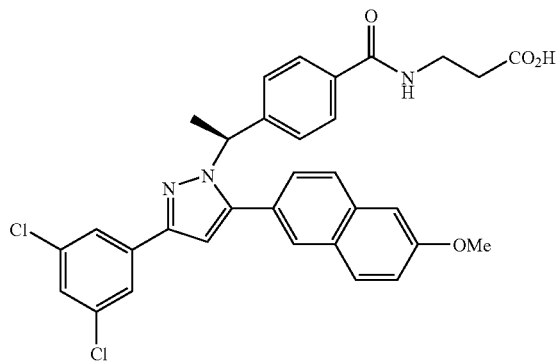

Step A Ethyl 4-{(1S)-1-[3-(3,5-dichlorophenyl)-5-oxo-4,5-dihydro-1H-pyrazol-1-yl]ethyl}benzoate Ethyl 3-(3,5-dichlorophenyl)-3-oxopropanoate (4.2 g, 16.1 mmol) and {(1S)-1-[4-(ethoxycarbonyl)phenyl]ethyl}hydrazinium trifluoroacetate (5.2 g, 16.1 mmol) were heated in dry acetonitrile (100 ml) to 85° C. for 1 hr. The solvent was removed under reduced pressure, and the residue purified by column chromatography (SiO$_2$, 20% ethyl acetate in hexanes) to give ethyl 4-{(1S)-1-[3-(3,5-dichlorophenyl)-5-oxo-4,5-dihydro-1H-pyrazol-1-yl]ethyl}benzoate as a white solid. NMR (500 MHz, CDCl$_3$) δ: 1.38 (t, J=7.1 Hz, 3H); 1.78 (d, J=7.0 Hz, 3H); 3.55 (d, J 22.6 Hz, 1H); 3.60 (d, J=22.6 Hz, 1H); 4.36 (q, J=7.1 Hz, 2H); 5.57 (q, J=7.0 Hz, 1H); 7.39 (t, J=1.9 Hz, 1H); 7.50 (d, J=8.4 Hz, 2H); 7.52 (d, J=1.9 Hz, 2H); 8.02 (d, J=8.4 Hz, 2H). MS C$_{20}$H$_{18}$Cl$_2$N$_2$O$_3$ Cald: 404.07; Obsd (M+1): 405.20.

Step B Ethyl 4-[(1S)-1-(3-(3,5-dichlorophenyl)-5-{[(trifluoromethyl)sulfonyl]oxy}-1H-pyrazol-1-yl)ethyl]benzoate. Ethyl 4-{(1S)-1-[3-(3,5-dichlorophenyl)-5-oxo-4,5-dihydro-1H-pyrazol-1-yl]ethyl}benzoate (4.93 g, 12.2 mmol), and triethylamine (8.5 ml, 61 mmol) were dissolved in THF (100 ml) at −78° C. Triflic anhydride (4.1 ml, 24.5 mmol) was added. The cooling bath was removed and reaction mixture was stirred for 1 h. Ethyl acetate was added (100 ml), and the organic phase was washed with water, 1N HCl 2×, and brine 2×. Flash column chromatography (SiO$_2$, 0-5% ethyl acetate in hexanes) yielded ethyl 4-[(1S)-1-(3-(3,5-dichlorophenyl)-5-{[(trifluoromethyl)sulfonyl]oxy}-1H-pyrazol-1-yl)ethyl]benzoate as a colorless oil. NMR (500 MHz, CDCl$_3$) δ: 1.38 (t, J=7.1 Hz, 3H); 1.98 (d, J=7.0 Hz, 3H); 4.36 (q, J=7.1 Hz, 2H); 5.55 (q, J=7.0 Hz, 1H); 6.43 (s, 1H); 7.33 (t, J=1.9 Hz, 1H); 7.36 (d, J=8.4 Hz, 2H); 7.68 (d, J=1.9 Hz, 2H); 8.02 (d, J=8.4 Hz, 2H).

Step C Ethyl 4-{(1S)-1-[3-(3,5-dichlorophenyl)-5-(6-methoxy-2-naphthyl)-1H-pyrazol-1-yl]ethyl}benzoate. Ethyl 4-[(1S)-1-(3-(3,5-dichlorophenyl)-5-{[(trifluoromethyl)sulfonyl]oxy}-1H-pyrazol-1-yl)ethyl]benzoate (2.15 g, 4.0 mmol), 6-methoxy-2-naphthylboronic acid (1.18 g, 6.0 mmol) and triethylamine (1.2 ml, 8.0 mmol) were dissolved in dimethoxyethane (40 ml) in a thick-wall tube. The reaction mixture was purged with N$_2$ for 15 min. Catalyst Pd(PPh$_3$)$_4$ (350 mg, 8%) was added, and the test tube was heated in a microwave reactor to 100° C. for 15 min. The solvent was removed under reduced pressure, and the residue partitioned between ethyl acetate and IN HCl. The organic layer was washed with 0.5 NH$_4$Cl 2×, brine 2×, dried over Na$_2$SO$_4$, and filtered through a Celite pad. The crude product was purified by column chromatography (SiO$_2$, 10-15% ethyl acetate in hexanes) to give ethyl 4-{(1S)-1-[3-(3,5-dichlorophenyl)-5-(6-methoxy-2-naphthyl)-1H-pyrazol-1-yl]ethyl}benzoate as a dry film. NMR (500 MHz, CDCl$_3$) δ: 1.38 (t, J=7.1 Hz, 3H); 1.96 (d, J=7.0 Hz, 3H); 3.95 (s, 3H; 4.37 (q, J=7.1 Hz, 2H); 5.59 (q, J=7.0 Hz, 1H); 6.65 (s, 1H); 7.17 (d, J=2.6 Hz, 1H); 7.20 (dd, J=2.6, 8.9 Hz, 1H); 7.28 (d, J=8.4 Hz, 2H); 7.29 (dd, J=1.8, 8.5 Hz, 1H); 7.30 (t, J=1.9 Hz, 1H); 7.63 (d, J=1.8 Hz, 1H); 7.67 (d, J=8.9 Hz, 1H); 7.76 (d, J=8.5 Hz, 1H); 7.80 (d, J=1.9 Hz, 2H); 7.99 (d, J=8.4 Hz, 2H); MS C$_{31}$H$_{26}$Cl$_2$N$_2$O$_3$ Cald: 544.13; Obsd: 545.15.

Step D 4-{(1S)-1-[3-(3,5-dichlorophenyl)-5-(6-methoxy-2-naphthyl)-1H-pyrazol-1-yl]ethyl}benzoic acid. Ethyl 4-{((1S)-1-[3-(3,5-dichlorophenyl)-5-(6-methoxy-2-naphthyl)-1H-pyrazol-1yl]ethyl}benzoate (3.53 g, 6.48 mmol) was dissolved in MeOH-dioxane (1:1, 100 ml), and a solution of NaOH(1.2 g, excess)/water (10 ml) was added. The reaction was stirred at room temperature overnight. After concentrating the reaction mixture to 50 ml, it was acidified with 2N HCl and extracted with ethyl acetate. The organic layer was washed with brine 2× and dried over Na$_2$SO$_4$. Evaporation of solvent and vacuum drying gave 4-{(1S)-1-[3-(3,5-dichlorophenyl)-5-(6-methoxy-2-naphthyl)-1H-pyrazol-1-yl]ethyl}benzoic acid as a white powder. NMR (500 MHz, CDCl$_3$) δ: 1.97 (d, J=7.0 Hz, 3H); 3.95 (s, 3H); 5.61 (q, J=7.0 Hz, 1H); 6.66 (s, 1H); 7.17 (d, J=2.5 Hz, H); 7.21 (dd, J=2.5, 9.0 Hz, 1H) 7.29 (dd, J=1.6, 8.4 Hz, 1H); 7.31 (t, J=1.9 Hz, 1H); 7.32 (d, J=8.4 Hz, 2H); 7.63 (d, J=1.6 Hz, 1H); 7.67 (d, J=9.0 Hz, 1H); 7.77 (d, J=8.4 Hz, 1H); 7.80 (d, J=1.9 Hz, 2H); 8.05 (d, J=8.4 Hz, 2H).

Step E N-(4-{(1S)-1-[3-(3,5-Dichlorophenyl)-5-(6-methoxy-2-naphthyl)-1H-pyrazo-1-yl]ethyl}benzoyl)-β-alanine. 4-{(1S)-1-[3-(3,5-Dichlorophenyl)-5-(6-methoxy-2-naphthyl)-1H-pyrazol-1-yl]ethyl}benzoic acid (3.5 g, 6.76 mmol), beta-alanine t-butyl ester hydrochloride (3.7 g, 20 mmol), DIEA (3.53 ml, 20 mmol), and DMAP (40 mg, 5%) were dissolved in DCM (50 ml), followed by addition of solid EDC HCl (1.6 g, 8.1 mmol). More EDC HCl (1.8 g) was added after one hour. The reaction was completed in about 3 hr as monitored by LC-MS. Ethyl acetate was added to the reaction mixture, and this was washed with 1N HCl 3× and brine 2×. The crude product was then purified by column chromatography (SiO$_2$, 0-6% ethyl acetate in DCM) to give tert-butyl N-(4-{(1S)-1-[3-(3,5-dichlorophenyl)-5-(6-methoxy-2-naphthyl)-1H-pyrazol-1-yl]ethyl}benzoyl)-β-alaninate as a dry foam. NMR (500 MHz, DMSO-d$_6$) δ: 1.36 (s, 9H); 1.90 (d, J=6.9 Hz, 3H); 2.44 (t, J=6.8 Hz, 2H); 3.41 (q, J=6.8 Hz, 2H); 3.89 (s, 3H); 5.76 (q, J=6.9 Hz, 1H); 7.15 (s, 1H); 7.21 (d, J=8.4 Hz, 2H); 7.22 (dd, J=2.6, 9.0 Hz, 1H); 7.38 (d, J=2.6 Hz, 1H); 7.43 (dd, J=1.9, 8.5 Hz, 1H); 7.55 (t, J=1.9 Hz, 1H); 7.71 (d, J=8.4 Hz, 2H); 7.81 (d, J=9.0 Hz, H); 7.85 (d, J=1.9 Hz, 1H); 7.90 (d, J=8.5 Hz, 1H); 7.92 (d, J=1.9 Hz, 2H); 8.44 (t, J=5.2 Hz, 1H).

The t-butyl ester was de-protected in TFA-DCM (1:2, 200 ml) for 30 min. Evaporation of solvent and vacuum drying left an oily residue which was lyophilized from CH$_3$CN:H$_2$O (1:1, 200 ml) to give N-(4-{(1S)-1-[3-(3,5-dichlorophenyl)-5-(6-methoxy-2-naphthyl)-1H-pyrazol-1-yl]ethyl}benzoyl)-

β-alanine as a white powder. ([α]$_D^{20}$=+12° (c 2, MeOH)) NMR (500 MHz, DMSO-d$_6$) δ: 1.90 (d, J=7.0 Hz, 3H); 2.47 (t, J=7 Hz, 2H); 3.41 (q, J=7 Hz, 2H); 3.89 (s, 3H); 5.76 (q, J=7.0 Hz, 1H); 7.16 (s, 1H); 7.20 (d, J=8.4 Hz, 2H); 7.23 (dd, J=2.6, 9.0 Hz, 1H); 7.39 (d, 2.6 Hz, 1H); 7.43 (dd, J=1.7, 8.4 Hz, 1H); 7.56 (t, J=1.9 Hz, 1H); 7.72 (d, J=8.4 Hz, 2H); 7.83 (d, J=9.0 Hz, 1H); 7.86 (d, J=1.7 Hz, 1H); 7.91 (d, J=8.4 Hz, 1H); 7.93 (d, J=1.9 Hz, 2H); 8.44 (t, J=5.6 Hz, 1H). MS C$_{32}$H$_{27}$Cl$_2$N$_3$O$_4$ Cald: 587.14; Obsd (M+1): 588.24

EXAMPLE 5

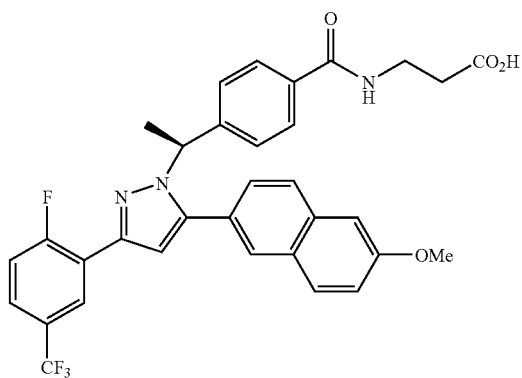

Step A Ethyl 3-[2-fluoro-5-(trifluoromethyl)phenyl]-3-oxopropanoate. Potassium ethyl malonate (10.2 g, 60 mmol), MgCl$_2$ (6.3 g, 66 mmol), and triethylamnine (28 ml, 200 mmol) were suspended in dry ethyl acetate (200 ml) and heated to 40° C. for 15 hr. A solution of 2-fluoro-5-trifluoromethylbenzoyl chloride (10 g, 44.1 mmol) in ethyl acetate (40 ml) was dropped in slowly (in about one hour). After another hour, the mixture was treated with 2N HCl (200 ml). The organic layer was washed with 0.5 N HCl 2×, 5% K$_2$CO$_3$ 2×, brine 2×, and dried over Na$_2$SO$_4$. Evaporation of the solvent and vacuum drying afforded ethyl 3-[2-fluoro-5-(trifluoromethyl)phenyl]-3-oxopropanoate as a pale yellow oil. NMR (500 MHz, CDCl$_3$) δ: 1.25 (t, J=7.4 Hz, 3H); 1.32*; 4.00 (d, J$_{F-H}$=3 Hz, 2H); 4.21 (q, J=7.4 Hz, 2H); 5.8*; 7.22*; 7.29 (t, J=10.3 Hz, 1H); 7.66*; 7.82 (br, 1H); 8.14*; 8.24 (d, J=6.4 Hz, 1H). Enol form* exists in about 35%.

Step B Ethyl 4((1S)-1-{3-[2-fluoro-5-(trifluoromethyl)phenyl]-5-oxo-4,5-dihydro-1H-pyrazol-1-yl}ethyl)benzoate. Ethyl 3-[2-fluoro-5-(trifluoromethyl)phenyl]-3-oxopropanoate (3 g, 9.7 mmol) and {(1S)-1-[4-(ethoxycarbonyl)phenyl]ethyl}hydrazinium trifluoroacetate (2.64 g, 8.2 mmol) were heated in dry acetonitrile (150 ml) to 85° C. for 8 hr. Solvent was evaporated and the residue purified by flash column chromatograph (SiO$_2$, 25% ethyl acetate in hexanes) to give ethyl 4-((1S)-1-{3-[2-fluoro-5-(trifluoromethyl)phenyl]-5-oxo-4,5-dihydro-1H-pyrazol-1-yl}ethyl)benzoate as a white solid. NMR (500 MHz, CDCl$_3$) δ: 1.38 (t, J=7.1, 3H); 1.82 (d, 7.2 Hz, 3H); 3.81 (dd, J=3 Hz, 23.9 Hz, 1H); 3.87 (d, J=3 Hz, 23.9 Hz, 1H); 4.36 (q, J=7.1 Hz, 2H); 5.60 (q, J=7.2 Hz, 1H); 7.25 (t,J=9.5 Hz, 1H); 7.51 (d, J=8.4 Hz, 2H); 7.66 (br, 1H); 8.03 (d, J=8.4 Hz, 2H); 8.25 (dd, J=1.8 Hz, 6.4 Hz, 1H). MS C$_{21}$H$_{18}$F$_4$N$_2$O$_3$ Cald: 422.13; Obsd (M+1): 423.09.

Step C Ethyl 4-[(1S)-1-(3-[2-fluoro-5-(trifluoromethyl)phenyl]-5-{[(trifluoromethyl)-sulfonyl]oxy}-1H-pyrazol-1-yl)ethyl]benzoate. Ethyl 4-((1S)-1-{3-[2-fluoro-5-(trifluoromethyl)phenyl]-5-oxy-4,5-dihydro-1H-pyrazol-1-yl}ethyl)benzoate (1.42 g, 3.36 mmol) and triethylamine (2.4 ml, 17.3 mmol) were dissolved in THF (25 ml) and cooled to −78° C. Triflic anhydride (1.1 ml, 6.6 mmol) was added. The cooling bath was removed and reaction mixture stirred for 1 h. Ethyl acetate (100 ml) was added, and the organic phase washed with water, 1N HCl 2×, and brine 2×. Flash column chromatography (SiO$_2$, 0-5% ethyl acetate in hexanes) yielded ethyl 4-[(1S)-1-(3-[2-fluoro-5-(trifluoromethyl)phenyl]-5-{[(trifluoromethyl)sulfonyl]oxy}-1H-pyrazol-1-yl) ethyl]benzoate as a colorless oil. NMR (500 MHz, CDCl$_3$) δ: 1.38 (t, J=7.1 Hz, 3H); 2.01 (d, J=7.0 Hz, 3H); 4.36 (q, J=7.1 Hz, 2H); 5.59 (q, j=7.0 Hz, 1); 6.64 (d, J$_{F-H}$=3.5 Hz, 1H); 7.25 (t, J=9.7 Hz, 1H); 7.37 (d, J=8.3 Hz, 2H); 7.59 (m, 1H); 8.03 (d, J=8.3 Hz, 2H); 8.38 (dd, J=2.7 Hz, 6.7 Hz, 1H). MS C$_{22}$H$_{17}$F$_7$N$_2$O$_5$S Cald: 554.07; Obsd (M+1): 555.16.

Step D Ethyl 4-{(1S)-1-[3-[2-fluoro-5-(trifluoromethyl)phenyl]-5-(6-methoxy-2-naphthyl)-1H-pyrazol-1-yl] ethyl}benzoate. Ethyl 4-[(1S)-1-(3-[2-fluoro-5-(trifluoromethyl)phenyl]-5-{[(trifluoromethyl)sulfonyl]oxy}-1H-pyrazol-1-yl)ethyl]benzoate (1.05 g, 1.90 mmol), 6-methoxy-2-naphthylboronic acid (0.43 g, 2.1 mmol), and triethylamine (0.53 ml, 3.8 mmol) were dissolved in DME (20 ml). After deoxygenation (vacuum-N$_2$ cycles) Pd(PPh$_3$)$_4$ (85 mg, 4% mol) was added. The mixture was deoxygenated again and heated in microwave reactor to 100° C. for 15 min. The reaction mixture was filtered through a Celite pad, concentrated and purified by flash column chromatography (SiO$_2$, 5-20% ethyl acetate in hexane gradient) to give ethyl 4-{(1S)-1-[3-[2-fluoro-5-(trifluoromethyl)phenyl]-5-(6-methoxy-2-naphthyl)-1H-pyrazol-1-yl]ethyl}benzoate as colorless gel. NMR (500 MHz, CDCl$_3$) δ: 1.38 (t, J=7.1 Hz, 3H); 1.99 (d, J=7.1 Hz, 3H); 3.96 (s, 3H); 4.37 (q, J=7.1 Hz, 2H); 5.64 (q, J=7.1 Hz, 1H); 6.87 (d, J$_{F-H}$=4.2 Hz, 1H); 7.17 (d, J=2.5 Hz, 1H); 7.20 (dd, J=2.5 Hz, 8.9 Hz, 1H); 7.25 (t, J=9.5 Hz, 1H); 7.30 (d, J=8.4 Hz, 2H); 7.32 (dd, J=1.5 Hz, 8.4 Hz, 1H); 7.56 (m, 1H); 7.66 (d, J=1.5 Hz, 1H); 7.68 (d, J=8.9 Hz, 1H); 7.77 (d, J=8.4 Hz, 1H); 8.00 (d, J=8.4 Hz, 2H); 8.48 (dd, J=2.7 Hz, 6.8 Hz, 1H). MS C$_{32}$H$_{26}$F$_4$N$_2$O$_3$ Cald: 562.19; Obsd (M+1): 563.33.

Step E 4-{(1S)-1-[3-[2-Fluoro-5-(trifluoromethyl)phenyl]-5-(6-methoxy-2-naphthyl)-1H-pyrazol-1-yl]ethyl}benzoic acid. Ethyl 4-{(1S)-1-[3-[2-fluoro-5-(trifluoromethyl)phenyl]-5-(6-methoxy-2-naphthyl)-1H-pyrazol-1-yl]ethyl}benzoate (2.87 g, 5.11 mmol) was dissolved in MeOH-dioxane (1:2, 60 ml) and treated with NaOH (2.5 g, excess) in water (20 ml). The mixture slowly cleared with stirring, and was left overnight. The reaction mixture was first concentrated to ~30 ml, acidified with 2N HCl and extracted with ethyl acetate. The organic layer was washed with brine 2× and dried over Na$_2$SO$_4$. Evaporation of solvent and vacuum drying afforded 4-{(1S)-1-[3-[2-fluoro-5-(trifluoromethyl)phenyl]-5-(6-methoxy-2-naphthyl)-1H-pyrazol-1-yl]ethyl}benzoic acid as colorless dry foam. NMR (500 MHz, CDCl$_3$) δ: 2.00 (d, J=7.0 Hz, 3H); 3.95 (s, 3H); 5.65 (q, J=7.0 Hz, 1H); 6.88 (d, J$_{F-H}$=4.2 Hz, 1H); 7.17 (d, J=2.5 Hz, 1H); 7.20 (dd, J=2.5 Hz, 8.9 Hz, 1H); 7.26 (t, J=8.6 Hz, 1H); 7.31 (dd, J=1.8 Hz, 8.5 Hz, 1H); 7.32 (d, J=8.4 Hz, 2H); 7.56 (m, 1H); 7.66 (d, J=1.8 Hz, 1H); 7.68 (d, J=8.9 Hz, 1H); 7.77 (d, J=8.5 Hz, 1H); 8.06 (d, J=8.4 Hz, 2H); 8.48 (dd, J=2.9 Hz, 6.9 Hz, 1H). MS C$_{30}$H$_{22}$F$_4$N$_2$O$_3$ Cald: 534.16; Obsd (M+1): 535.17.

Step F N-(4-{(1S)-1-[3-[2-Fluoro-5-(trifluoromethyl)phenyl]-5-(6-methoxy-2-naphthyl)-1H-pyrazol-1-yl] ethyl}benzoyl)-β-alanine. 4-{(1S)-1-[3-[2-fluoro-5-(trifluoromethyl)phenyl]-5-(6-methoxy-2-naphthyl)-1H-pyrazol-1-yl]ethyl}benzoic acid (2.93 g, 5.48 mmol), beta-alanine t-butyl ester hydrochloride (2.73 g, 15 mmol), and DIEA (3.5 ml, 20 mmol) were dissolved in DMF (35 ml), followed by slow addition of PyBOP (2.93 g, 5.62 mmol) in DMF (10 ml). The reaction was stirred for 10 min, and diluted with ethyl acetate (200 ml), washed with 1N HCl 2×, 5% $K_2CO_3$ 2×, and brine 2×. The solvent was evaporated and resulting residue was purified by flash chromatography ($SiO_2$, 0-6% ethyl acetate in DCM gradient) to give tert-butyl N-(4-{(1S)-1-[3-[2-fluoro-5-(trifluoromethyl)phenyl]-5-(6-methoxy-2-naphthyl)-1H-pyrazol-1-yl]ethyl}benzoyl)-β-alaninate as a dry foam. NMR (500 MHz, DMSO-$d_6$) δ: 1.35 (s, 9H); 1.92 (d, J=6.9 Hz, 3H); 2.44 (t, J=7.0 Hz, 2H); 3.41 (q, J=7.0 Hz, 2H); 3.89 (s, 3H); 5.80 (q, J=6.9 Hz, 1H); 6.94 (d, $J_{F-H}$=3.8 Hz, 1H); 7.21 (d, J=8.3 Hz, 2H); 7.22 (dd, J=2.6 Hz, 9.0 Hz, 1H); 7.39 (d, J=2.6 Hz, 1H); 7.44 (dd, J=2.6 Hz, 8.5 Hz, 1H); 7.58 (t, J=9.7 Hz, 1H); 7.72 (d, J=8.3 Hz, 2H); 7.79 (m, 1H); 7.83 (d, J=9.0 Hz, 1H); 7.89 (d, J=2 Hz, 1H); 7.90 (d, J=8.5 Hz, 1H); 8.33 (dd, J=2.8 Hz, 6.6 Hz, 1H); 8.44 (t, J=5.5 Hz, NH). MS $C_{37}H_{35}F_4N_3O_4$ Cald: 661.26; Obsd (M+1): 662.29.

The t-butyl easter was deprotected with TFA-DCM (1:2, 300 ml) at room temperature for 30 min. After evaporation and vacuum drying, the residue was lyophilized from $CH_3CN:H_2O$ (1:1, 300 ml) to give N-(4-{(1S)-1-[3-[2-fluoro-5-(trifluoromethyl)phenyl]-5-(6-methoxy-2-naphthyl)-1H-pyrazol-1-yl]ethyl}benzoyl)-β-alanine as a fine powder. ($[\alpha]_D^{20}$=-6° (c 2, MeOH)). NMR (500 MHz, DMSO-$d_6$) δ: 1.92 (d, J=6.9 Hz, 3H); 2.47 (t, J=6.8 Hz, 2H); 3.41 (q, J=6.8 Hz, 2H); 3.89 (s, 3H); 5.80 (q, J=6.9 Hz, 1H); 6.94 (d, $J_{F-H}$=3.8 Hz, 1H); 7.20 (d, J=8.4 Hz, 2H); 7.23 (dd, J=2.8 Hz, 9.0 Hz, 1H); 7.39 (d, J=2.8 Hz, 1H); 7.44 (dd, J=2.0 Hz, 8.6 Hz, 1H); 7.58 (t, J=9.7 Hz, 1H); 7.73 (d, J=8.4 Hz, 2H); 7.79 (m, 1H); 7.84 (d, J=9.0 Hz, 1H); 7.89 (d, J=2.0 Hz, 1H); 7.90 (d, J=8.6 Hz, 1H); 8.33 (dd, J=2.8 Hz, 6.9 Hz, 1H); 8.45 (t, J=5.5 Hz, 1H NH). MS $C_{33}H_{27}F_4N_3O_4$ Cald: 605.19; Obsd (M+1): 606.32.

Following the procedures outlined for Examples 1-5 the compounds listed in Table 1-6 were prepared.

TABLE 1

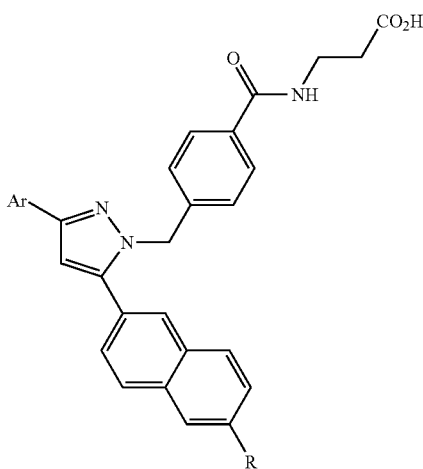

| Example | Ar | R | LC-MS data | Method |
|---|---|---|---|---|
| 6 | 3,5-diCF$_3$Ph | H | Cald: 611.16<br>Obsd: 612.36 | A |
| 7 | 3,5-diClPh | H | Cald: 543.11<br>Obsd: 544.28 | A |
| 8 | 3,5-diClPh | MeO | Cald: 573.12<br>Obsd: 574.22 | A |
| 9 | 4-CF$_3$OPh | MeO | Cald: 589.18<br>Obsd: 590.26 | A |
| 10 | 4-CF$_3$, 2-PrOPh | H | Cald: 601.22<br>Obsd: 602.38 | A |
| 11 | 4-CF$_3$, 2-PrOPh | MeO | Cald: 631.23<br>Obsd: 632.41 | A |
| 12 | 3,5-diClPh | CF$_3$O | Cald: 627.09<br>Obsd: 628.27 | A |
| 13 | 4-CF$_3$OPh | CF$_3$O | Cald: 643.15<br>Obsd: 644.32 | A |
| 14 | 4-CF$_3$, 2-PrOPh | CF$_3$O | Cald: 685.20<br>Obsd: 686.36 | A |
| 15 | 3-Cl, 2-EtOPh | MeO | Cald: 583.19<br>Obsd: 584.23 | B |
| 16 | 4-Cl, 3-FPh | MeO | Cald: 557.15<br>Obsd: 558.18 | B |
| 17 | 2,4-diFPh | MeO | Cald: 541.18<br>Obsd: 542.30 | B |
| 18 | 2-CF$_3$OPh | MeO | Cald: 589.18<br>Obsd: 590.21 | B |
| 19 | 2-EtOPh | MeO | Cald: 549.23<br>Obsd: 550.27 | B |
| 20 | 2-F, 5-CF$_3$Ph | MeO | * | B |
| 21 | 4-Cl, 2-EtOPh | MeO | * | B |

* Mass spectrometric data unavailable.

$^1$H NMR data for Example 20 - NMR(500 MHz, DMSO-$d_6$) δ: 2.46(t, J=7.1 Hz, 2H); 3.40(q, J=7.0 Hz, 2H); 3.88(s, 3H); 5.62(s, 2H); 7.03(d, J=3.7 Hz, 1H); 7.11(dd, J=8.1 Hz, 2H); 7.21(dd, J=2.5, 9.1 Hz, 1H); 7.37(d, J=2.5 Hz, 1H); 7.54(dd, J=1.9, 8.5 Hz, 1H); 7.60(t, J=9.6 Hz, 1H); 7.72(d, J=8.1 Hz, 2H); 7.79(m, 1H); 7.83(d, J=9.1 Hz, 1H); 7.89(d, J=8.5 Hz, 1H); 7.98(br s, 1H); 8.30(dd, J=2.7, 6.7 Hz, 1H); 8.45(t, NH, J=5.6 Hz, 1H).

$^1$H NMR data for Example 21 - NMR(500 MHz, DMSO-$d_6$) δ: 1.41(d, J=6.8 Hz, 3H); 2.46(t, J=7.0 Hz, 2H); 3.40(q, J=6.8 Hz, 2H); 3.88(s, 3H); 4.17(q, J=6.8 Hz, 2H); 5.53(s, 2H); 7.00(s, 1H); 7.05(dd, J=2.0, 8.3 Hz, 1H); 7.11(d, J=8.2 Hz, 2H); 7.17(d, J=2.0 Hz, 1H); 7.21(dd, J=2.5, 9.0 Hz, 1H); 7.36(d, J=2.5 Hz, 1H); 7.50(br d, J=8.5 Hz 1H); 7.71(d, J=8.2 Hz, 2H); 7.82(d, J=9.0 Hz, 1H); 7.89(d, J=8.5 Hz, 1H); 7.92(br s, 1H); 7.95(d, J=8.3 Hz, 1H); 8.45(t, NH, J=5.6 Hz, 1H).

TABLE 2

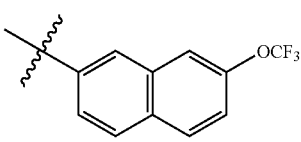

| Example | Ar | Ar¹ | LC-MS data | Method |
|---|---|---|---|---|
| 22 | 3,5-diClPh | 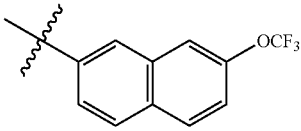 | Cald: 627.09<br>Obsd: 628.27 | A |
| 23 | 3,5-CF₃OPh | 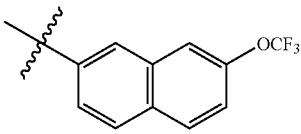 | Cald: 643.15<br>Obsd: 644.32 | A |
| 24 | 4-CF₃, 2-PrOPh | 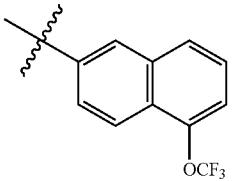 | Cald: 685.20<br>Obsd: 686.35 | A |
| 25 | 3,5-diClPh | 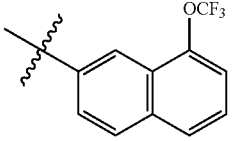 | * | A |
| 26 | 3,5-diClPh |  | * | A |

* MASS SPECTROMETRIC DATA UNAVARABLE.

¹H NMR DATA FOR EXAMPLE 25 - NMR(500 MHZ, DMSO-D₆) δ: 2.45(T, J=7.1 HZ, 2H); 3.40(Q, J=6 HZ, 2H); 5.61(S, 2H); 7.13(D, J=8.2 HZ, 2H); 7.35(S, 1H); 7.57(T, J=1.9 HZ, 1H); 7.63(BR D, J=7.8 HZ, 1H); 7.66(T, J=7.7 HZ, 1H); 7.72(D, J=8.2 HZ, 2H); 7.77(DD, J=1.7, 8.8 HZ, 1H); 7.92(D, J=1.9 HZ, 2H); 7.98(D, J=7.7 HZ, 1H); 8.15(D. J=8.8 HZ, 1H); 8.19(BR S, 1H); 8.45(T, NH, J=5.6 HZ, 1H).

¹H NMR DATA FOR EXAMPLE 26 - NMR(500 MHZ, DMSO-D₆) δ: 2.45(T, J=7.1 HZ, 2H); 3.41(Q, J=7 HZ, 2H); 5.57(S, 2H); 7.14(D, J=8.2 HZ, 2H); 7.39(S, 1H); 7.58(T, J=1.9 HZ, 1H); 7.61(BR D. J=8.0 HZ, 1H); 7.66(T, J=7.9 HZ, 1H); 7.76(D, J=8.3 HZ, 3H); 7.94(D, J=1.9 HZ, 2H); 8.02(BR S, 1H); 8.04(D, J=8.1 HZ, 1H); 8.18(D, J=8.3 HZ,1H); 8.47(T, NH, J=5.6 HZ,

TABLE 3

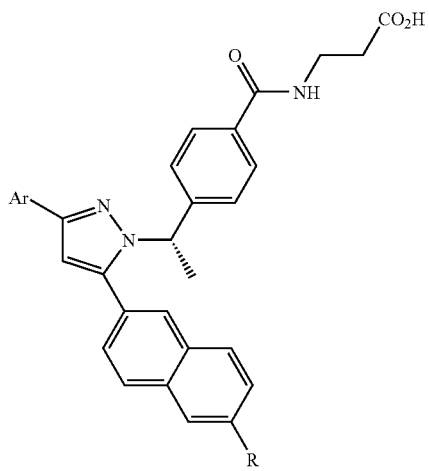

| Example | Ar | R | LC-MS data | Method |
|---|---|---|---|---|
| 27 | 4-Cl, 2-PrOPh | CF$_3$O | Cald: 665.19 Obsd: 666.32 | A |
| 28 | 4-Cl, 2-PrOPh | MeO | Cald: 611.22 Obsd: 612.03 | A |
| 29 | 5-Cl, 2-CF$_3$OPh | CF$_3$O | Cald: 691.13 Obsd: 691.88 | A |
| 30 | 5-Cl, 2-CF$_3$OPh | MeO | Cald: 637.16 Obsd: 638.12 | A |
| 31 | 3,5-diClPh | EtO | Cald: 601.15 Obsd: 602.06 | A |
| 32 | 4-CF$_3$OPh | MeO | Cald: 603.20 Obsd: 604.10 | A |
| 33 | 3,5-diClPh | CF$_3$ | Cald: 625.11 Obsd: 626.16 | A |
| 34 | 3,5-diClPh | Cl | Cald: 591.09 Obsd: 594.10 | A |
| 35 | 5-Cl, 2-CF$_3$OPh | CF$_3$ | Cald: 675.14 Obsd: 676.20 | A |
| 36 | 5-Cl, 2-CF$_3$OPh | Cl | Cald: 641.11 Obsd: 642.18 | A |
| 37 | 3,5-diClPh | Cl | Cald: 587.14 Obsd: 588.19 | A |
| 38 | 3,5-diClPh | CF$_3$O | Cald: 641.11 Obsd: 642.07 | A |
| 39 | 4-Cl, 2-CF$_3$OPh | MeO | Cald: 637.16 Obsd: 638.15 | A |
| 40 | 4-Cl, 2-CF$_3$OPh | CF$_3$O | Cald: 691.13 Obsd: 691.80 | A |
| 41 | 3,4,5-triFPh | MeO | Cald: 573.19 Obsd: 574.17 | A |
| 42 | 3,4,5-triFPh | CF$_3$O | Cald: 627.16 Obsd: 628.14 | A |
| 43 | 3-CF$_3$OPh | MeO | Cald: 603.20 Obsd: 604.23 | A |
| 44 | 3-CF$_3$OPh | CF$_3$O | Cald: 657.17 Obsd: 658.21 | A |
| 45 | 3-Cl, 4-FPh | MeO | Cald: 571.17 Obsd: 572.28 | A |
| 46 | 3-Cl, 4-FPh | CF$_3$O | Cald: 625.14 Obsd: 626.21 | A |
| 47 | 2-F, 4-CF$_3$Ph | MeO | Cald: 605.19 Obsd: 606.31 | A |
| 48 | 2-F, 4-CF$_3$Ph | CF$_3$O | Cald: 659.17 Obsd: 660.26 | A |
| 49 | 2-F, 4-CF$_3$Ph | EtO | Cald: 619.21 Obsd: 620.29 | A |
| 50 | 3-Cl, 4-FPh | EtO | Cald: 585.18 Obsd: 586.26 | A |
| 51 | 3-Cl, 4-FPh | CF$_3$ | Cald: 609.14 Obsd: 610.28 | A |
| 52 | 2-F, 4-CF$_3$Ph | CF$_3$ | Cald: 643.17 Obsd: 644.31 | A |
| 53 | 3,4,5-triFPh | CF$_3$ | Cald: 611.17 Obsd: 612.30 | A |
| 54 | 3-CF$_3$OPh | CF$_3$ | Cald: 641.17 Obsd: 642.35 | A |
| 55 | 3,4-diClPh | CF$_3$ | Cald: 625.11 Obsd: 626.28 | A |
| 56 | 2-F, 4-CF$_3$Ph | EtO | Cald: 619.21 Obsd: 620.25 | A |
| 57 | 2-F, 4-CF$_3$Ph | CF$_3$O | Cald: 659.17 Obsd: 660.21 | A |
| 58 | 3,5-diClPh | OH | Cald: 573.12 Obsd: 574.18 | A |
| 59 | 4-CF$_3$, 2-cPrCH$_2$OPh | MeO | Cald: 657.25 Obsd: 658.22 | A |
| 60 | 4-CF$_3$, 2-EtOPh | MeO | Cald: 631.23 Obsd: 632.06 | A |
| 61 | 4-CF$_3$, 2-cPentOPh | MeO | Cald: 671.26 Obsd: 672.18 | A |
| 62 | 4-Cl, 2-CF$_3$OPh | CF$_3$ | Cald: 675.14 Obsd: 676.19 | A |
| 63 | 3-Cl, 4-FPh | Cl | Cald: 575.12 Obsd: 576.20 | A |
| 64 | 2-F, 4-CF$_3$Ph | Cl | Cald: 609.14 Obsd: 610.20 | A |
| 65 | 3,4,5-triFPh | Cl | Cald: 577.14 Obsd: 578.20 | A |
| 66 | 3-CF$_3$OPh | Cl | Cald: 607.15 Obsd: 608.20 | A |
| 67 | 4-Cl, 2-CF$_3$OPh | Cl | Cald: 641.11 Obsd: 642.20 | A |
| 68 | 3,4-diClPh | Cl | Cald: 591.09 Obsd: 594.20 | A |
| 69 | 3,4-diClPh | MeO | Cald: 555.20 Obsd: 556.29 | A |
| 70 | 5-Cl, 2-FPh | MeO | Cald: 571.17 Obsd: 572.20 | A |
| 71 | 5-Cl, 2-FPh | CF$_3$O | Cald: 625.14 Obsd: 626.20 | A |
| 72 | 3-Cl, 4-MeOPh | MeO | Cald: 583.19 Obsd: 584.20 | A |
| 73 | 3-Cl, 4-EtOPh | MeO | Cald: 597.20 Obsd: 598.20 | A |
| 74 | 3-Cl, 4-PrOPh | MeO | Cald: 611.22 Obsd: 612.30 | A |
| 75 | 3-Cl, 4-cPrCH$_2$OPh | MeO | Cald: 623.22 Obsd: 642.30 | A |
| 76 | 3-Cl, 4-cPentOPh | MeO | Cald: 637.23 Obsd: 638.30 | A |
| 77 | 5-Cl, 2-MeOPh | MeO | Cald: 583.19 Obsd: 584.14 | A |
| 78 | 5-Cl, 2-EtOPh | MeO | Cald: 597.2 Obsd: 598.21 | A |
| 79 | 5-Cl, 2-PrOPh | MeO | Cald: 611.22 Obsd: 612.19 | A |
| 80 | 5-Cl, 2-cPrCH$_2$OPh | MeO | Cald: 623.22 Obsd: 624.19 | A |

TABLE 3-continued

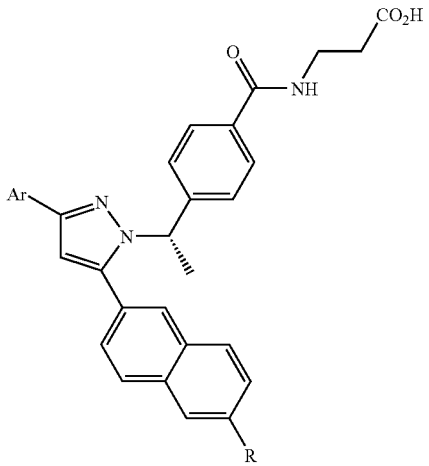

| Example | Ar | R | LC-MS data | Method |
|---|---|---|---|---|
| 81 | 5-Cl, 2-cPentOPh | MeO | Cald: 637.23 Obsd: 638.22 | A |
| 82 | 2,5-diClPh | MeO | Cald: 587.14 Obsd: 588.31 | A |
| 83 | 2,3,5-triClPh | MeO | Cald: 621.10 Obsd: 622.20 | A |
| 84 | 3-Cl, 4-MeOPh | Cl | Cald: 587.14 Obsd: 588.20 | A |
| 85 | 3-Cl, 4-EtOPh | Cl | Cald: 601.15 Obsd: 602.20 | A |
| 86 | 3-Cl, 4-PrOPh | Cl | Cald: 615.17 Obsd: 616.00 | A |
| 87 | 3-Cl, 4-cPrCH$_2$OPh | Cl | Cald: 627.17 Obsd: 628.20 | A |
| 88 | 3-Cl, 4-cPentOPh | Cl | Cald: 641.18 Obsd: 642.20 | A |
| 89 | 3-CF$_3$Ph | Cl | Cald: 587.20 Obsd: 588.39 | A |
| 90 | 2,5-diFPh | MeO | Cald: 555.20 Obsd: 556.25 | A |
| 91 | 2,5-diFPh | CF$_3$O | Cald: 609.17 Obsd: 610.24 | A |
| 92 | 2,4,5-diFPh | MeO | Cald: 573.19 Obsd: 574.30 | A |
| 93 | 2,4,5-diFPh | CF$_3$O | Cald: 627.16 Obsd: 628.20 | A |
| 94 | 2-F, 5-CF$_3$Ph | Cl | Cald: 609.14 Obsd: 610.30 | A |
| 95 | 4-Cl, 2-MeOPh | MeO | Cald: 583.19 Obsd: 584.30 | A |
| 96 | 4-Cl, 2-EtOPh | MeO | Cald: 597.20 Obsd: 598.30 | A |
| 97 | 4-Cl, 2-cPentOPh | MeO | Cald: 637.23 Obsd: 638.40 | A |
| 98 | 4-Cl, 2-cPrCH$_2$OPh | MeO | Cald: 623.22 Obsd: 624.30 | A |
| 99 | 4-Cl, 2-PrOPh | Cl | Cald: 615.17 Obsd: 616.30 | A |

TABLE 4

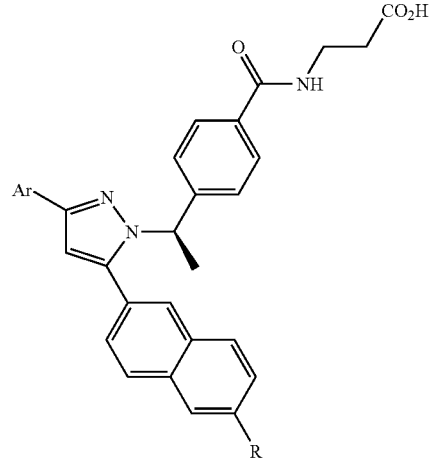

| Example | Ar | R | LC-MS data | Method |
|---|---|---|---|---|
| 100 | 4-Cl, 2-PrOPh | CF$_3$O | Cald: 665.19 Obsd: 666.32 | A |
| 101 | 4-Cl, 2-PrOPh | MeO | Cald: 611.22 Obsd: 612.37 | A |
| 102 | 5-Cl, 2-CF$_3$OPh | CF$_3$O | Cald: 691.13 Obsd: 691.90 | A |
| 103 | 5-Cl, 2-CF$_3$OPh | MeO | Cald: 637.16 Obsd: 638.16 | A |
| 104 | 3,5-diClPh | MeO | Cald: 587.14 Obsd: 588.26 | B |
| 105 | 3,5-diClPh | CF$_3$ | Cald: 625.11 Obsd: 626.28 | A |
| 106 | 2,5-diClPh | MeO | Cald: 587.14 Obsd: 588.31 | B |
| 107 | 2,3,5-diClPh | MeO | Cald: 621.10 Obsd: 622.20 | B |

TABLE 5

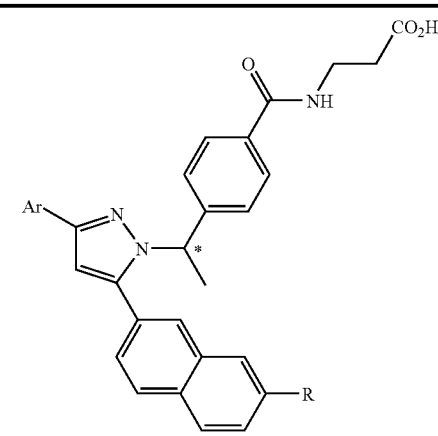

| Example | Ar | R | Stereo chemistry | LC-MS data | Method |
|---|---|---|---|---|---|
| 108 | 3,5-diClPh | CF$_3$O | S | Cald: 641.11 Obsd: 642.21 | A |
| 109 | 3,5-diClPh | CF$_3$O | R | Cald: 641.11 Obsd: 642.21 | A |
| 110 | 4-Cl, 2-PrOPh | CF$_3$O | S | Cald: 665.19 Obsd: 666.31 | A |
| 111 | 4-Cl, 2-PrOPh | CF$_3$O | R | Cald: 665.19 Obsd: 666.31 | A |

TABLE 5-continued

| Example | Ar | R | Stereo chemistry | LC-MS data | Method |
|---|---|---|---|---|---|
| 112 | 3,5-diClPh | CF₃ | racemic | Cald: 625.11 Obsd: 625.91 | A |
| 113 | 5-Cl, 2-CF₃OPh | CF₃ | racemic | Cald: 675.14 Obsd: 675.87 | A |
| 114 | 5-Cl, 2-CF₃OPh | CF₃O | racemic | Cald: 691.13 Obsd: 691.83 | A |

TABLE 6

| Example | Ar | R | LC-MS data | Method |
|---|---|---|---|---|
| 115 | 3,5-diClPh | H | Cald: 557.13 Obsd: 558.0 | A |
| 116 | 4-CF₃OPh | H | Cald: 573.19 Obsd: 574.17 | A |
| 117 | 4-CF₃OPh | EtO | Cald: 617.21 Obsd: 618.33 | A |
| 118 | 4-Cl, 2-PrOPh | H | Cald: 581.21 Obsd: 582.30 | A |
| 119 | 5-Cl, 2-CF₃OPh | H | Cald: 607.15 Obsd: 608.09 | A |

TABLE 6-continued

| Example | Ar | R | LC-MS data | Method |
|---|---|---|---|---|
| 120 | 2,2-difluoro-benzo[1,3]dioxol-4-yl | CF₃O | Cald: 653.16 Obsd: 654.17 | A |
| 121 | 2,2-difluoro-benzo[1,3]dioxol-4-yl | MeO | Cald: 599.19 Obsd: 600.23 | A |
| 122 | 2,2-difluoro-benzo[1,3]dioxol-4-yl | H | Cald: 569.18 Obsd: 570.18 | A |
| 123 | 2,2-difluoro-benzo[1,3]dioxol-5-yl | MeO | Cald: 599.19 Obsd: 600.20 | A |
| 124 | 2,2-difluoro-benzo[1,3]dioxol-5-yl | H | Cald: 569.18 Obsd: 570.20 | A |

TABLE 6-continued

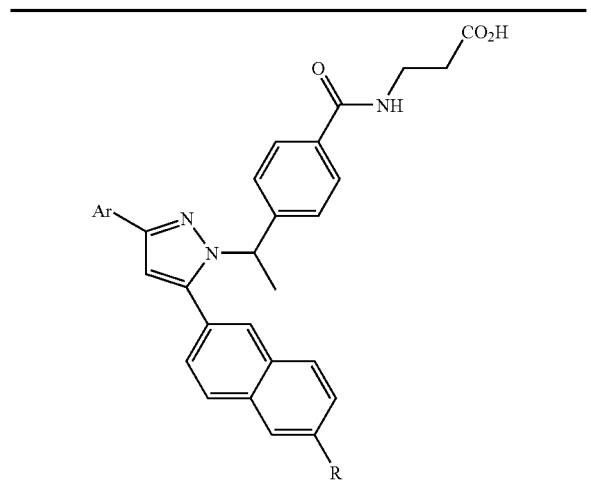

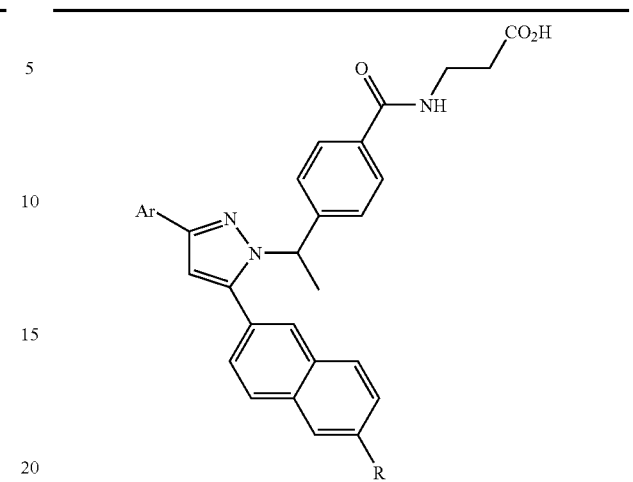

| Example | Ar | R | LC-MS data | Method |
|---|---|---|---|---|
| 125 | 2,2-difluoro-benzodioxole | $CF_3O$ | Cald: 653.16 Obsd: 654.23 | A |
| 126 | 4-ClPh | MeO | Cald: 553.18 Obsd: 554.02 | B |
| 127 | 4-$^t$BuPh | MeO | Cald: 575.28 Obsd: 576.12 | B |
| 128 | 3-F, 4-EtOPh | MeO | Cald: 581.23 Obsd: 582.31 | B |
| 129 | 3-F, 4-$CF_3$OPh | MeO | Cald: 621.19 Obsd: 622.26 | B |
| 130 | 3,5-diFPh | MeO | Cald: 555.20 Obsd: 556.15 | B |
| 131 | 4-FPh | MeO | Cald: 537.21 Obsd: 538.16 | B |
| 132 | 3-EtOPh | MeO | Cald: 563.24 Obsd: 564.29 | B |
| 133 | 3-Me, 4-FPh | MeO | Cald: 551.2 Obsd: 552.20 | B |
| 134 | 3-F, 4-MeO | MeO | Cald: 567.22 Obsd: 568.17 | B |
| 135 | tetrafluoro-benzodioxine | MeO | Cald: 649.18 Obsd: 650.24 | B |
| 136 | tetrafluoro-benzodioxine | MeO | Cald: 649.18 Obsd: 650.10 | B |
| 137 | 2-i-PrOPh | MeO | Cald: 577.26 Obsd: 578.0 | B |
| 138 | 2-MeO, 4-FPh | MeO | Cald: 567.22 Obsd: 568.20 | B |
| 139 | 3-ClPh | MeO | Cald: 553.18 Obsd: 554.15 | B |
| 140 | 2,4-diFPh | MeO | Cald: 555.20 Obsd: 556.30 | B |
| 141 | 4-Cl, 3-FPh | MeO | Cald: 571.17 Obsd: 572.28 | B |
| 142 | 2-$CF_3$OPh | MeO | Cald: 603.20 Obsd: 604.32 | B |
| 143 | 2-FPh | MeO | Cald: 537.21 Obsd: 538.33 | B |
| 144 | 3-Cl, 4-$CF_3$Ph | MeO | Cald: 621.16 Obsd: 622.29 | B |
| 145 | 3-MePh | MeO | Cald: 533.23 Obsd: 534.35 | B |
| 146 | 3-Cl, 4-$CF_3$OPh | MeO | Cald: 637.16 Obsd: 638.23 | B |
| 147 | 4-Me, 2-MeOPh | MeO | Cald: 563.24 Obsd: 564.31 | B |
| 148 | 5-F, 2-MeO | MeO | Cald: 567.22 Obsd: 568.28 | B |
| 149 | 2,4-diClPh | MeO | Cald: 587.14 Obsd: 588.21 | B |

Biological Assays

The ability of the compounds of the present invention to inhibit the binding of glucagon and their utility in treating or preventing type 2 diabetes mellitus and the related conditions can be demonstrated by the following in vitro assays. Glucagon Receptor Binding Assay A stable CHO (Chinese hamster ovary) cell line expressing cloned human glucagon receptor was maintained as described (Chicchi et al. *J. Biol Chem* 272, 7765-9(1997); Cascieri et al. *J Biol Chem* 274, 8694-7(1999)). To determine antagonistic binding affinity of compounds 0.002 mg of cell membranes from these cells were incubated with $^{125}$I-Glucagon (New England Nuclear, MA) in a buffer containing 50 mM Tris-HCl (pH 7.5), 5 mM MgCl, 2 mM EDTA, 12% Glycerol, and 0.200 mg WGA coated PVT SPA beads (Amersham), +/− compounds or 0.001 MM unlabeled glucagon. After 4-12 hours incubation at room temperature, the radioactivity bound to the cell membranes was determined in a radioactive emission detection counter (Wallac-Microbeta). Data was analyzed using the software program Prism from GraphPad. The $IC_{50}$ values were calculated using non-linear regression analysis assuming single site competition. $IC_{50}$ values for the compounds of the invention are generally in the range of as low as about 1 nM to as high as about 500 nM, and thus have utility as glucagon antagonists.

Inhibition of Glucagon-Stimulated Intracellular cAMP Formation

Exponentially growing CHO cells expressing human glucagon receptor were harvested with the aid of enzyme-free dissociation media (Specialty Media), pelleted at low speed, and re-suspended in the Cell Stimulation Buffer included in the Flash Plate cAMP kit (New England Nuclear, SMP0004A). The adenylate cyclase assay was setup as per manufacturer instructions. Briefly, compounds were diluted from stocks in DMSO and added to cells at a final DMSO concentration of 5%. Cells prepared as above were preincubated in flash plates coated with anti-cAMP antibodies (NEN) in presence of compounds or DMSO controls for 30 minutes, and then stimulated with glucagon (250 pM) for an additional 30 minutes. The cell stimulation was stopped by addition of equal amount of a detection buffer containing lysis buffer as well as $^{125}$I-labeled cAMP tracer (NEN). After 3 hours of incubation at room temperature the bound radioactivity was determined in a liquid scintillation counter (Top-Count-Packard Instruments). Basal activity (100% inhibition) was determined using the DMSO control while 0% inhibition was defined at the amount of pmol cAMP produced by 250 pM glucagon.

Certain embodiments of the invention has been described in detail; however, numerous other embodiments are contemplated as falling within the invention. Thus, the claims are not limited to the specific embodiments described herein. All patents, patent applications and publications that are cited herein are hereby incorporated by reference in their entirety.

What is claimed is:

1. A compound represented by formula I:

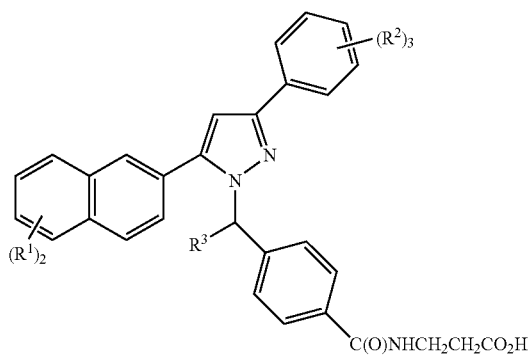

I or a pharmaceutically acceptable salt or solvate thereof, wherein:

each $R^1$ is H or is selected from the group consisting of:
(a) halo, OH, $CO_2R^4$, CN, $SO_pR^5$ or $NO_2$,
(b) $C_{1-6}$alkyl or $OC_{1-6}$alkyl optionally substituted with: (1) 1-5 halo groups up to a perhaloalkyl group; (2) $CO_2R^4$; (3) phenyl optionally substituted as follows: (i) 1-5 halo groups, (ii) 1 $CO_2R^4$, CN, $S(O)_pR^5$, $NO_2$ or $C(O)NR^6R^7$ group, (iii) 1-2 $C_{1-10}$alkyl or alkoxy groups, each optionally substituted with: 1-5 halo, up to perhaloalkyl, and 1-2 OH or $CO_2R^4$ groups;

each $R^2$ is selected from $R^1$ as defined above, or 2 $R^2$ groups can be taken together to represent a fused 5-6 membered cyclic structure containing 1-2 oxygen atoms, and 1-2 carbon atoms each of which is optionally substituted with 1-2 F atoms;

$R^3$ is H or $C_{1-3}$alkyl;
$R^4$ is H, $C_{1-6}$alkyl, and
$R^5$ represents a member selected from the group consisting of: $C_{1-10}$alkyl, Aryl or Ar—$C_{1-10}$alkyl;
$R^6$ and $R^7$ each independently represent H or $C_{1-3}$alkyl, and p is 0, 1 or 2 group.

2. A compound in accordance with claim 1, or a pharmaceutically acceptable salt thereof, wherein:

one $R^1$ is H and the other is H or is selected from the group consisting of: (a) halo, OH, $CO_2R^4$, CN, $SO_pR^5$ or $NO_2$, (b) $C_{1-6}$alkyl or $OC_{1-6}$alkyl optionally substituted with; (1) 1-5 halo groups up to a perhaloalkyl group; (2) $CO_2R^4$; (3) phenyl optionally substituted a follows: (i) 1-5 halo groups, (ii) 1 $CO_2R^4$, CN, $S(O)_pR^5$, $NO_2$ or $C(O)NR^6R^7$ group, (iii) 1-2 $C_{1-10}$alkyl or alkoxy groups, each optionally substituted with: 1-5 halo, up to perhaloalkyl, and 1-2 OH or $CO_2R^4$ groups.

3. A compound in accordance with claim 2, or a pharmaceutically acceptable salt thereof, wherein one $R^1$ is H and the other is H or is selected from the group consisting of: (a) halo or OH; and (b) $C_{1-4}$alkyl or $OC_{1-4}$alkyl, each optionally substituted with: 1-3 halo groups.

4. A compound in accordance with claim 1, or a pharmaceutically acceptable salt thereof, wherein each $R^2$ represents H or is selected from the group consisting of: (a) halo selected from Cl and F, (b) $C_{1-6}$alkyl or $OC_{1-6}$alkyl optionally substituted with 1-3 halo groups, or two $R^2$ groups taken together represent a fused 5-6 membered cyclic structure containing 1-2 oxygen atoms, and 1-2 carbon atoms, each of which are optionally substituted with 1-2 F atoms.

5. A compound in accordance with claim 1, or a pharmaceutically acceptable salt thereof, wherein: $R^3$ represents H or methyl.

6. A compound in accordance with claim 1, or a pharmaceutically acceptable salt thereof, wherein:

one $R^1$ is H and the other is H or is selected from the group consisting of:
(a) halo, OH, $CO_2R^4$, CN, $SO_pR^5$ or $NO_2$,
(b) $C_{1-6}$alkyl or $OC_{1-6}$alkyl optionally substituted with: (1) 1-5 halo groups up to a perhaloalkyl group; (2) $CO_2R^4$; (3) phenyl optionally substituted as follows: (i) 1-5 halo groups, (ii) 1 $CO_2R^4$, CN, $S(O)_pR^5$, $NO_2$ or $C(O)NR^6R^7$ group, (iii) 1-2 $C_{1-10}$alkyl or alkoxy groups, each optionally substituted with: 1-5 halo, up to perhaloalkyl, and 1-2 OH or $CO_2R^4$ groups;

each $R^2$ represents H or is selected from the group consisting of: (a) halo selected from Cl and F, (b) $C_{1-6}$alkyl or $OC_{1-6}$alkyl optionally substituted with 1-3 halo groups, or two $R^2$ groups taken together represent a fused 5-6 membered cyclic structure containing 1-2 oxygen atoms, and 1-2 carbon atoms, each of which are optionally substituted with 1-2 F atoms; and $R^3$ represents H or methyl;
$R^4$ is H or $C_{1-6}$alkyl;
$R^5$ represents a member selected from the group consisting of: $C_{1-10}$alkyl, Aryl or Ar—$C_{1-10}$alkyl;
$R^6$ and $R^7$ each independently represent H or $C_{1-3}$alkyl, and p is 0, 1 or 2.

7. A compound in accordance with claim 1 or a pharmaceutically acceptable salt or solvate thereof, wherein one $R^1$ represents H and the other is selected from Cl, F, $CF_3$ or $OC_{1-3}$alkyl;

$R^2$ represents halo, $CF_3$, $OC_{1-3}$alkyl or $OCF_3$, and
$R^3$ is H or methyl.

8. A compound in accordance with claim 1 selected from the following tables:

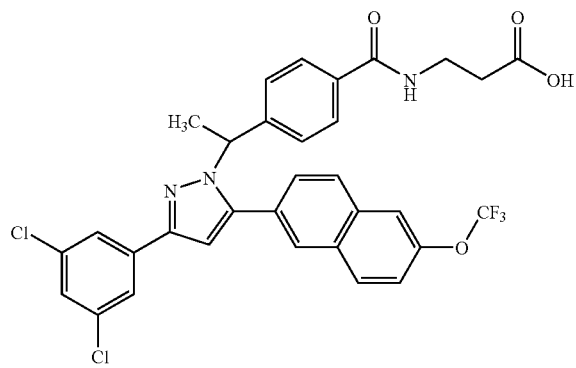
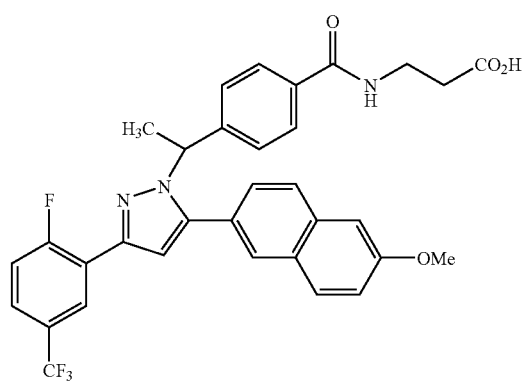
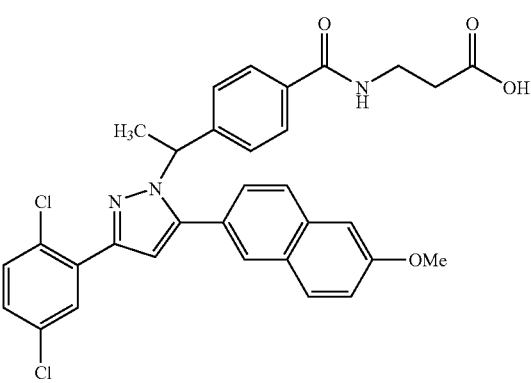
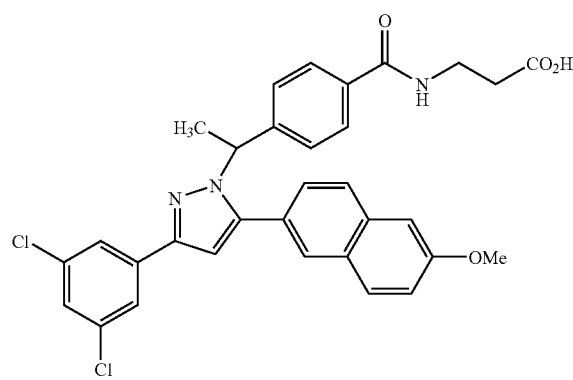
TABLE 1
| Ar | R |
|---|---|
| 3,5-diCF₃Ph | H |
| 3,5-diClPh | MeO |
| 4-CF₃, 2-PrOPh | H |
| 3,5-diClPh | CF₃O |
| 4-CF₃, 2-PrOPh | CF₃O |
| 4-Cl, 3-FPh | MeO |
| 2-CF₃OPh | MeO |
| 2-F, 5-CF₃Ph | MeO |
| 3,5-diClPh | H |
| 4-CF₃OPh | MeO |
| 4-CF₃,2-PrOPh | MeO |
| 4-CF₃OPh | CF₃O |
| 3-Cl, 2-EtOPh | MeO |
| 2,4-diFPh | MeO |
| 2-EtOPh | MeO |
| 4-Cl, 2-EtOPh | MeO |
TABLE 2
| Ar | Ar¹ |
|---|---|
| 3,5-diClPh | 7-OCF₃-naphthalen-2-yl |
| 4-CF₃, 2-PrOPh | 7-OCF₃-naphthalen-2-yl |

TABLE 2-continued

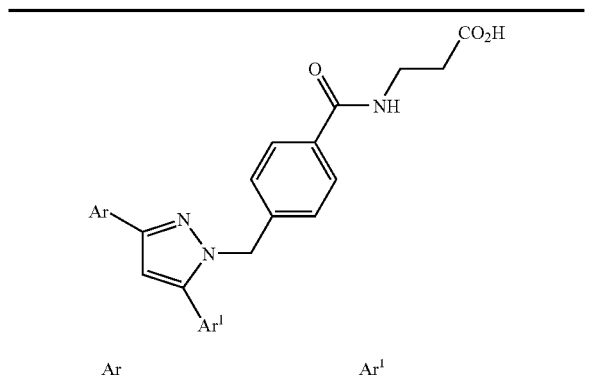

| Ar | Ar¹ |
|---|---|
| 3,5-diClPh | (7-OCF₃ naphthyl, 8-position attachment) |
| 4-CF₃OPh | (7-OCF₃ naphthyl) |
| 3,5-diClPh | (6-OCF₃ naphthyl) |

TABLE 3

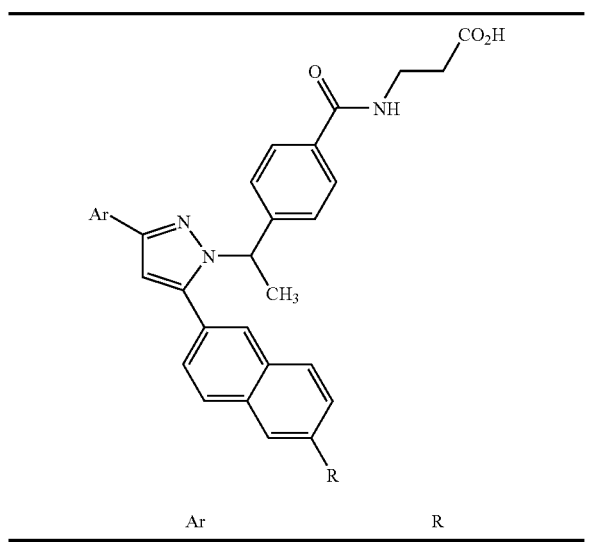

| Ar | R |
|---|---|
| 4-Cl, 2-PrOPh | CF₃O |
| 5-Cl, 2-CF₃OPh | CF₃O |
| 3,5-diClPh | EtO |
| 3,5-diClPh | CF₃ |
| 5-Cl, 2-CF₃OPh | CF₃ |
| 3,4-diClPh | MeO |

TABLE 3-continued

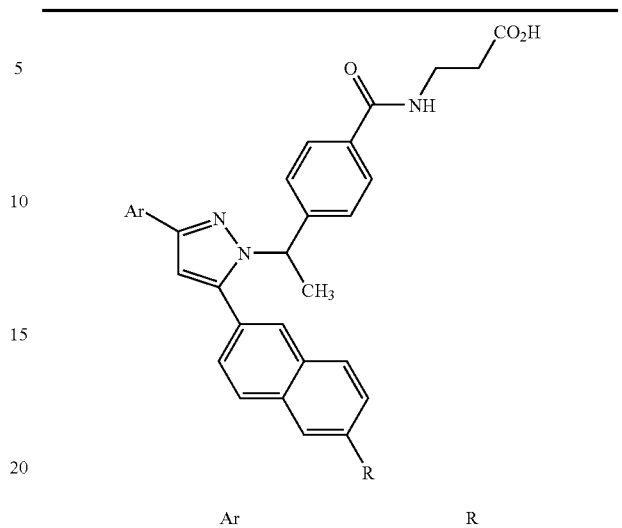

| Ar | R |
|---|---|
| 4-Cl, 2-CF₃OPh | MeO |
| 3,4,5-triFPh | MeO |
| 3-CF₃OPh | MeO |
| 3-Cl, 4-FPh | MeO |
| 2-F, 4-CF₃Ph | MeO |
| 2-F, 4-CF₃Ph | EtO |
| 3-Cl, 4-FPh | CF₃ |
| 3,4,5-triFPh | CF₃ |
| 3,4-diClPh | CF₃ |
| 2-F, 5-CF₃Ph | CF₃O |
| 4-CF₃, 2-cPrCH₂OPh | MeO |
| 4-CF₃, 2-cPentOPh | MeO |
| 3-Cl, 4-FPh | Cl |
| 3,4,5-triFPh | Cl |
| 4-Cl, 2-CF₃OPh | Cl |
| 3,4-diFPh | MeO |
| 5-Cl, 2-FPh | CF₃O |
| 3-Cl, 4-EtOPh | MeO |
| 3-Cl, 4-cPrCH₂OPh | MeO |
| 5-Cl, 2-MeOPh | MeO |
| 5-Cl, 2-PrOPh | MeO |
| 5-Cl, 2-cPentOPh | MeO |
| 2,3,5-triClPh | MeO |
| 3-Cl, 4-EtOPh | Cl |
| 3-Cl, 4-cPrCH₂OPh | Cl |
| 3-CF₃Ph | Cl |
| 2,5-diFPh | CF₃O |
| 2,4,5-triFPh | CF₃O |
| 4-Cl, 2-MeOPh | MeO |
| 4-Cl, 2-cPentOPh | MeO |
| 4-Cl, 2-PrOPh | Cl |
| 4-Cl, 2-PrOPh | MeO |
| 5-Cl, 2-CF₃OPh | MeO |
| 4-CF₃OPh | MeO |
| 3,5-diClPh | Cl |
| 5-Cl, 2-CF₃OPh | Cl |
| 3,4-diClPh | CF₃O |
| 4-Cl, 2-CF₃OPh | CF₃O |
| 3,4,5-triFPh | CF₃O |
| 3-CF₃OPh | CF₃O |
| 3-Cl, 4-FPh | CF₃O |
| 2-F, 4-CF₃Ph | CF₃O |
| 3-Cl, 4-FPh | EtO |
| 2-F, 4-CF₃Ph | CF₃ |
| 3-CF₃OPh | CF₃ |
| 2-F, 5-CF₃Ph | EtO |
| 3,5-diClPh | OH |
| 4-CF₃, 2-EtOPh | MeO |
| 4-Cl, 2-CF₃OPh | CF₃ |
| 2-F, 4-CF₃Ph | Cl |
| 3-CF₃OPh | Cl |
| 3,4-diClPh | Cl |
| 5-Cl, 2-FPh | MeO |
| 3-Cl, 4-MeOPh | MeO |

TABLE 3-continued

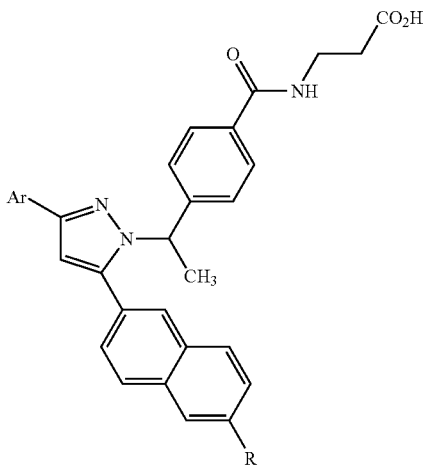

| Ar | R |
|---|---|
| 3-Cl, 4-PrOPh | MeO |
| 3-Cl, 4-cPentOPh | MeO |
| 5-Cl, 2-EtOPh | MeO |
| 5-Cl, 2-cPrCH$_2$OPh | MeO |
| 2,5-diClPh | MeO |
| 3-Cl, 4-MeOPh | Cl |
| 3-Cl, 4-PrOPh | Cl |
| 3-Cl, 4-cPentOPh | Cl |
| 2,5-diFPh | MeO |
| 2,4,5-triFPh | MeO |
| 2-F, 5-CF$_3$Ph | Cl |
| 4-Cl, 2-EtOPh | MeO |
| 4-Cl, 2-cPrCH$_2$OPh | MeO |

TABLE 4

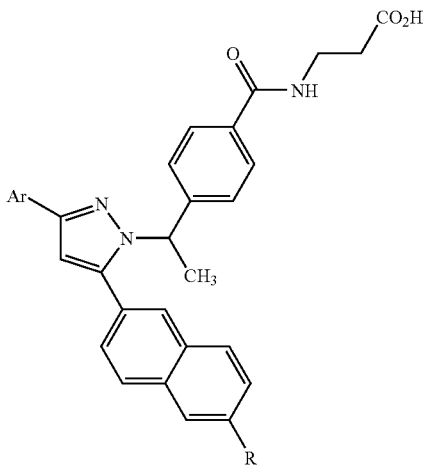

| Ar | R |
|---|---|
| 4-Cl, 2-PrOPh | CF$_3$O |
| 5-Cl, 2-CF$_3$OPh | CF$_3$O |
| 3,5-diClPh | MeO |
| 2,5-diClPh | MeO |
| 4-Cl, 2-PrOPh | MeO |
| 5-Cl, 2-CF$_3$OPh | MeO |
| 3,5-diClPh | CF$_3$ |
| 2,3,5-diClPh | MeO |

TABLE 5

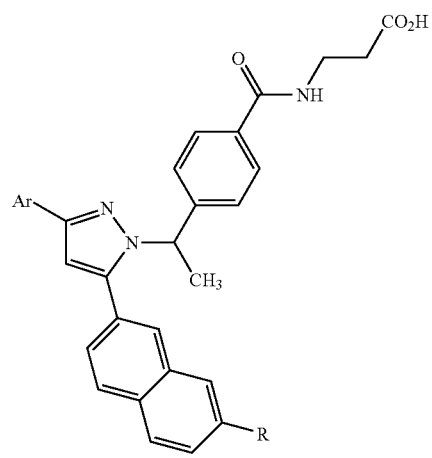

| Ar | R |
|---|---|
| 3,5-diClPh | CF$_3$O |
| 4-Cl, 2-PrOPh | CF$_3$O |
| 3,5-diClPh | CF$_3$ |
| 5-Cl, 2-CF$_3$OPh | CF$_3$O |
| 3,5-diClPh | CF$_3$O |
| 4-Cl, 2-PrOPh | CF$_3$O |
| 5-Cl, 2-CF$_3$OPh | CF$_3$ |

TABLE 6

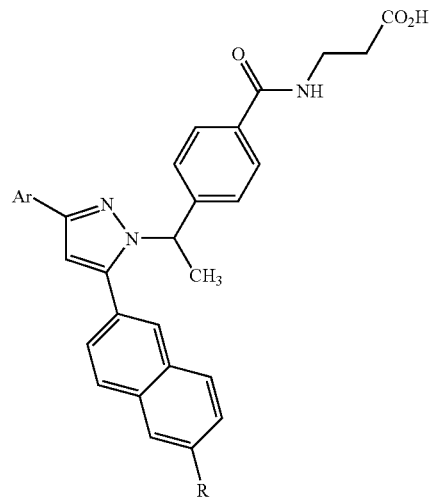

| Ar | R |
|---|---|
| 3,5-diClPh | H |
| 4-CF$_3$OPh | EtO |
| 5-Cl, 2-CF$_3$OPh | H |
|  | MeO |

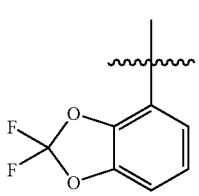

TABLE 6-continued

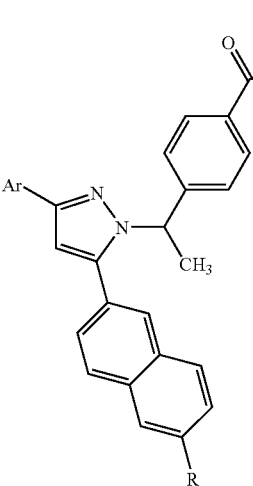

| Ar | R |
|---|---|
| 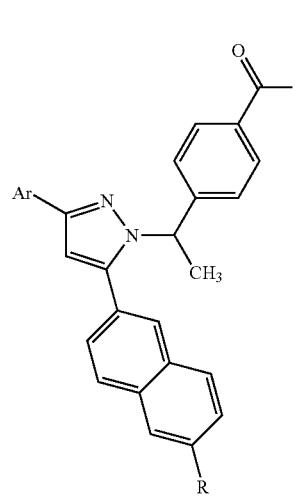 | MeO |
| 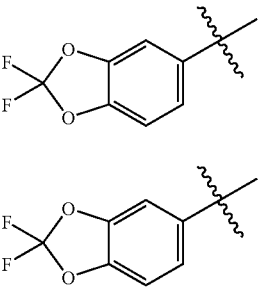 | CF₃O |
| 4-ᵗBuPh | MeO |
| 3-F, 4-CF₃OPh | MeO |
| 4-FPh | MeO |
| 3-Me, 4-FPh | MeO |
| 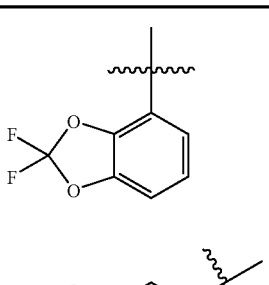 | MeO |
| 2-i-PrOPh | MeO |
| 3-ClPh | MeO |
| 4-Cl, 3-FPh | MeO |
| 2-FPh | MeO |
| 3-MePh | MeO |
| 4-Me, 2-MeOPh | MeO |
| 2,4-diClPh | MeO |
| 4-CF₃OPh | H |
| 4-Cl, 2-PrOPh | H |
| 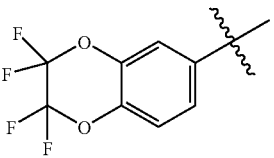 | CF₃O |

TABLE 6-continued

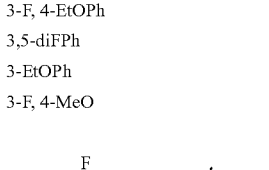

| Ar | R |
|---|---|
| 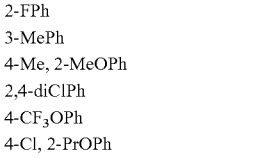 | H |
| 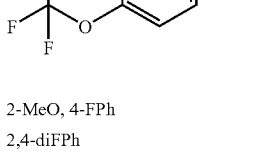 | H |
| 4-ClPh | MeO |
| 3-F, 4-EtOPh | MeO |
| 3,5-diFPh | MeO |
| 3-EtOPh | MeO |
| 3-F, 4-MeO | MeO |
| 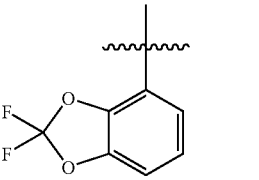 | MeO |
| 2-MeO, 4-FPh | MeO |
| 2,4-diFPh | MeO |
| 2-CF₃OPh | MeO |
| 3-Cl, 4-CF₃Ph | MeO |
| 3-Cl, 4-CF₃OPh | MeO |
| 5-F, 2-MeO | MeO | or a pharmaceutically acceptable salt thereof.

9. A compound in accordance with claim 1 selected from the following table:

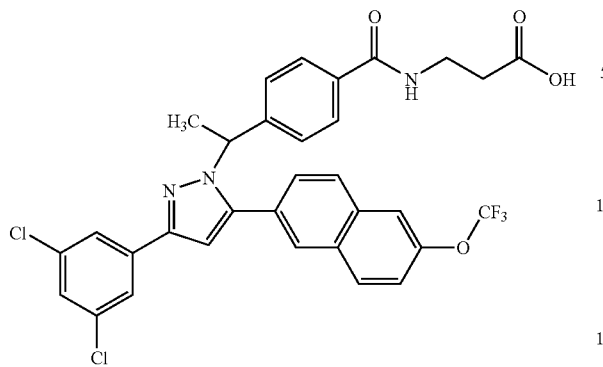

or a pharmaceutically acceptable salt thereof.

10. A compound in accordance with claim 1 represented by the structure:

or a pharmaceutically acceptable salt thereof.

11. A compound in accordance with claim 1 represented by the structure:

or a pharmaceutically acceptable salt thereof.

12. A compound in accordance with claim 1 represented by the structure or a pharmaceutically acceptable salt thereof.

13. A compound in accordance with claim 1 represented by the structure

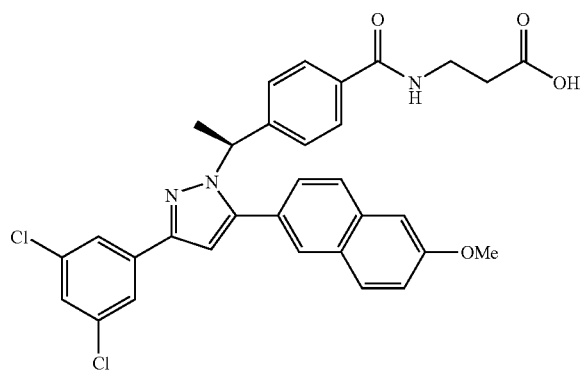

or a pharmaceutically acceptable salt thereof.

14. A compound in accordance with claim 1 represented by the structure:

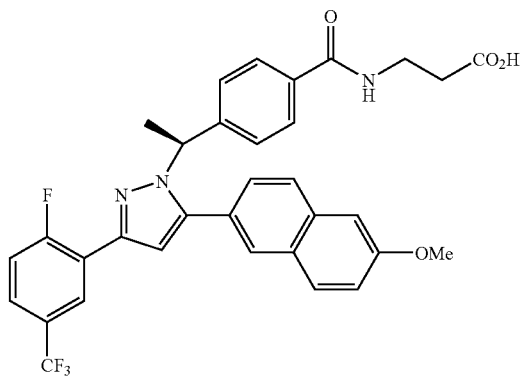

or a pharmaceutically acceptable salt thereof.

15. A pharmaceutical composition comprising a compound in accordance with claim 1, or a pharmaceutically acceptable salt thereof, in combination with a pharmaceutically acceptable carrier.

16. A method of treating type 2 diabetes mellitus in a mammalian patient in need of such treatment comprising administering to said patient a compound in accordance with claim 1 in an amount that is effective to treat said type 2 diabetes mellitus.

17. A method of delaying the onset of type 2 diabetes mellitus in a mammalian patient in need thereof, comprising administering to the patient a compound in accordance with claim 1 in an amount that is effective to delay the onset of said type 2 diabetes mellitus.

18. A method of treating hyperglycemia, diabetes or insulin resistance in a mammalian patient in need of such treatment which comprises administering to said patient an effective amount of a compound in accordance with claim 1.

19. A method of treating non-insulin dependent diabetes mellitus in a mammalian patient in need of such treatment comprising administering to the patient an anti-diabetic effective amount of a compound in accordance with claim 1.

20. A compound in accordance with claim 13 represented by the structure:

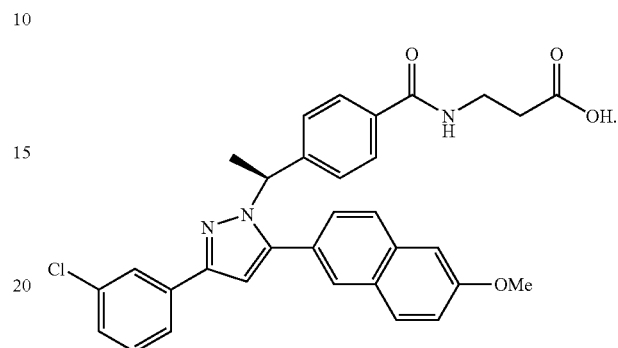

21. A pharmaceutical composition comprising a compound in accordance with claim 10 in combination with a pharmaceutically acceptable carrier.

22. A pharmaceutical composition in accordance with claim 20 in combination with a pharmaceutically acceptable carrier.

23. A compound in accordance with claim 13 of the structural formula:

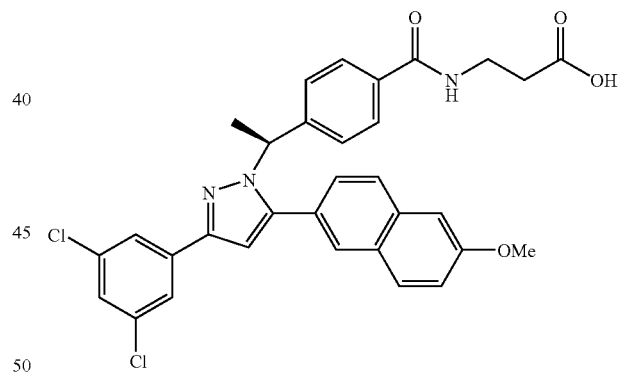

or a pharmaceutically acceptable salt thereof.

* * * * *

UNITED STATES PATENT AND TRADEMARK OFFICE
CERTIFICATE OF CORRECTION

PATENT NO. : 7,598,285 B2
APPLICATION NO. : 11/144332
DATED : October 6, 2009
INVENTOR(S) : Emma R. Parmee et al.

It is certified that error appears in the above-identified patent and that said Letters Patent is hereby corrected as shown below:

At column 76, line 33, delete Claim 23 as it is a duplicate of Claim 13.

Signed and Sealed this

Thirteenth Day of April, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,598,285 B2 | Page 1 of 1 |
| APPLICATION NO. | : 11/144332 | |
| DATED | : October 6, 2009 | |
| INVENTOR(S) | : Parmee et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1003 days.

Signed and Sealed this

Twenty-third Day of November, 2010

David J. Kappos
*Director of the United States Patent and Trademark Office*